US008354486B2

(12) United States Patent
Castillo Martinez et al.

(10) Patent No.: US 8,354,486 B2
(45) Date of Patent: Jan. 15, 2013

(54) CO-CRYSTALLIZABLE DIACETYLENIC MONOMER COMPOSITIONS, CRYSTAL PHASES AND MIXTURES, AND RELATED METHODS

(75) Inventors: Elizabeth Castillo Martinez, Dallas, TX (US); Ray H. Baughman, Dallas, TX (US); Lee J. Hall, Glendale, CA (US); Mikhail Kozlov, Dallas, TX (US); Dawn E. Smith, Martinsville, NJ (US); Thaddeus Prusik, Stroudsburg, PA (US); Carl M. Lentz, Cedar Knolls, NJ (US)

(73) Assignee: Temptime Corporation, Morris Plains, NJ (US)

( * ) Notice: Subject to any disclaimer, the term of this patent is extended or adjusted under 35 U.S.C. 154(b) by 486 days.

(21) Appl. No.: 12/730,835

(22) Filed: Mar. 24, 2010

(65) Prior Publication Data

US 2011/0086995 A1    Apr. 14, 2011

Related U.S. Application Data

(60) Provisional application No. 61/165,292, filed on Mar. 31, 2009.

(51) Int. Cl.
*C08F 238/00* (2006.01)
*G01D 21/00* (2006.01)
*C07C 275/20* (2006.01)
*C08F 2/36* (2006.01)

(52) U.S. Cl. ........ 526/285; 526/302; 116/207; 116/216; 252/183.11; 252/962; 374/102; 422/50; 436/2

(58) Field of Classification Search ............... 252/408.1, 252/962, 183.11; 116/216, 207; 526/285, 526/302; 436/2; 422/50; 374/102
See application file for complete search history.

(56) References Cited

U.S. PATENT DOCUMENTS

| | | |
|---|---|---|
| 3,999,946 A | 12/1976 | Patel et al. |
| 4,189,399 A | 2/1980 | Patel |
| 4,208,186 A | 6/1980 | Patel |
| 4,220,747 A | 9/1980 | Preziosi et al. |
| 4,298,348 A | 11/1981 | Ivory |
| 4,384,980 A | 5/1983 | Patel |
| 4,536,450 A | 8/1985 | Garito |
| 4,788,151 A | 11/1988 | Preziosi et al. |
| 4,789,637 A | 12/1988 | Preziosi et al. |
| 6,924,148 B2 | 8/2005 | Prusik et al. |
| 7,019,171 B1 | 3/2006 | Prusik et al. |
| 2008/0004372 A1 | 1/2008 | Prusik et al. |
| 2009/0131718 A1 | 5/2009 | Baughman et al. |

FOREIGN PATENT DOCUMENTS

WO    2004077097    9/2004

OTHER PUBLICATIONS

International Search Report and Written Opinion dated May 18, 2010 issued for International Patent Application No. PCT/US10/28500 filed Mar. 24, 2010.
Lee, et al, "Structural Aspects of the Thermochromic Transition in Urethane-Substituted Polydiacetylenes", Macromolecules, 2002, Vo. 35, No. 11, pp. 4347-4355.
Tachibana et al., "Crystal Structures, Polymerization, and Thermochromic Phase Changes in Urethane-Substituted Diacetylenes Crystals with Varying Alkyl Chain Lengths"., Chemistry of Materials, 2001, vol. 13, No. 1, pp. 155-158.
Enkelmann, et al., "Polymerization in Mixed Crystals", J. Materials Science, 15 (1980) pp. 951-958.
Miller et al. (Patel) in "Copolymerization of diacetylenes in the crystalline solid state. A method for recording latent fingerprints.", J. of Applied Polymer Science (1979), 24(3), 883-6.
Enkelmann, "The Solid-State Polymerization, Physical Properties, and Crystal Structures of Diacetylene Mixed Crystals" Makromol. Chem. 184, 1945-1955 (1983).
Baughman et al., "Solid-State Polymerization of Linear and Cyclic Acetylenes", Journal of Polymer Science: Macromolecular Reviews, 1978, vol. 13, pp. 219-239.
Baughman et al., "Theory of single-phase solid-state polymerization reactions", J. Chem. Phys., 73(8), 1980, pp. 4113-4125.
Baughman et al., "Solid-state reactions kinetics in single-phase polymerizations", J. Chem. Phys., 68(7), 1978, pp. 3110-2121.
Baughman et al., "Solid-State Synthesis of Large Polymer Single Crystals", Journal of Polymer Science: Polymer Physics Edition, 1974, vol. 12, pp. 1511-1535.
Hansen, C. M., Solubility Parameters: A user's handbook, 2000, CRC, p. 77, p. 80, p. 82-83.
Brandrup, J., Eds. in Polymer Handbook, 4th ed.; John Wiley & Sons, Inc. Hoboken, NJ; 1999, vol. 2 (method of van Krevelyn), p. 682-683, p. 686.
Burke "Solubility Parameters: Theory and Application" The Book and Paper Group Annual, vol. 3, 1984,The American Institute for Conservation of Historic and Artistic Works (AIC).
Wegner et al. "Topochemical Reactions of Monomers with Conjugated Triple Bonds" J. Poly. Sci.B.Poly. Letters vol. 9 (1971), pp. 133-144.
Wegner, "Topochemical Polymerization of Monomers with Conjugated Triple Bonds" Die Makromoleculare Chemie 154 (1972) pp. 35-48.

*Primary Examiner* — Fred M Teskin
(74) *Attorney, Agent, or Firm* — K&L Gates LLP

(57) ABSTRACT

Solid polymerizable diacetylenic monomer compositions, including compositions co-crystallized from a diversity of solvent systems under diverse cooling conditions, can exhibit diffraction patterns associated with the color development reactivities of the compositions. High reactivity compositions are disclosed and high reactivity and low reactivity phases can be identified. A low angle powder X-ray diffraction peak can indicate the presence of one or more crystal phases in a composition. A fingerprint region can exhibit fingerprint patterns of diffraction peaks associated with different reactivities. Information about polymerization of the diacetylenic monomers is disclosed using $^{13}C$ nuclear magnetic resonance ("NMR") characterization. Diacetylenic monomer compositions useful in ambient condition indicators, for example time-temperature indicators are disclosed.

20 Claims, 23 Drawing Sheets

| Table 4: d-Spacings | | |
|---|---|---|
| 2 Theta(deg.) | d(Å) | Intensity |
| 4.960 | 17.803 | 1000 |
| 9.916 | 8.913 | 937.76 |
| 20.452 | 4.339 | 115.57 |
| 20.909 | 4.245 | 153.78 |
| 21.989 | 4.039 | 235.46 |
| 22.844 | 3.890 | 171.72 |
| 24.274 | 3.664 | 89.03 |
| 25.656 | 3.469 | 54.19 |
| 26.920 | 3.309 | 56.44 |
| 27.676 | 3.221 | 59.41 |
| 29.062 | 3.070 | 66.27 |
| 37.201 | 2.415 | 51.56 |

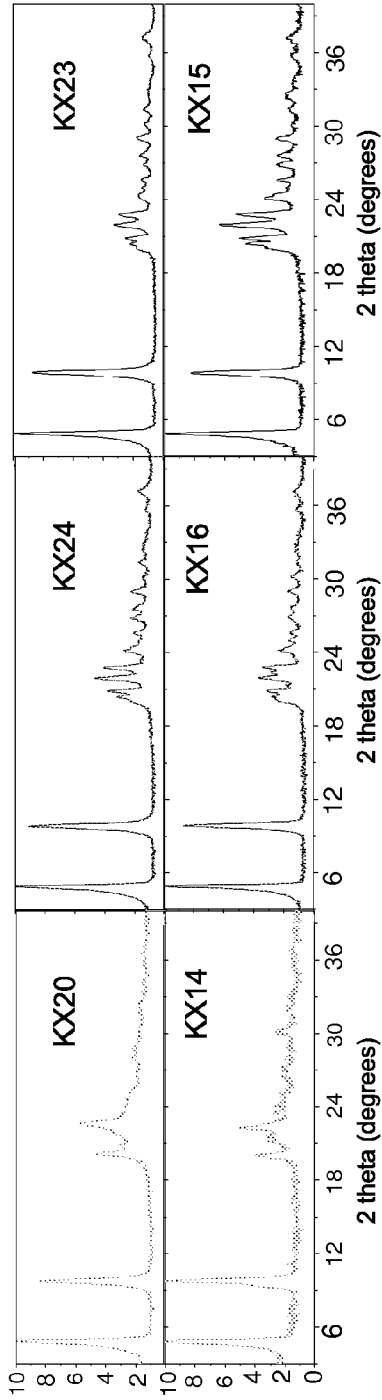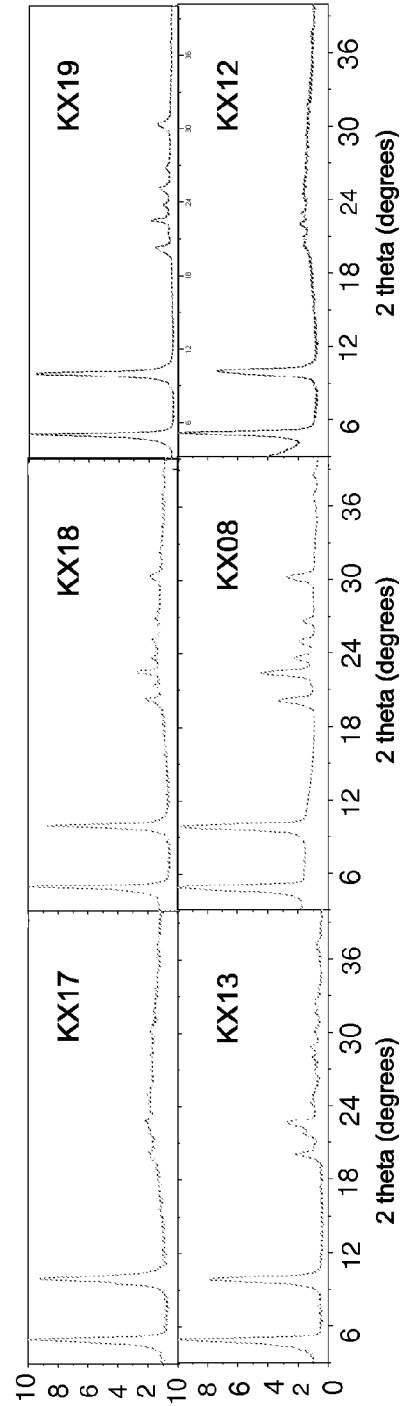
Fig. 13A
Fig. 13B

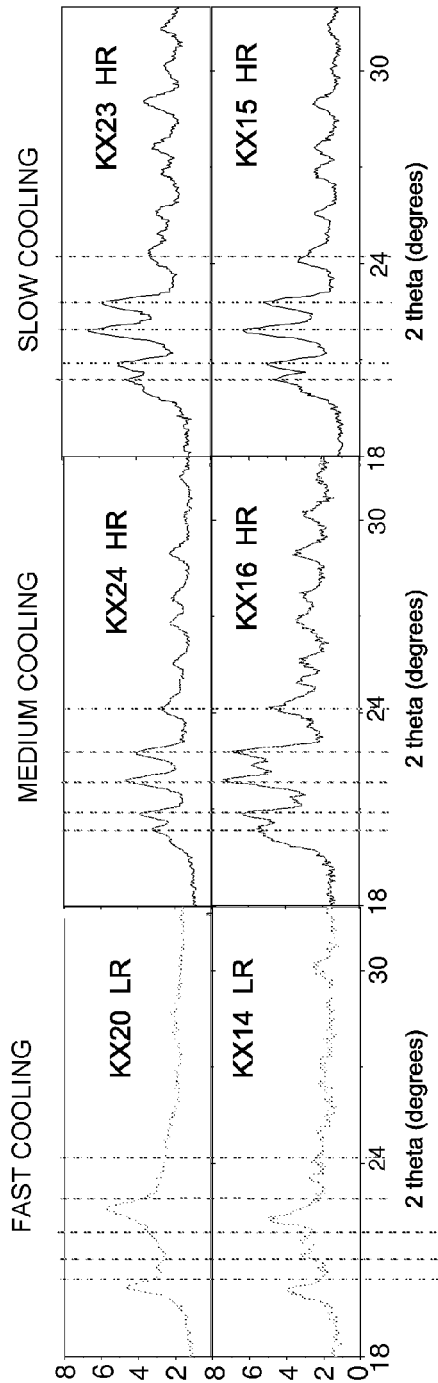
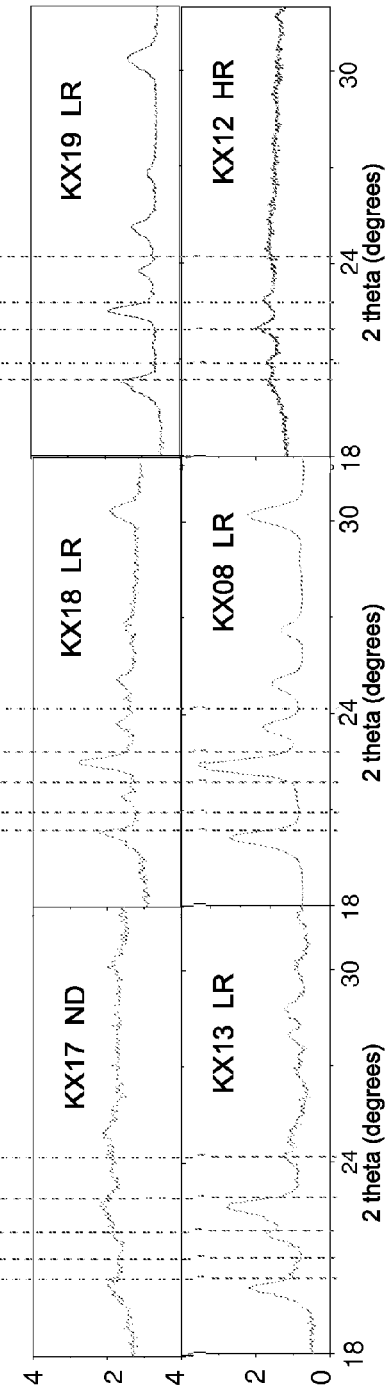
Fig. 14A
Fig. 14B

Table 5: NMR Data

| No | | KE monomer | KE polymer | KPr monomer | KPr polymer | KX monomer | KX polymer |
|---|---|---|---|---|---|---|---|
| 1 | >C=O | 160 | 159.3 | 160 | 160 | 160 | 160 |
| 2 | =C(sp²) | | 130.8 | | 134 | | 131, 128 |
| 3 | ≡C(sp) | | 98.4 | | 107 | | 106, 102, 99, 96.7 |
| 4 | ≡C(sp)-CH₂ | 76.8 | | 77.4 | | 77.7 | |
| 5 | ≡C(sp)-C≡ | 66.7 | | 65.9 | | 66.2 | |
| 6 | -NH-CH₂-CH₂ | | 42.9 | 43.2, 42.9 | 42.9 | 43.2 | 42.9 |
| 7 | -NH-CH₂-C≡ | | | | 42.2 | | 42.9 |
| 8 | -NH-CH₂-CH₃ | 36 | 35.2 | | | 35 | 35 |
| 9 | -NH-CH₂-C≡ | 31.1 | | 31.1 | | 31.2 | 30.5 |
| 10 | -CH₂-CH₂-CH₃ | | | 25.8 | 25.5 | 24.6 | 24.6 |
| 11 | -CH₃ | 15.4 | 15.9 | 12 | 12.2 | 16.1, 13 | 16.1, 13 |

Fig. 19

CO-CRYSTALLIZABLE DIACETYLENIC MONOMER COMPOSITIONS, CRYSTAL PHASES AND MIXTURES, AND RELATED METHODS

CROSS-REFERENCE TO A RELATED APPLICATION

This application claims the benefit of provisional patent application No. 61/165,292, filed on Mar. 31, 2009, the disclosure of which is incorporated by reference herein.

STATEMENT REGARDING FEDERALLY SPONSORED RESEARCH OR DEVELOPMENT (Not Applicable.)

The present invention relates to novel diacetylenic monomer compositions, mixtures and crystal phases. The compositions, mixtures and other products described herein are generally co-crystallizable and useful as active indicator agents in visual indicators of exposure to environmental conditions. Such indicators can be employed to monitor environmental conditions such as temperature that may relate to the shelf life, freshness, maturity or other characteristic of a host product. Methods described herein are useful for the preparation, characterization or use of the described compositions, mixtures and other products.

BACKGROUND OF THE INVENTION

Various diacetylenic monomers have long been used as active indicator agents in time-temperature and other ambient condition indicators to indicate the freshness or another characteristic of a host product with which the indicator is associated. Certain diacetylenic monomers undergo a solid-state polymerization reaction changing color, or another visual characteristic, in a predictable and irreversible manner in response to thermal conditions or other stimuli.

Indicators employing a diacetylenic monomer, or a composition of one or more diacetylenic monomers, as an active indicator agent can provide a simple visual indication of the cumulative exposure of a host product to, for example, heat. Such indicators can integrate time and temperature exposure in a predictable, quantitative manner and can be used to monitor the useful shelf life of perishable host products such as a vaccine, a drug or medicament, a foodstuff, an industrial product, or the like. The indicator can provide a color change at a predetermined end point to indicate possible loss of freshness of the host product, or another likely quality of the host product.

To provide a meaningful signal, it is desirable for the response characteristics of the active indicator agent to thermal exposure, or another parameter being measured, to correspond reasonably closely with the response characteristics of the host product with which the indicator is to be associated, over a range of variation of the monitored condition or conditions. Because there is a variety of potential host products for the indicators of the invention, many of which have their own distinctive profiles or patterns of color development responsiveness to thermal exposure and other environmental parameters, it would be desirable to have an extensive catalog of indicator agent response profiles from which a corresponding selection can be made.

Many polymerizable diacetylenic monomer compounds are known or have been suggested. See for example U.S. Pat. Nos. 3,999,946; 4,189,399 and 4,384,980 to Patel and U.S. Pat. Nos. 4,788,151 and 4,789,637 to Preziosi et al. (referenced herein as "Preziosi et al. '151" and "Preziosi et al. '637", respectively.) A number of the diacetylenic monomers described in these patents, and elsewhere, provide useful color changes upon polymerization in response to environmental conditions to be monitored.

However, only a limited number of known diacetylenic monomers have performance parameters that render them useful for monitoring a perishable or maturing host product and are commercially viable, i.e. can meet a range of criteria for acceptability as a commercial product. This limited number of useful diacetylenic monomers limits the choices available to an indicator formulator seeking a suitable diacetylenic monomer to match with a host product in order to monitor the host product's quality.

One approach to increasing the available choices is to modify the reactivity of a given commercially useful diacetylenic monomer so that it responds differently to a given ambient condition. A single diacetylenic monomer can then provide two or more color development response profiles for matching to host products according to whether the diacetylenic monomer is modified in one or more ways or is unmodified.

As described in Preziosi et al. '151, the activity of an acetylenic compound to environmental stimuli can be altered or controlled by contacting the compound with an effective complexing metal (or metal ion). In a comparable vein, Preziosi et al. '637, describes that the activity can be altered or controlled by contacting the compound with an effective complexing acid.

Also, U.S. Pat. No. 6,924,148 to Prusik et al. ("Prusik '148" herein) discloses varying the reactivity of a diacetylenic monomer by refluxing a solution of the diacetylenic monomer. Both increases and reductions in reactivity are described, depending upon the particular combination of diacetylenic monomer and solvent employed.

Prusik '148 also describes that the refluxed monomer products resulting from refluxing 2,4-hexadiyn-1,6-bis(ethylurea) dissolved in acetic acid for varying times appeared, under microscopic, X-ray diffraction, and other analytical technique observations, to be substantially identical, yet when tested for thermal color-change response they exhibited, with increases in reflux time, increased reactivity.

In addition, U.S. Patent Application Publication No. 2008/0004372 to Prusik et al. discloses use of a reactivity-enhancing adjuvant to adapt the reactivity of a diacetylenic indicator agent to the response characteristics of a host product. Some exemplary adjuvants described include low-temperature polymerization initiators, for example methyl ethyl ketone peroxide, polymerization accelerators, for example cobalt compounds and combinations of initiators and accelerators.

Another approach to providing an indicator agent with a new or modified color-related reactivity profile is to mix two indicator compounds together. Thus, two diacetylenic monomers can be co-crystallized to provide a co-crystallized mixture having a reactivity profile different from either of the starting materials. For example, Miller et al. (Patel) in "*Copolymerization of diacetylenes in the crystalline solid state. A method for recording latent fingerprints.*", J. of Applied Polymer Science (1979), 24(3), 883-6, describe the solid state copolymerization of 2,4-hexadiyn-1,6-bis(phenylurethane) and 2,4-hexadiyn-1,6-bis(p-cholorophenylurethane). As described, the presence of oil on a surface on to which a solution of the two compounds is sprayed affects the reactivity of the resultant co-crystallized diacetylenic phase.

Also, "Polymerization in Mixed Crystals", J. Materials Science, 15 (1980) pages 951-958 to Enkelmann ("Enkelmann 1980" herein) describes that suitably substituted diacetylenes can be co-crystallized to form substitutional solid solutions. Solid state polymerization of mixed crystals of 2,4-hexadiynylene di-p-toluenesulphonate ("1a" in Enkelmann 1980) and up to 20 percent of either 2,4-hexadiynylene di-p-chloro-benzenesulphonate ("1b" in Enkelmann 1980) or di-p-bromobenzene-sulphonate ("1c" in Enkelmann 1980), is described with reference to time conversion curves (pp. 956-958 and FIGS. 9-11). Compound 1a is similar to compound 1b and compound 1c, save that a chlorine atom in the compound 1b and a bromine atom in compound 1c replaces the toluene methyl group in compound 1a.

The active forms of compounds 1b and 1c are described in Enkelmann 1980 as being metastable, and electron diffraction patterns of microcrystals are also described which suggest that these materials are isomorphous with the reactive phase of 1a (page 957). Being "isomorphous" can be understood to mean that their crystal structures are in the same space groups, have the same molecular symmetries, and the same number of molecules in the unit cell.

Stable forms of compounds 1b and 1c, said to be completely unreactive in the solid state and therefore not polymerizable, are described as having triclinic crystal structures that are not isomorphous with the structure of compound 1a. According to Enkelmann 1980, optimum reactivity can be expected when the monomers stack in a distance equal to the polymer repeat unit of 4.9 Å with an angle near 45 degrees (page 954).

Furthermore, "*The Solid-State Polymerization, Physical Properties, and Crystal Structures of Diacetylene Mixed Crystals*" Makromol. Chem. 184, 1945-1955 (1983) to Enkelmann ("Enkelmann 1983" herein) describes co-crystallization of certain substituted diacetylenes, notably 2,4-hexadiynylene di-p-toluenesulfonate ("1a" in Enkelmann 1983) and 2,4-hexadiynylene di-p-fluorobenzenesulfonate ("1b" in Enkelmann 1983), to form substitutional solid solutions. These compounds differ by only the substitution of methyl groups in the former compound by fluorines in the latter compound. Solid solutions of one diacetylenic monomer in the other at varying concentrations are described. At each concentration the polymerization reactivity of the solid solution was found by Enkelmann to be intermediate between the reactivities of the individual diacetylenics (FIG. 9). Some X-ray diffraction data are also described (pp. 1947-1950).

Neither Enkelmann article appears to describe an indicator agent that would be commercially useful for monitoring the quality of a perishable host product.

Various other co-crystallized mixtures of diacetylenic monomers are also known from patents such as Preziosi et al. '151, Preziosi et al. '637 and Prusik '148, as well as U.S. Pat. Nos. 4,189,399; 4,208,186 and 4,384,980 to Patel, WO 2004/077097 to JP Laboratories and U.S. Pat. No. 7,019,171 to Prusik et al. ("Prusik et al. '171" herein). Some or all of these documents describe co-crystallized mixtures of various hexadiyn bis(alkylurea)s including, in particular, a co-crystallized mixture of 2,4-hexadiyn-1,6-bis(ethylurea) and 2,4-hexadiyn-1,6-bis(propylurea). The latter co-crystallized diacetylenic monomer mixture has a color development reactivity in response to thermal exposure which is faster than that of either ingredient of the mixture. This indicator agent is useful, inter alia, for monitoring host products having relatively short shelf lives, for example, fresh foodstuffs.

U.S. Pat. No. 4,384,980 to Patel describes a method of preparing an inactive form of diacetylene compounds via slow crystallization of a mixture of two or more diacetylenes from a solvent (column 4, lines 53-68 and column 5, lines 15-17). As described, the inactive forms can be converted to active forms by contact with an activating vapor.

Preziosi et al. '151 describes a procedure for the co-crystallization of various ratios of 2,4-hexadiyn-1,6-bis(ethylurea) and 2,4-hexadiyn-1,6-bis(propylurea). According to Preziosi et al. '151, X-ray analysis indicated the formation of a solid-solution and NMR (nuclear magnetic resonance, presumably) proton analysis verified the ratios used. A weight ratio of 1:2 parts of 2,4-hexadiyn-1,6-bis (propylurea):2,4-hexadiyn-1,6-bis(ethylurea) is described in Preziosi et al. '151 (Example S) as being the most reactive.

Also, Preziosi et al. '637 describes preparation of a co-crystallized mixture of 2,4-hexadiyn-1,6-bis(ethylurea) and 2,4-hexadiyn-1,6-bis(butylurea) by precipitation with petroleum ether from a dilute acetic acid solution.

In addition, Prusik '148 discloses refluxing, a mixture of two diacetylenic monomers, 2,4-hexadiyn-1,6-bis(ethylurea) and 2,4-hexadiyn-1,6-bis(propylurea) in acetic acid to vary the reactivity of the co-crystallized product.

Furthermore, Prusik '171 describes precipitation of polyacetylenic agents with control of a particle size parameter such as mean size or spread. Control is effected by mixing a warm solution of an acetylenic agent with a cold precipitation fluid and appropriate selection of a constituent of the cold precipitation fluid and/or of the temperature conditions. Comparative Example 4 of Prusik '171, which is further described herein, describes recrystallization of a solution in acetic acid of a mixture of 2,4-hexadiyn-1,6-bis(ethylurea) and 2,4-hexadiyn-1,6-bis(propylurea).

Notwithstanding these and other proposals, it would be desirable to have additional diacetylenic monomer reactivity options available.

The foregoing description of background art may include insights, discoveries, understandings or disclosures, or associations together of disclosures, that were not known to the relevant art prior to the present invention but which were provided by the invention. Some such contributions of the invention may have been specifically pointed out herein, whereas other such contributions of the invention will be apparent from their context. Merely because a document may have been cited here, no admission is made that the field of the document, which may be quite different from that of the invention, is analogous to the field or fields of the present invention.

SUMMARY OF THE INVENTION

The present invention provides novel diacetylenic monomer compositions, diacetylenic monomer crystal phases and mixtures, and related methods of preparation and characterization of such materials.

Some of the materials provided by the invention can change color in response to environmental stimuli, and exhibit new or modified reactivities and reactivity profiles. Characterization methods provided by the invention enable some materials having a physical similarities, but which exhibit different color-change reactivities to be clearly identified.

In one aspect, the present invention provides a solid monomer composition comprising a first monomer and a second monomer, each monomer having the first formula:

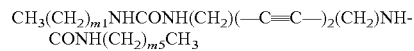

wherein in the first monomer, m1 and m5 are both 1 and in the second monomer, m1 and m5 are both 2. The solid monomer composition can exhibit an X-ray powder diffraction spectrum, collected using CuK$_\alpha$1 radiation, which spectrum has three reflection peaks between a d spacing of about 4.28 Å and a d spacing of about 3.81 Å.

The solid monomer composition can comprise any desired ratio of the first monomer to the second monomer, for example a ratio in the range of from about 3:1 to about 1:1 by weight, such as 2:1 by weight or 1:1 by weight.

Desirably, the solid monomer composition is thermally polymerizable to have a changed visual appearance.

Characterization of a diacetylenic monomer composition as having certain low angle singlet peaks in a powder x-ray diffraction pattern can be helpful in identifying compositions having useful color change reactivity and in distinguishing one composition from another composition yielding other peaks or peaks that are not clearly singlets. For example, the presence of two low angle singlet peaks can suggest the presence of a solid solution formed by co-crystallization of multiple diacetylenic monomers and distinguish a co-crystallization product from a simple mechanical mixture of the diacetylenic monomers.

If desired, the first monomer and the second monomer employable in the various aspects of the present invention can each be a compound having the following second formula:

$$CH_3(CH_2)_{m1}NHCONH(CH_2)_{m2}(-C\equiv C-)_{m3}(CH_2)_{m4}NHCONH(CH_2)_{m5}CH_3$$

wherein
m1 is 0 or is a positive integer in the range of from 1 to about 17,
m2 is a positive integer in the range of from 1 to about 10,
m3 is a positive integer in the range of from 2 to 4,
m4 is a positive integer in the range of from 1 to about 10, and
m5 is 0 or is a positive integer in the range of from 1 to about 17. m2, m3, and m4 can be the same integer, and there can be differences between m1 and m5 in the two monomers, if desired. For example, one of m1 or m5 in one of the monomers can differ from the other one of m1 or m5 in the other monomer, respectively.

Alternatively, both of m1 and m5 in one of the monomers can differ from m1 and m5 in the other monomer. If desired, m3 can be two. Alternatively, or in addition, m1 and m5 can be 1 in the first monomer and 2 in the second monomer and m2 and m4 can both be 1.

In a further aspect, the invention provides a solid monomer composition comprising a first monomer and a second monomer, each of which monomers has the second formula wherein the monomer composition comprises a crystal phase polymerized in monomer stacks generally in one crystal direction. Desirably, at least one of the monomer stacks can comprise a mixture of molecules of the first monomer and the second monomer.

In a still further aspect, the invention provides a crystal phase composition comprising a first crystal phase and a second crystal phase. The first crystal phase can comprise at least about 20 weight percent of the first monomer, the balance consisting essentially of the second monomer. The second crystal phase can comprise at least about 20 weight percent of the second monomer, the balance consisting essentially of the first monomer. Desirably, the first monomer and the second monomer have differing chemical and molecular structures. Optionally, the first crystal phase can comprise at least about 50 weight percent of the first monomer and the second crystal phase can comprise at least about 50 weight percent of the second monomer.

In yet another aspect, the present invention provides a method of making a solid crystalline acetylenic composition having a desired thermal reactivity by adjusting the structural periodicity of the acetylenic composition crystal and of the diffraction spacings associated with the structural periodicity. The method can comprise commingling a first monomer and a second monomer, each monomer having the first or the second formula and selecting a weight proportion of the first monomer based upon the combined weights of the first and second monomers to provide the desired X-ray diffraction spacing.

In yet another aspect, the invention provides a method of making a solid acetylenic crystalline composition having a desired color-changing reactivity. This method can comprise commingling a first monomer and a second monomer, the first monomer and the second monomer having different molecular structures. The method can further comprise co-crystallizing the commingled monomers from solution to provide the solid composition and identifying a high reactivity phase obtainable in the solid composition by an X-ray powder diffraction spectrum characteristic of the high reactivity phase. In addition, the method can comprise controlling the weight proportion of the high reactivity phase in the solid composition to provide the desired thermal reactivity.

The method can also comprise selecting a crystallization solvent and a cooling rate for crystallization to control the weight proportion of the high reactivity phase.

In another aspect, the invention provides a method of making an environmental condition indicator for monitoring the cumulative exposure of a perishable host product to temperature. In the method, the host product can have a desired freshness point to be indicated and the environmental condition indicator can comprise a color-changing indicator agent responsive to the environmental condition. The method can comprise determining for the indicator agent a desired color change profile for the time-related response of the indicator agent to the environmental condition. The method can also comprise determining from the indicator agent color change profile an end point corresponding approximately with the host product freshness point and selecting for use as the indicator agent a diacetylenic monomer composition having X-ray diffraction characteristics associated with the desired indicator agent color change profile.

Solid monomer compositions according to the invention can be polymerizable in the solid state to provide a polymer product capable of exhibiting four $^{13}$C NMR chemical shifts for sp carbon atoms when characterized using cross-polarization magic angle NMR. Desirably, the polymer product has a changed visual appearance from the solid monomer composition. The polymer product characterized as described is believed to comprise a copolymer of the two monomers. Polymer products apparently lacking significant quantities of homopolymers of the starting monomers are also described herein.

As is described in more detail elsewhere herein, the four $^{13}$C chemical shifts can be observable at about 106, 102, 99, and 97 ppm. The solid polymer product can also be capable of exhibiting two $^{13}$C chemical shifts for sp$^2$ carbon atoms at about 131 ppm and 128 ppm, when characterized using cross-polarization magic angle solid state NMR.

The invention also provides a copolymer composition including a copolymer chain comprising a first monomer unit and a second monomer unit, each said monomer unit having the first or the second formula before polymerization.

The invention also includes the products of the described methods as well as time-temperature or other indicators comprising these products or comprising any of the monomer compositions of the invention.

The invention provides, inter alia, novel diacetylenic monomer compositions having relatively high thermally induced color development reactivities which can be useful components of indicators intended for monitoring host products having rather short shelf lives at relatively high temperatures, typically measurable in hours, for example, freshly made sandwiches and other food products. Such relatively highly reactive indicator agents can also be useful for measuring one or more stages in the life of products having longer shelf lives, for example a temporary distribution or storage stage.

BRIEF DESCRIPTION OF THE SEVERAL VIEWS OF THE DRAWING

Some embodiments of the invention, and of making and using the invention, as well as the best mode contemplated of carrying out the invention, are described in detail herein and, by way of example, with reference to the accompanying drawings, in which like reference characters designate like elements throughout the several views, and in which:

FIG. 5 B is a table, labeled "Table 4", of the $\underline{d}$ spacings shown in FIG. 5A together with related data;

FIGS. 13A and 13B show powder X-ray diffraction patterns of various samples of co-crystallized mixtures of 2,4-hexadiyn-1,6-bis(ethylurea) and 2,4-hexadiyn-1,6-bis(propylurea) monomers showing, inter alia, the effect of the crystallization cooling rate on the reflection peaks obtained;

FIGS. 14A and 14B show portions of the X-ray powder diffraction patterns of FIGS. 13A-13B on an expanded scale;

FIG. 19 is a table of data, labeled Table 5, which data is obtainable by using $^{13}C$ NMR spectroscopy to characterize various diacetylenic monomer and polymer products;

DETAILED DESCRIPTION OF THE INVENTION

Figure 1:
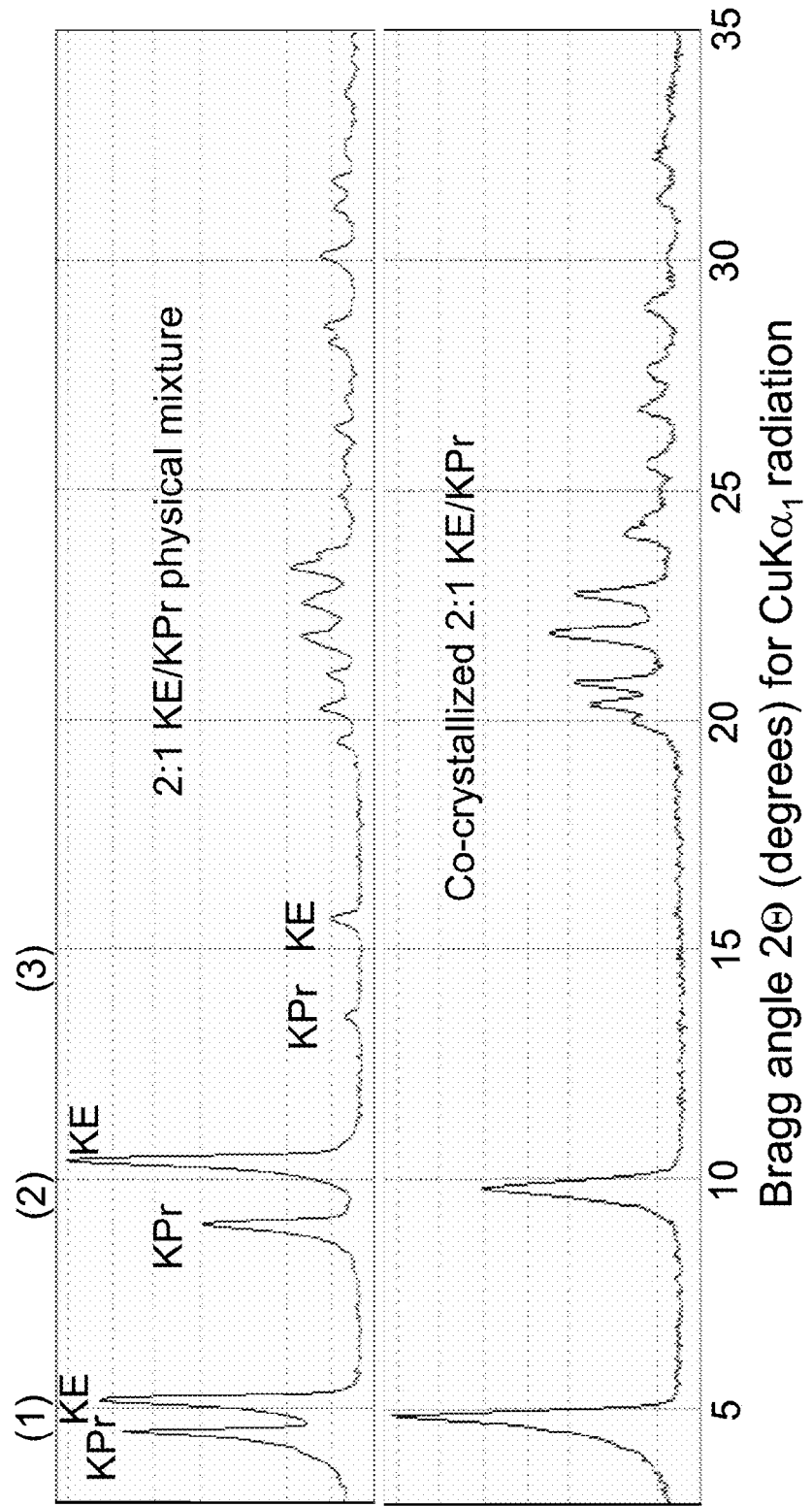
FIG. 1 shows two examples of X-ray powder diffraction patterns or diffractograms obtainable by characterization of mixtures of two crystalline diacetylenic monomers, the upper pattern being obtainable by characterization of a physical mixture of crystals of the individual diacetylenic monomers and the lower pattern by characterization of the product of co-crystallization of the two monomers.

A useful approach to selecting an indicator agent for monitoring the shelf life or freshness of a particular perishable host product comprises comparing the color development characteristics of available indicator agents with those response characteristics of the host product to the environment being monitored which cause the host product to lose freshness or to decay.

With advantage, the indicator agent can have a color change end point, for example a point of color development, which corresponds approximately with a freshness point or other quality point of the host product, such as a point of loss of freshness or imminent loss of freshness or quality. Certain diacetylenic monomers capable of environmentally induced polymerization are useful as indicator agents for these purposes.

The term "indicator agent" is used herein to include compounds and compositions that are employable as the active component of an indicator and are capable of responding to an environmental condition or stimulus, for example thermal exposure, with a visually perceptible change in appearance. Examples of indicator agents include diacetylenic compositions and diacetylenic mixtures.

The term "color" is used herein to include both chromatic and achromatic hues and appearances, for example to include red, yellow, blue, and green, secondary colors, pastels, browns, and other chromatic colors as well as white, black and gray.

Acetylenic molecules having at least two conjugated acetylene groups in the molecule are referred to herein as "diacetylenes" or "diacetylenic compounds" or "diacetylenic monomers". Diacetylenes having three conjugated acetylene groups are sometimes referred to as triynes, and those with four conjugated acetylene groups as tetraynes. Triynes or tetraynes can be employed in the practice of the invention, if desired. However, some triynes and tetraynes may be too unstable to be useful.

It will be understood that the first monomer and the second monomer are diacetylenic monomers. Accordingly, either one or both of these two compounds may be variously referenced as "monomers" and "diacetylenic monomers" herein. The first and second monomers, or diacetylenic monomers, can have various molecular structures or compositions, as is indicated generally and in context herein. Where no particular structure is described in context, the respective "monomer" or "diacetylenic monomer" is to be understood to be capable of comporting with or having formula one or two or any other relevant formula described or suggested herein.

Many commercial host products have temperature response profiles correlating the quality of the host product with cumulative temperature exposure from which a suitable freshness point can be selected. Such host product response profiles may be publicly known or may be known to the supplier of the host product. Where a suitable temperature response profile is not available, it can usually be determined by routine experimentation without undue difficulty.

The freshness or other quality point can, for example, be determined to correspond with a certain number of degree days (or weeks or months) of thermal exposure. Thus, for example, the freshness point may be reached after exposure to a relatively smaller number of days at a higher temperature or a relatively larger number of days at a lower temperature, as common sense would suggest.

If desired, such an indicator can be designed to indicate multiple stages in the quality of the host product, for example quality points occurring prior to a limit of use, at a limit of use, and after a limit of use. The indicator can be marked and can bear a visual simulation of the indicator appearance at each quality stage, for reference by a viewer of the indicator. Instruction to the viewer can be included on or with the indicator, if desired, for example "CAN BE USED", "LIMIT OF USE" and "DO NOT USE", respectively.

From two to five or any other number of desired quality stages can be employed, as desired. To provide an appropriate visual signal at each quality stage, the response profile of the active indicator agent employed in the indicator desirably can be carefully correlated with the response profile of the host product. The present invention includes such indicators employing an indicator agent having a response profile which provides an appropriate indication shortly before the host product is expected to reach each quality stage, according to the host product's response profile.

Under common conditions of fluctuating ambient temperature, the time required to reach the quality point can vary widely, and may be unpredictable without knowledge of the temperature exposure history. Indicators such as the time-temperature indicators described herein can solve this problem, by monitoring temperature exposure over time and providing a visual indication or signal when the cumulative past temperature exposure is likely to have brought the host product to the quality point.

Host product and indicator agent response profiles to other conditions such as humidity, actinic radiation, an atmosphere component, or other ambient condition can be determined in a similar manner, for the purposes of the invention, to what has been described herein for the determination of temperature response profiles. The products, methods and processes of the invention can accordingly be used for monitoring such other conditions, as appears appropriate to a person of ordinary skill in the art. The responsiveness of a particular indicator agent to a particular condition may be known to the art or can be determined by routine experimentation.

Referring to time-temperature monitoring by way of example, activation energies and rate constants can generally be used to specify both the temperature-related color change characteristics of a particular indicator agent and the response characteristics of a particular host product to temperature. The well known Arrhenius equation can usually be used to describe the temperature dependency of the color change and host response rates of reaction. The term "reactivity profile" is used herein to include the combination of activation energy and reaction constant which define the response characteristics of a host product or an indicator agent at various temperatures. Comparable considerations can be applied to the monitoring of other ambient conditions that can act on a host product and can be monitored by an indicator agent such as humidity or radiation, as will be, or will become, apparent to a person of ordinary skill in the art in light of this disclosure.

In a good indicator, it is helpful if the activation energy for the color development or other color change of the indicator agent matches the activation energy for host product decay reasonably closely. If the activation energies are significantly mismatched, the indicator may signal prematurely at some higher ambient temperatures while signaling belatedly at some lower ambient temperatures, or the reverse, depending upon whether the activation energy for the product is lower or higher than for the indicator material. Also, it is desirable for the rate constant for indicator color development to match the rate constant for host product decay reasonably closely. If the rate constants are significantly mismatched, the indicator may signal prematurely, or belatedly, at all ambient temperatures. Premature signals may cause fresh host product to be discarded. Belated signals may cause spoiled, and in some cases unhealthy, products to be consumed by end users. Predictability, reliability and consistency are also usually desirable for commercial purposes.

A large number of host products, having shelf lives ranging from a few days to several years, can potentially be monitored with indicators according to the invention, and some, but not all, of these products are mentioned herein. Other host products that can be employed will be apparent to a person of ordinary skill in the art, or will become apparent in the future, as the art develops. The number of potential applications for the indicators of the invention and the above-described considerations as to the desirability of a reasonably close match between activation energies and reaction constants points to the merits of having available an extensive catalog or inventory of indicator agents having different reactivities or reactivity profiles.

If desired, the color change characteristics of an indicator agent can be compared with the response characteristics of a host product to be monitored by plotting graphs using available data. For example, one or more graphs can be plotted showing the decline with time of the shelf life or quality of the host product, in terms of a particular quality or freshness parameter of the host product, when exposed to one or more specific temperatures. The quality parameter used will depend upon the particular host product.

For example, measurement of the hazardous species such as the growth of C. botulinum in fish, or the growth of listeria or salmonella bacteria, by culturing these or other microbes in a suitable broth can be used as a quality parameter for fish, meat, eggs or other foodstuffs. Measurement of decomposition products produced from protein decay through bacterial action, e.g. fish decomposes to give ammonia, trimethylene, bimethylene, and other products, can provide an alternative quality parameter for proteinaceous foodstuffs. Loss of texture, color, or flavor can serve as a measurable quality parameter for many food products. One example is the sponginess of baked goods.

Any one or more of various chemical characteristics associated with the loss of efficacy of a drug, a pharmaceutical or a medicament can be measured to provide a suitable quality parameter, for example, quantitative loss of an active ingredient, a change in pH, detection of hydrolysis products of, for example, atropine, acetaminophen or diazepam, dehydration of prostaglandin, isomerization of prostaglandin, oxidation of ascorbic acid or morphine or other products with comparable chemistry.

The loss of immunological potency of vaccines, or of other potency characteristics of other biologically active agents, in relation to time-temperature exposure as determined by suitable animal or other laboratory studies, can also serve as a useful quality parameter.

Based upon the host product graph or graphs, a suitable indicator agent can be selected from the available inventory of indicator agents by referring to one or more temperature-related plots for the color change of the indicator agent. An ideal indicator agent gives its warning signal at any given point on the graph before the host product reaches its expiry or loss of freshness point. In practice, depending upon the parameters of the available indicator agents, some compromise may be necessary.

In summary, to help track possible changes in the quality of a host product, it can be useful for the diacetylenic monomer employed to have response parameters to thermal exposure, or to another relevant ambient condition, that approximately correlate with the response parameters of the intended host product to the same ambient condition. For this purpose, it is useful to have a range of commercially viable diacetylenic monomers and monomer compositions that provide a variety of response parameters from which a suitable monomer for monitoring a particular host product can be chosen to provide a good match between host product and monitoring agent.

Accordingly, the present invention can uniquely identify various diacetylenic monomers and diacetylenic monomer compositions having particular color-response reactivities, including monomers and monomer compositions having new or modified reactivities. Some aspects of the invention provide a helpful description of diacetylenic monomer behavior and possible mechanisms of polymerization. These descriptions are intended to facilitate manipulation diacetylenic monomer reactivity through changes in physical processing.

In some aspects, the invention provides new diacetylenic monomer compositions and diacetylenic monomer mixtures having new color change reactivities which are useful as indicator agents and which are uniquely characterized by physical data. The invention also provides new forms of co-crystallized diacetylenic monomers, which are, or can be, uniquely characterized by physical data.

To be commercially acceptable, it is often desirable for an indicator agent to have a variety of characteristics such as low cost, lack of toxicity, the ability to provide a sharp end point with a contrasting color change with a desirable color before and after the end point, printability, and good pigment properties including smooth continuous coverage of substrate on which the indicator agent is printed for example a label. Different indicator agent characteristics may be more or less important for different applications.

Modifying the chemistry of indicator agents outright, via chemical reactions, may be undesirable because the resulting products might not be commercially useful without a burdensome inquiry into their chemical safety and study of other factors such as the ease of integration into existing product lines. Accordingly, compounds having favorable toxicology data can be advantageous for use as indicator agents. Some examples of such compounds are described elsewhere herein.

With regard to toxicology, while the indicators described herein are generally not intended to be ingested by humans or other mammals, incidental or inadvertent exposure to the chemicals in the indicator may occur. For example, if a diacetylenic monomer indicator agent is incorporated into an ink and printed onto a label which is applied to a pharmaceutical package, a consumer might absorb small quantities of the indicator agent through the skin as a result of repeated handling of the package. Or a small child might suck on a label applied to a food package.

Accordingly, the present invention provides diacetylenic monomer compositions which have new or modified condition-related color change reactivities and which are unchanged in their chemical structure. The diacetylenic monomer compositions, can usefully, but not necessarily, comprise compounds for which a favorable body of biocompatibility data is known to exist. Some of these diacetylenic monomer compositions are believed to comprise new spatial organizations of the diacetylenic monomer molecules. Some examples of such new diacetylenic monomer compositions have new physical characteristics which can be used to identify the compositions. The new physical characteristics can be determined by X-ray diffraction data or nuclear magnetic resonance data, or other suitable characterizing data.

The invention includes methods which comprise using the physical data which characterize the diacetylenic monomer compositions to select a diacetylenic monomer composition for use in monitoring a particular host product as an indicator agent, as described herein.

Linkage Between Color Change Data and Diffraction Patterns

To help better understand factors relevant to the color-changing reactivity of a diacetylenic monomer composition it could be helpful to describe or model the crystal structure of the co-crystallized composition. However, crystals suitable for characterization of the crystal structure of co-crystallized diacetylenic monomer compositions are not described herein, are believed to be commercially unavailable and to be difficult to prepare.

Instead, the invention provides powder X-ray diffraction patterns of a number of co-crystallized diacetylenic monomer compositions which it has been discovered can provide information useful to an indicator formulator. In general these patterns have two regions of interest, a low-angle region of 2θ angles up to about 10° and a fingerprint region at 2θ angles of from about 19° to about 25° when using $CuK_\alpha$ X-ray radiation.

As can be understood pursuant to the present invention, co-crystallized diacetylenic monomer compositions, as described herein, generally exhibit peaks at a lowest angle of about 4° to about 5° and also at a second lowest angle of about 9° to about 10°, referring to the 2θ angles for diffraction patterns (diffractograms) taken using $CuK_\alpha$ X-ray radiation. In a number of examples of the practice of the invention, the presence of a singlet peak at each of the lowest angle and the second lowest angle appears to be associated with a single phase crystal product. The thermally induced color development properties of such single phase crystals can be useful for visual signaling in ambient condition indicators.

The nature of a singlet peak is further described elsewhere herein, from which description it can be understood, inter alia, that a diffraction peak exhibiting a shoulder or a nascent second peak is not usually considered as a singlet peak. Some products exhibiting pronounced shoulders, well formed secondary peaks or even doublet peaks at one or both of the lowest angle and the second lowest angles appear to provide two crystal phases which may have different color-change reactivities that are identifiable in the crystalline product. Such products may have a less consistent or less attractive appearance and be less commercially desirable for use in indicators. In some cases a "salt-and-pepper" appearance of dark particles interspersed with light particles may occur.

Co-crystallized diacetylenic monomer compositions having a similar chemical composition can yield different color-change reactivity characteristics if they have different physico-chemical histories, for example, as a result of being crystallized from different solvents, under different crystallization conditions. Pursuant to the present invention, it appears that higher color development reactivities are associated with a distinctive high reactivity pattern of three or more peaks in the fingerprint region of the powder X-ray diffraction pattern. Furthermore, this fingerprint pattern can be used to identify co-crystallized diacetylenic monomer compositions having, or potentially having, higher color-change reactivities.

A low reactivity pattern can also be identified in the fingerprint region which is associated with a low color development reactivity in some diacetylenic monomer compositions.

Color development studies are usually time-consuming, often requiring a considerable number of hours even at an elevated temperature, and are generally cumbersome or tedious to perform. In contrast, when the necessary equipment is available, a powder X-ray diffraction pattern over a limited range of 2θ angles can often be quickly generated, for example in about ten minutes or so, providing a fast qualitative characterization of a sample as comprising a single high reactivity phase, a single low reactivity phase or a mixture of phases. For example, the range of 2θ angles can be limited to be sufficient to exhibit the lowest angle and second lowest angle diffraction spacing. One suitable range for the lowest angle reflection is a 2θ angle of from about 4° to about 6° for CuKα X-ray radiation. A suitable range for the second lowest angle diffraction spacing is a 2θ angle of from about 9° to about 11° for CuKα X-ray radiation. Other ranges will be apparent to a person of ordinary skill in the art and can be employed.

If desired, more laborious quantitative optical color-development studies can then be performed on a selected one or more samples whose color-changing reactivity has been characterized at least qualitatively by their powder X-ray diffraction pattern and found potentially suitable for a given application.

A further difficulty with color development tests is that the samples require careful handling. A small degree of thermally-induced polymerization can substantially change the sample color, deleteriously affecting the test.

Surprisingly, in some cases, a sample's powder X-ray diffraction pattern can be relatively insensitive to a small degree of polymerization providing similar patterns before and after some initial color change. Accordingly using a powder X-ray diffraction pattern to characterize a sample has the additional advantage that sample handling need not be so closely controlled as it must for color studies.

Thus, powder X-ray diffraction data for sample can serve as a valuable tool enhancing an indicator formulator's ability to select a color-changing co-crystallized diacetylenic monomer composition having an appropriate reactivity for monitoring a particular host product.

The invention also provides a method of preparing a diacetylenic monomer composition for monitoring the condition of a host product which comprises crystallizing a candidate diacetylenic monomer composition from solution by any of the methods described herein, characterizing the crystallized candidate diacetylenic monomer composition by determination of a diffraction pattern for the candidate diacetylenic monomer composition, by any of the methods described herein and crystallizing a further candidate diacetylenic monomer composition from solution under crystallization conditions adjusted according to the diffraction pattern characterization to provide a diacetylenic monomer composition better suited to monitoring the host product.

Diacetylenic Monomers

Spontaneously polymerizable diacetylenic monomers useful in practicing the present invention include compounds having, or complying with, the second formula, as follows:

wherein m1 is 0 or is a positive integer in the range of from 1 to about 17, m2 is a positive integer in the range of from 1 to about 10, m3 is a positive integer in the range of from 2 to 4, m4 is a positive integer in the range of from 1 to about 10, and m5 is 0 or is a positive integer in the range of from 1 to about 17. m2, m3, and m4 can be the same integer, and there can be differences between m1 and m5 in the two monomers, if desired. For example, one of m1 or m5 in one of the monomers can differ from the other one of m1 or m5 in the other monomer, respectively.

Alternatively, both of m1 and m5 in one of the monomers can differ from m1 and m5 in the other monomer. If desired, m3 can be two. Alternatively, or in addition, m1 and m5 can be 1 in the first monomer and 2 in the second monomer and m2 and m4 can both be 1.

Polymerizable diacetylenic monomers useful in practicing the present invention also include compounds having, or complying with, the first formula.

Other useful broad definitions of the first monomer and the second monomer will be apparent to a person of ordinary skill in the art in light of this disclosure, or will become apparent in the future, as the art develops. Such more broadly defined first and second monomers can be employed in the practice of this invention, if desired.

One group of polymerizable diacetylenic monomers useful in the practice of the invention and which may have favorable toxicology characteristics comprises substituted 2,4-hexadiyn-1,6-bis(alkylurea) compounds wherein the alkyl group is selected from the group consisting of ethyl-, propyl-, butyl-, octyl-, dodecyl- and octyldecyl-substituted 2,4-hexadiyn-1,6-bis(alkylurea) compounds, and the foregoing compounds wherein the alkyl substituents are linear.

Some specific examples of useful compounds in this group include: 2,4-hexadiyn-1,6-bis(ethylurea), also known as "KE"; 2,4-hexadiyn-1,6-bis(propylurea) also known as "KPr"; and co-crystallized acetylenic agents, such as a 2:1 co-crystallized mixture of 2,4-hexadiyn-1,6-bis(ethylurea) and 2,4-hexadiyn-1,6-bis(propylurea) monomers. The latter mixture is also known as "KX monomer" and may be so referenced in this application.

The term "diacetylenic monomer composition" is used herein to include compositions comprising two, or possibly more than two, diacetylenic monomers having distinctly different chemical structures. An example of a diacetylenic monomer composition comprises a mixture of 2,4-hexadiyn-1,6-bis(ethylurea) and 2,4-hexadiyn-1,6-bis(propylurea). The chemical structure of 2,4-hexadiyn-1,6-bis (propylurea) differs from that of 2,4-hexadiyn-1,6-bis(ethylurea) by two methylene groups (one in each substituent group of the monomer molecule).

U.S. patent application Ser. No. 12/261,887 to Baughman et al. ("Baughman et al." herein), the disclosure of which is incorporated by reference herein, discloses crystal structures, crystallization methods, methods of characterization, uses, possible modes of polymerization and other useful information regarding certain 2,4-hexadiyn-1,6-bis(alkylurea) compounds useful as monomers in the products and methods of the present invention. In light of this disclosure, it will be understood by a person of ordinary skill in the art that certain insights, understanding or description regarding individual diacetylenic monomers that appears in Baughman et al. can be applied, mutatis mutandis, to the co-crystallized diacetylenic monomers and related methods of the present invention.

Many of the diacetylenic monomer compositions of the invention and of the crystal phases produced by co-crystallizing diacetylenic monomer compositions, as described herein, can be characterized and identified with X-ray powder diffraction studies, or by diffraction studies using electromagnetic radiation at other wavelengths with samples of the compositions that are powders or have other physical forms. In some cases, distinctive diffractograms with unique patterns of diffraction or reflection peaks can be obtained.

X-Ray Powder Diffraction Patterns

Reference herein to an "X-ray powder diffraction pattern" is to be understood to reference an X-ray powder diffraction pattern collected using $CuK_{\alpha 1}$ radiation. The radiation employed can have any suitable wavelength, for example, 1.54056 Å, which wavelength is to be understood to be employed herein unless another wavelength is indicated. However, any suitable radiation source and wavelength can be employed to generate spectra useful for the purposes of the present invention as will be apparent to a person of ordinary skill in the art, or will become apparent in the future, as the art develops, in light of this disclosure. Also, it will be understood that the appearance of the spectrum collected may differ from those shown here in some respects, if other radiation or wavelengths is or are employed.

Furthermore, while the use of powders can be convenient for obtaining a characterizing diffraction pattern, it will be understood that similar or equivalent diffraction pattern characterization can also be performed on single crystals, if they are available, or on an array or arrays of crystals that have a degree of coordinated mutual orientation. The appearance of these diffraction patterns can differ from diffraction patterns obtained when randomly oriented powders are used. However, comparable useful information can usually be obtained, inter alia.

Solid monomer compositions according to the invention can exhibit X-ray powder diffraction peaks at collection angles determined by the diffraction spacings and the diffraction peaks exhibited can have various intensities providing a characteristic of pattern, for example a series of diffraction peaks which decrease in intensity with decreasing diffraction spacing.

In describing the X-ray powder diffraction pattern obtainable, the term "singlet peak" is used herein to include a peak appearing in an X-ray diffraction pattern which peak comprises a unique cusp and no well-defined shoulder is present on either side of the peak. Further description regarding exemplary singlet peaks appears elsewhere herein.

As has been described herein, the solid monomer composition can exhibit an X-ray powder diffraction pattern, collected using $CuK_{\alpha 1}$ radiation, which pattern has a fingerprint region comprising a distinctive pattern of peaks, for example, three reflection peaks between a d spacing of about 4.28 Å and a d spacing of about 3.81 Å.

The three reflection peaks can comprise a long spacing peak at a d spacing in the range of from about 4.28 Å to about 4.18 Å, an intermediate spacing peak at a d spacing in the range of from about 4.11 Å to about 3.99 Å, and a short spacing peak at a d spacing in the range of from about 3.94 Å to about 3.81 Å. For example, the three reflection peaks can be at d spacings of approximately 4.04 Å, 3.89 Å, and 3.66 Å, respectively, and can be characterized using X-rays at a wavelength of about 1.54 Å.

In the fingerprint region, the X-ray powder diffraction pattern can comprise a separation between the long spacing peak and the intermediate spacing peak of from about 0.10 Å to about 0.27 Å. Independently, or additionally, the pattern can comprise a separation between the intermediate spacing peak and the short spacing peak of from about 0.07 Å to about 0.26 Å.

In addition, or alternatively, the three reflection peaks can be the highest intensity peaks for the diffraction spacing range between about 4.28 Å and 3.81 Å and, independently or additionally, the intensity of the intermediate spacing peak of these reflections in the fingerprint region can be higher than the intensity of either the long spacing peak or the short spacing peak.

Also, the X-ray powder diffraction pattern can comprise a longest spacing peak and a second longest spacing peak. The longest and second longest spacing peaks can be singlet peaks and can be at d spacings of about 17.80 Å and about 8.91 Å respectively or at other suitable d spacings.

Alternatively, or in addition, the diffraction pattern can have two reflection peaks in the fingerprint region between a d spacing of about 4.40 Å and a d spacing of about 3.95 Å. The two reflection peaks can comprise a long spacing peak at a d spacing in the range of from about 4.43 Å to about 4.37 Å, and a short spacing peak at a d spacing in the range of from about 3.99 Å to about 3.92 Å. The two reflection peaks can be the highest intensity peaks in the diffraction spacing range of from about 4.43 Å to about 3.92 Å. Also, the intensities of the two peaks can be similar.

In another aspect, the present invention provides a solid monomer composition which is thermally polymerizable and which comprises a first monomer and a second monomer each of which monomers also has the first formula wherein in the first monomer, m1 and m5 are both 1 and in the second monomer m1 and m5 are both 2. In this composition, the longest and second longest X-ray powder diffraction peaks are essentially singlets. The second longest spacing peak can be at a $\underline{d}$ spacing of about half the $\underline{d}$ spacing of the longest spacing peak.

As described herein, the present invention includes a method of making a solid crystalline acetylenic composition having a desired thermal reactivity by adjusting the structural periodicity of the acetylenic composition crystal and of the diffraction spacings associated with the structural periodicity.

This method can also comprise co-crystallizing the commingled first and second monomer from solution to provide the solid crystalline acetylenic composition. The commingling can be effected to provide, in an X-ray powder diffraction spectrum of the solid crystalline acetylenic composition collected using $CuK_{\alpha1}$ radiation, lowest angle and second lowest angle diffraction peaks. Each of the diffraction peaks can be essentially a singlet peak that shifts in diffraction spacing approximately linearly with change in weight proportion of the first monomer composition to the total monomer composition.

As described herein, the invention also provides a method of making a solid acetylenic crystalline composition having a desired color-changing reactivity which comprises identifying a high reactivity phase obtainable in the solid composition by reference to an X-ray powder diffraction spectrum characteristic of the high reactivity phase.

If desired, the method can also comprise effecting commingling so that the solid composition can exhibit an X-ray powder diffraction pattern collected using $CuK_{\alpha1}$ radiation having an essentially singlet lowest angle diffraction peak and an essentially singlet second lowest angle diffraction peak. The respective diffraction spacings associated with the lowest angle and second lowest angle diffraction peaks can shift approximately linearly with change in weight proportion of the first monomer to the total monomer composition. Thus, the method can also comprise selecting a weight proportion of the first monomer effective to provide diffraction spacings associated with the desired thermal reactivity for the lowest angle and second lowest angle diffraction peaks.

In a still further aspect, the invention provides a method which comprises controlling the reactivity of a color-changeable co-crystallized monomer composition. The monomer composition can comprise a first diacetylenic monomer and a second diacetylenic monomer having the first or the second formula. The method can also comprise dissolving the first diacetylenic monomer and the second diacetylenic monomer in a solvent system at an elevated temperature of at least about 60° C. and cooling the solution from about 60° C. to about 30° C. at a cooling rate requiring a period of at least about one hour. The method can also comprise recovering crystals of the diacetylenic monomer composition from the cooled solution and determining the reactivity of the recovered crystals as measured by color-change characteristics.

If desired the method can comprise selecting the solvent system to obtain crystals of diacetylenic monomer composition having a desired color change reactivity. The elevated temperature can be at least 70° C. and cooling the solution from about 60° C. to about 30° C. can require a period of at least 90 minutes.

Polymerization

Under conditions inducing polymerization, many diacetylenic monomer molecules become chained together to form a polydiacetylene. The reaction takes place in the solid state and is irreversible. In some cases, colorless, or nearly colorless, crystals of the diacetylenic monomer, or monomers, are transformed into intensely colored crystals of polymer in response to sufficient cumulative thermal exposure or another environmental condition. The polymerization reaction can proceed spontaneously, at rates largely determined by the ambient conditions and the characteristics of the monomer materials.

Because the polymerization reaction is irreversible, the color change resulting from polymerization is also irreversible under normal conditions. This property is useful in indicators for monitoring perishable products, such as vaccines, food or medicines that may lose quality after excessive cumulative thermal exposure. Diacetylenic monomers can also be employed as the active agents in indicators used for monitoring the maturity of maturing products, for example wine or cheese, if desired. For these and other purposes, the diacetylenic monomer can be incorporated as the active agent in an indicator label or card, or other indicator device, to be associated with a host product to be monitored. The indicator device provides a color change signal, derived from polymerization of the diacetylenic monomer, which can be perceived by a human viewer at a convenient viewing distance, for example by a medical professional administering a vaccine or medicament, or a shopper selecting a food product from a refrigerated display in a supermarket. A reversible indicator may not be useful for such purposes.

Crystal structure is important for determining the solid-state polymerizability of acetylenic monomers in that if neighboring monomer molecules are not appropriately juxtaposed, polymerization may be difficult or impossible. Since the presence of a second diacetylenic monomer in solid solution in the crystal results in a modified crystal structure, the invention can employ this phenomenon to help tune the rate of the solid-state thermally induced polymerization reaction. Such tuning can produce a different time- and temperature-dependent pattern of color changes that can usefully be employed in a time-temperature indicator to provide a novel indicator for monitoring a new host product.

For example, it would be useful to have a diacetylenic monomer composition having a relatively high color-change reactivity that could be useful for monitoring products having a particularly short shelf life for example up to about 1 day, 2 days or 3 days under refrigerated conditions or short periods of up to about 3, 6 or 12 hours at room temperature. Some examples of possible host products having short shelf lives under refrigerated or room temperature conditions that can be employed in the practice of the invention include freshly-made sandwiches and other ready-made meals or snacks that can deteriorate quickly such as sushi or shellfish either of which can comprise raw or cooked fish or both.

In another useful application, a high reactivity diacetylenic monomer composition can be employed as an active indicator agent in an indicator for measuring a portion of a host product shelf life, for example, a phase of the shelf life such as a transportation or temporary storage phase, which phase can for example be 1 or 2 days or less, under refrigerated conditions, or can have another suitable period.

The change in reaction rate as a result of solid-solution formation can be either an increase or a decrease, depending upon the particular diacetylenic monomers that are mixed, their relative proportions, the reactivities of the individual diacetylenic monomers, crystallization conditions such as the solvent used, phase nucleation and growth conditions, and other factors.

Solid-solution formation can also have the beneficial effect of changing the activation energy for thermal polymerization, which can enable more precise matching of the thermal polymerization energy of a diacetylene with that of a perishable product.

Since the presence of non-acetylenic molecules in diacetylenic crystals, for example solvents, can also be used to change crystal reactivity, the presence of such non-acetylenic molecules can also be employed in some types of indicator devices that use a mixture of acetylenic molecules as an active indicator agent. That being said, the term "solid solution" is used herein to indicate the presence of two or more diacetylenic monomers in the same crystal, unless the context suggests otherwise.

Depending upon the crystal structure of the solid solution formed by two or more diacetylene monomers, the polymers formed in a spontaneous 1,4-addition reaction can theoretically be one or more copolymers or polymer chains that comprise at least two different monomer units, one or more homopolymers or polymer chains that comprise a single monomer unit, or combinations thereof.

For example, if two chemically different diacetylenic monomers are present in a solid solution and each monomer forms separate stacks in the reaction direction, two different homopolymers that are intimately mixed will be formed by polymerization. On the other hand if two different monomer units periodically or randomly mix in the reaction direction of a monomer stack, the resulting copolymer will be periodic or random, respectively.

Such diacetylenic copolymers and intimately mixed homopolymers potentially have properties that are tunable by varying the relative concentrations of monomer molecules in the monomer crystals and the co-crystallization conditions used to grow these crystals. These tunable properties can include various useful properties, for example ambient condition color-change reactivity, semiconducting properties, photoconductivity, and non-linear optical susceptibility for increasing the frequency of light and other such properties as will be apparent to a person of ordinary skill in the art, or will become apparent in the future, as the art develops.

Crystallization Methods. Various methods are known for the production of a co-crystallized mixture of 2,4-hexadiyn-1,6-bis(ethylurea) and 2,4-hexadiyn-1,6-bis (propylurea) and other heterogeneous diacetylenic monomer compositions by cooling from a solution in a solvent such as acetic acid. Methods according to the present invention of preparing a co-crystallized mixture of 2,4-hexadiyn-1,6-bis (ethylurea) and 2,4-hexadiyn-1,6-bis(propylurea) and other heterogeneous diacetylenic monomers can employ cooling procedures which are slower-acting than the relatively fast cooling procedures used in the known art. Surprisingly, these new methods can yield new diacetylenic monomer compositions having new reactivities.

As described herein, the new diacetylenic monomer compositions can generally be characterized, and distinguished from known products, by powder X-ray crystallography. In many cases powder X-ray diffraction analysis can be sufficient to distinguish a given product and can often be performed relatively quickly and easily if the equipment is available. A more complete crystal structure determination by single crystal X-ray diffraction can be more demanding. Also, single crystal X-ray diffraction usually requires a relatively large crystal which may not be readily obtainable.

In the method described in Comparative Example 4 of Prusik et al. '171, a solution of a mixture of 2,4-hexadiyn-1,6-bis(ethylurea) and 2,4-hexadiyn-1,6-bis (propylurea) in acetic acid is cooled over a period of one hour from about 70° C. to 24° C. at a controlled rate, using a preprogrammed chiller. As described in Prusik et al. '171, during this time the mixture crystallizes at a relatively slow rate, as compared with other examples in Prusik et al. '171 which employ rapid quenching. Nevertheless, the average cooling rate as described in Example 4 of Prusik et al. '171 appears to be substantially above 0.5° C./min at about 0.8° C./min. Crystals with a mean chord length of 28.1 μm, as determined by Focused Beam Reflection Methods ("FBRM"), are obtainable, according to Prusik et al. '171.

Thus, the intermediate cooling procedure and the slow cooling procedures described in Example 1 herein, employing cooling rates of 0.5° C./min or less are believed to be substantially slower than known cooling processes for co-crystallization of heterogeneous diacetylenic monomers. Some art-suggested reasons for fast cooling of diacetylenic monomer solutions to induce co-crystallization include: to form co-crystals before individual compounds crystallize out; to obtain small crystals suitable for formulation into an ink for printing; and to obtain an inactive co-crystallized mixture.

For example, Example S of Preziosi et al. '151 describes cooling an acetic acid solution of 2,4-hexadiyn-1,6-bis(ethylurea) ("1KE" in Preziosi et al. '151) and 2,4-hexadiyn-1,6-bis(propylurea) ("1KPR" in Preziosi et al. '151), in various ratios, from the boiling point of the media (110° to 115° C.) to 20° C. in a cold water bath while stirring. This appears to be a relatively fast cooling process as compared with slow and intermediate cooling processes according to the present invention. The relatively passive intermediate and slow cooling processes of the invention, also can be advantageous with regard to cost.

In contrast, some of the methods according to the present invention employ different cooling conditions from those described in Prusik et al. '171, for example, slower cooling rates than are disclosed by Prusik et al. '171 for co-crystallization of a heterogeneous diacetylenic monomer composition. For example, a method according to the present invention for co-crystallization of a heterogeneous diacetylenic monomer composition from solution comprises a cooling procedure requiring at least one hour to cool the solution from about 60° C. to about 30° C., which can be described as an "intermediate" cooling rate. This cooling procedure provides an average rate of cooling of not more than about 0.5° C./min which maximum cooling rate can be continued to lower temperatures, if desired, for example to about 30° C. or to 24° C.

Since additional time is required to cool the diacetylenic monomer composition from about 30° C. to 24° C., this cooling procedure is significantly slower than what is described in Example 4 of Prusik et al. '171. If the crystallization solution, or liquor, is initially at a temperature above 60° C., additional time will be required to cool the solution to 60° C., further distinguishing the inventive cooling method from what is described in Example 4 of Prusik et al. '171.

No cooling rate figures are given in Example S of Preziosi et al. '151 so that a direct comparison in terms of cooling rate cannot be made with Preziosi et al. '151 However, Preziosi et al. '151 appears to employ active cooling, employing a cold water bath and stirring.

Unlike Preziosi '151, the cooling procedures employed in the methods of the invention use passive cooling methods implying slower cooling rates. For example, in an intermediate cooling procedure employable in practicing the present invention, the diacetylenic monomer samples and solvent system are introduced to one or more containers, for example vials, and a hot water bath is employed to provide heat for dissolving the diacetylenic monomers in the solvent system. The hot water bath with the vials containing the samples is then allowed to cool passively in a room temperature environment. If desired, the hot water bath can be held in a reasonably draft-free environment while cooling and optionally the surface of the water bath can be covered to prevent evaporative cooling and the water bath can also be covered and or wrapped with aluminum foil to reduce radiative heat losses.

In a slow cooling procedure employable in practicing the present invention, the containers and contained samples, together with the heating water from the water bath are transferred to an insulated environment, for example a vacuum flask, where the containers and heating water are allowed to cool passively in a room temperature environment. Cooling proceeds at a slower rate than in the intermediate procedure described herein.

Usefully, cooling can be continued to a temperature below about 40° C., for example to below about 30° C. or below about 25° C. Promptly after reaching a desired temperature, the crystallization mixture can be filtered and the collected crystals washed if desired and further processed or transferred to a freezer for cold storage. Such operations are desirably performed promptly to avoid or reduce room-temperature polymerization of the diacetylenic monomers which could adversely affect their temperature monitoring or other properties.

Polymerization can begin to occur as the monomer crystal forms leading to color development. A modest amount of color development can sometimes be tolerated in the design of the time-temperature indicator, with adjustments, if necessary.

Usefully, in the crystallization methods according to the invention, the diacetylenic monomer composition can be dissolved in a solvent system at an elevated temperature. Any suitable solvent or solvent system, and any suitable elevated temperature compatible with the boiling point of the solvent or solvent system employed, can be used.

Some examples of useful solvent systems for dissolving diacetylenic monomer compositions for use in practicing the invention include glacial acetic acid and other conventional diacetylenic monomer solvents such, for example, as glacial acetic acid, propionic acid, dimethyl formamide ("DMF") and dimethyl sulfoxide.

Some further examples of solvent systems useful in practicing the invention include individual solvents such as methanol, formic acid, dimethyl sulfoxide, ethylene glycol, allyl alcohol, 2-aminoethanol; 1,1,3,3-tetramethylurea; dichloroacetic acid and trifluoroacetic acid.

Solvent systems useful in the practice of the invention can also include miscible solvent mixtures, for example mixtures of water with another solvent having suitably complementary solubility parameters. The mixture with water can comprise from about 1 to about 40 percent by weight water, based on the weight of the solvent system, from about 4 to about 25 percent by weight water or another suitable proportion. If desired, the other solvent or solvents can have a hydrogen bonding parameter of not more than about 15 MPa$^{1/2}$ and can have a polar bonding parameter of not more than about 18 MPa$^{1/2}$. Some other useful solvent systems comprise non-aqueous mixtures of solvents, including mixtures of non-alcoholic ones of the individual solvents mentioned above with a suitable alcoholic solvent or solvents.

The following are some examples of solvent systems useful in the practice of the invention wherein, in each case, the proportion of water is based upon the weight of the solvent system:

a mixture of acetic acid and water in a proportion of from about 5 percent to about 25 percent of water, the balance being acetic acid;
   a mixture of acetone and water in a proportion of from about 5 percent to about 25 percent of water, the balance being acetone;
   a mixture of dimethyl formamide ("DMF" herein) and water in a proportion of from about 5 percent to about 25 percent of water, the balance being dimethyl formamide;
   a mixture of dimethyl sulfoxide and water in a proportion of from about 0 percent to about 25 percent of water, optionally at least about 5 percent water, the balance being dimethyl sulfoxide;
   a mixture of ethanol and water in a proportion of from about 0 percent to about 25 percent of water, optionally at least about 4 percent water, the balance being ethanol;
   a mixture of pyridine and water in a proportion of from about 1 percent to about 25 percent of water, optionally at least about 5 percent water, the balance being pyridine;
   a mixture of 1,1,3,3-tetramethylurea and water in a proportion of from about 1 percent to about 25 percent of water, optionally at least about 5 percent water, the balance being 1,1,3,3-tetramethylurea; and
   a mixture of dimethyl sulfoxide and ethanol in a proportion of from about 10 percent to about 90 percent of water, optionally at least about 30 percent water, the balance being dimethyl sulfoxide, for example an approximately 50:50 mixture.

Other solvents and solvent systems that can be employed will be apparent from Baughman et al. Still further solvents and solvent systems that can be employed will be apparent to a person of ordinary skill in the art, or will become apparent in the future, as the art develops.

The elevated temperature can be above about 60° C., for example in the range of from about 70° C. or 80° C. to about 100° C., or higher, depending upon the boiling point of the solvent system and the heating method employed. Usefully, heating can be provided by a heating mantle, for example a water bath or other apparatus suitable for providing temperature-controlled, moderate heat to the solution, and the heating mantle can extend around one or more containers containing the solution. The elevated temperature can be determined at the heating mantle, noting that the actual temperature of the solution may be a little lower.

In such cases, in the intermediate cooling procedure the hot solution can take from about 5 minutes to about 20 minutes or more to cool from an initial, elevated temperature of 80° C. or higher, to about 70° C. and can take from about 10 minutes to about 50 minutes or more to cool from the initial temperature to about 60° C. Cooling from about 70° C. to about 60° C. can take from about 5 minutes to about 40 minutes, or more, for example from about 10 minutes to about 20 minutes or more when employing an intermediate cooling procedure, pursuant to the present invention.

Some examples of cooling procedures employable in the practice of the present invention for co-crystallization of heterogeneous diacetylenic monomer compositions from solution include a cooling procedure requiring more than one hour to cool the solution from about 60° C. to about 30° C.; which is an average cooling rate in this temperature range of not more than about 0.43° C./min. For example, the cooling rate may be such as to require from about 75 to 150 minutes, or more, to cool the solution from about 60° C. to about 30° C.; which is an average cooling rate in this temperature range of from about 0.4° C./min to about 0.2° C./min. Some examples of useful cooling periods to cool the solution from about 60° C. to about 30° C. are at least about 70 minutes and at least about 90 minutes.

In addition the cooling procedure may require from about 10 minutes to about 75 minutes or more to cool the solution from about 30° C. to about 24° C.; which is an average cooling rate in this temperature range of from about 0.6° C./min to about 0.08° C./min.

However, the cooling procedure can employ still more time to cool the solution from about 30° C. to about 24° C., for example from about 75 to 150 minutes, or more; which is an average cooling rate in this temperature range of from about 0.08° C./min to about 0.04° C./min. Methods of the invention employing this cooling step are also distinguished from Prusik et al. '171 by the time taken to cool through the short temperature range of from about 30° C. to about 24° C.

The above described cooling methods requiring more than one hour, for example at least 70 minutes, to cool a hot heterogeneous solution of diacetylenic monomers from about 60° C. to about 30° C., can be described as "intermediate" or "medium" cooling, or as employing "intermediate" or "medium" cooling rates. Quicker cooling rates can be described as "fast" cooling.

Where a co-crystallization process according to the invention employs a diacetylenic monomer solution at a temperature significantly above 60° C., for example 75° C. or higher, in an intermediate cooling procedure employed in the practice of the invention, any suitable cooling rate to reduce the temperature to about 60° C. can be employed. For example, cooling to 60° C. can take less than one hour or may be more rapid, being effected in ten minutes or less.

In the practice of the present invention, intermediate cooling can be effected by allowing a water bath charged with a suitable container or containers of hot diacetylenic monomer solution, and which is initially at the temperature of the hot diacetylenic solution, to cool passively in a room temperature, low draft, or draft-free environment. Optionally, the upper surface of the water bath can be covered to inhibit radiative and evaporative heat losses.

If desired, prior to cooling, the water bath can be heated and employed to dissolve the heterogeneous diacetylenic monomer product in a suitable solvent or solvent system at an elevated temperature.

Other suitable equipment or procedures to provide desired cooling conditions will be, or become, apparent to a person of ordinary skill in the art. For example, a preprogrammed chiller can be employed and can be programmed with a desired final temperature and duration of cooling, or with other suitable parameters.

One example of a suitable chiller which can be employed is a Cole-Parmer Polystat® Programmable-Controller Bath model R12122 available in various sizes. Alternatively, a Thermo Scientific NESLAB RPC controller model R-13550 can be employed to run pre-determined temperature profiles with a NESLAB Digital One Plus bath.

Some fast cooling methods are known for effecting co-crystallization of certain diacetylenic monomer mixtures from diacetylenic solutions and these known methods generally effect cooling from an elevated temperature to room or near-room temperature in less than an hour, for example in half an hour or less. Some methods can cool more rapidly, bringing the crystallizing product to room or near-room temperature in a few minutes. For example, fast quench cooling can be employed wherein the diacetylenic monomer solution, within or without a container, is poured or dumped into a cold bath maintained at a low temperature. The low temperature can be about freezing, about 0° C. or substantially lower, for example about −35° C. to −40° C. Such fast quench cooling can reduce the temperature of the hot diacetylenic monomer solution to room, freezing or a lower temperature in a couple of minutes or less.

Relatively slow cooling rates can also be employed in the practice of the present invention, if desired. For example, the cooling procedure may comprise a slow cooling rate which requires more than two hours to cool the diacetylenic monomer solution from a temperature of about 60° C. to about 30° C. Such slow cooling can be effected employing a vacuum flask or in another suitable manner, as will be, or become, apparent to a person of ordinary skill in the art.

Some examples of the preparation and characterization of co-crystallized diacetylenic monomer compositions and methods will now be described, for purposes of illustration of the practice of the invention and without limiting the scope of the invention.

EXAMPLE 1

Co-crystallization of a 2:1 2,4-hexadiyn-1,6-bis (ethylurea)/2,4-hexadiyn-1,6-bis(propylurea) Mixture at different cooling rates 0.133 g of 2,4-hexadiyn-1,6-bis(ethylurea) and 0.067 g of 2,4-hexadiyn-1,6-bis (propylurea), a 2:1 weight proportion, are weighed together into individual 20 ml scintillation vials. Solvent sufficient to provide 2 to 8 grams of a solution is added to each vial, as follows to provide the indicated combined weight concentration of the two monomers:
1.8 grams of solvent 10 percent;
4.8 grams of solvent 4 percent; and
7.8 grams of solvent 2.5 percent.

Separate vials are prepared using glacial acetic acid ("acetic acid" herein) and aqueous ethanol having a proportion by weight of approximately 80:20 ethanol to water. Unless the context indicates, "aqueous ethanol" is used herein to indicate the product of mixing 80 parts by weight of ethanol with 20 parts by weight of water. "Ethanol" as employed herein refers to pure ethanol which under normal storage conditions may contain up to about 4 percent water by weight, so that the water content of the aqueous alcohol mixture can be somewhat greater than 20 parts by weight.

A magnetic stirrer is inserted and each vial is sealed. The vials are immersed into a water bath maintained on a hotplate at a temperature of about 90° C. for acetic acid or about 80° C. for aqueous ethanol, with the water level above the level of the solution in the vial. The water bath is formed of heat-resistant glass and having a volume which is about 50 mm high by about 100 mm in diameter.

The mixture is stirred and the solids are dissolved quickly with manual shaking to ensure dissolution of solid remaining on the wall of the vial. After 10 minutes at the respective temperature of about 90° C. or 80° C., the hotplate and stirrer are switched off. The solution is then cooled, without stirring, in batches at different cooling rates, slow, intermediate and fast, as described below, causing precipitation of the dissolved materials.

Fast Cooling. A first batch of vials is fast cooled by removal from the water bath where they are held at the respective temperature of about 90° C. for acetic acid, or about 80° C. for aqueous ethanol, according to the solvent employed, and is quickly cooled by quenching in ice-water at about 0° C. With fast cooling, the solution in the vials can usually cool to room temperature of about 24° C. in less than one minute.

Intermediate Cooling. A second batch of vials is cooled at an intermediate, or medium, cooling rate by allowing the water bath used for heating the solution to cool passively in a room temperature (25° C.), low draft environment, without stirring. The surface of the water bath is covered with insulating hollow plastic spheres to prevent water evaporation and the water bath is covered with aluminum foil to help reduce heat loss. With intermediate cooling, the solution in the vials can usually cool to room temperature of about 24° C. in about 4 to 5 hours or more.

Slow Cooling. A third batch of vials is slow cooled by transferring the vials and heating water from the water bath, while still at a temperature of about 90° C. or 80° C., to a vacuum flask having dimensions of about 120 mm high by 50 mm in diameter. Some plastic spheres are also transferred to the vacuum flask and the whole system is covered with aluminum foil and maintained in a draft-free room temperature environment. The temperature of the system is monitored by a thermometer inserted in the water and held in contact with the vacuum flask. When the temperature reaches about 30° C., the samples can be removed from the vacuum flask and allowed to cool to room temperature. With slow cooling, the solution in the vials can usually cool to a room temperature of about 24° C. in about 6 hours or possibly more. Desirably, the samples are filtered and further processed, as described in Example 2, below, after no more than about 7 hours, even if the temperature is a little above room temperature.

Extended Cooling. A fourth batch of vials is cooled over an extended period by following the slow cooling procedure with the difference that the vacuum flask employed is a short vessel having dimensions of about 50 mm high by about 100 mm in diameter. Extended cooling takes longer than slow cooling. For example, the measured time for extended cooling can be close to that for slow cooling with a slightly slower initial cooling rate of 1 degree less in the first 2-3 hours of cooling.

As will be understood by a person of ordinary skill in the art, the cooling time to room temperature depends upon a variety of factors including the cooling container employed, the coolant, if any, the sample size and the container size. These parameters can be varied to provide cooling conditions comparable to the conditions described herein.

Figure 8:
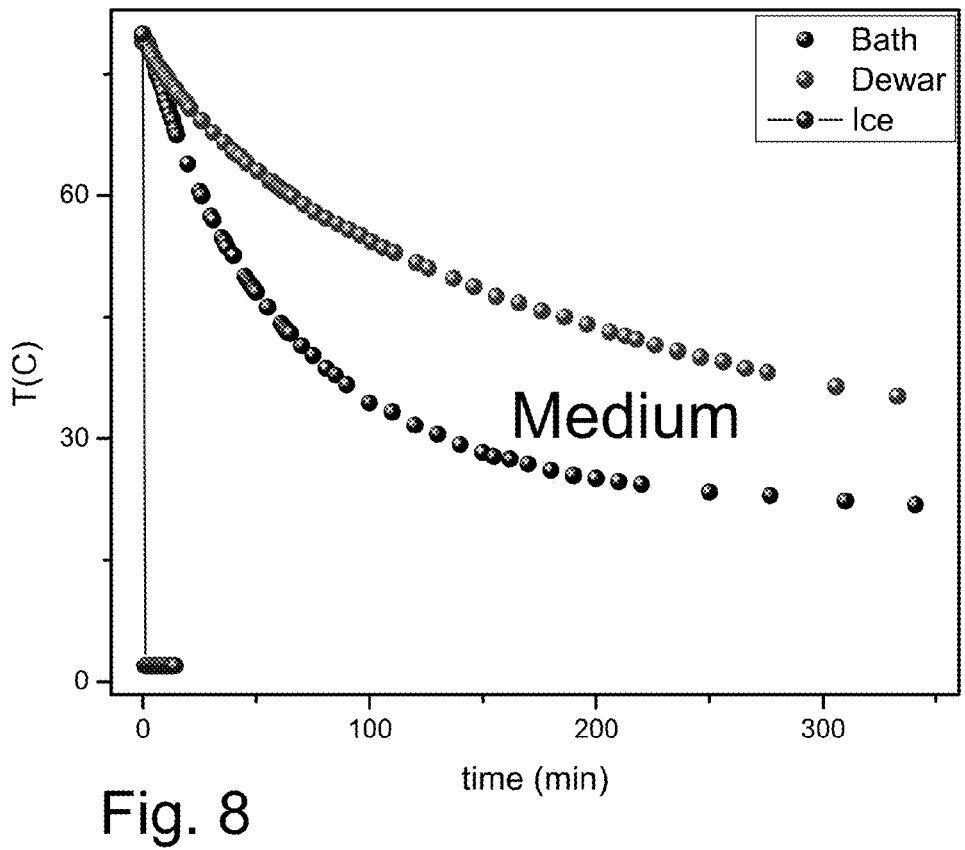
FIG. 8 graphically depicts rates of cooling in three different cooling systems employable in the practice of the invention.

Graphs showing examples of the temperature decline with time of each cooling system are shown in FIG. 8. As noted in FIG. 8, under fast cooling the sample is expected to cool a little more slowly than the measured temperature suggests. Nevertheless, under fast cooling, the sample is likely to reach 30° C. in less than 30 minutes. The times taken to reach various temperatures, under intermediate (medium) cooling and slow cooling, as can be seen from FIG. 8, are shown in Table 1.

TABLE 1

Cooling Rates

|  | Fast Cooling | Intermediate Cooling | Slow Cooling | Extended Cooling |
|---|---|---|---|---|
| Time to 60° C. | <1 min. | About 25 min. | >60 min. | >60 min. |
| 60° C. to 30° C. | <1 min. | About 100 min. | >300 min. | >300 min. |
| 30° C. to 24° C. | <1 min. | About 90 min. | Not relevant. | Not relevant. |

EXAMPLE 2

Filtration and Drying

When each of the precipitated co-crystallization mixtures produced in Example 1 reaches room temperature, each vial is opened and residual solution is filtered off through a filter plate having a 2 μm pore size, for example a TTTP isopore filter from Genesys (Korea) which is a polycarbonate, track-etched filter.

The crystals collected are washed with acetone, placed in aluminum boats, covered with perforated aluminum foil to maintain the crystals in darkness and dried under vacuum for 1-2 hours at room temperature. If not intended for immediate use, the co-crystallized monomer crystals are then promptly transferred to a freezer for storage. It is believed that little polymerization occurs when following the procedures of Examples 1 and 2. In the case of higher reactivity monomers, drying can be curtailed or conducted at a lower temperature, if desired, to reduce nascent polymerization.

The average particle size of the crystals obtainable is dependent upon the cooling conditions. Slow and extended cooling can yield average particle sizes in the range of several hundreds of microns. Intermediate and fast cooling can yield smaller crystals of the order of about 20 microns average particle size.

EXAMPLE 3

Co-crystallization of a 2,4-hexadiyn-1,6-bis(ethylurea)/2,4-hexadiyn-1,6-bis(propylurea) Mixture at a 1:1 Weight Ratio Example 1 is repeated employing 0.1 g of 2,4-hexadiyn-1,6-bis(ethylurea) and 0.1 g of 2,4-hexadiyn-1,6-bis(propylurea) in place of the weights of monomer stated in Example 1.

EXAMPLE 4

Co-crystallization of 2,4-hexadiyn-1,6-bis(ethylurea)/2,4-hexadiyn-1,6-bis(propylurea) Mixtures from Acetic Acid at Various Weight Ratios Example 1 is repeated employing following weight ratios of 2,4-hexadiyn-1,6-bis (ethylurea):2,4-hexadiyn-1,6-bis (propylurea) to a total weight of 0.2 g of monomer: 1:0, 9:1, 3:1, 2:1, 1:1, 1:3, 1:9, 0:1. These mixtures are used in place of the weights of monomer stated in Example 1. 1.8 g acetic acid is employed as solvent and a water bath temperature of about 90° C. is used. Cooling for each sample is at an intermediate cooling rate, as is described in Example 1.

EXAMPLE 5

Co-crystallization of 2,4-hexadiyn-1,6-bis(ethylurea)/2,4-hexadiyn-1,6-bis(propylurea) Mixtures from Ethanol at Various Weight Ratios Example 1 is repeated employing following weight ratios of 2,4-hexadiyn-1,6-bis (ethylurea) to 2,4-hexadiyn-1,6-bis (propylurea) to a total weight of 0.2 g of monomer: 1:0, 2:1, 1:1, 1:2, 0:1. These mixtures are used in place of the weights of monomer stated in Example 1. 4.8 g aqueous ethanol is employed as solvent and a water bath temperature of about 80° C. is used. Cooling for each sample is at an intermediate cooling rate, as is described in Example 1.

EXAMPLE 6

Co-crystallization of a 1:1 2,4-hexadiyn-1,6-bis (ethylurea)/2,4-hexadiyn-1,6-bis(propylurea) Mixture with Various Solvent Ratios Example 1 is repeated employing 0.1 g of 2,4-hexadiyn-1,6-bis(ethylurea), 0.1 g of 2,4-hexadiyn-1,6-bis(propylurea) and 1.8 g of glacial acetic acid in one vial, 0.2 g of 2,4- hexadiyn-1,6-bis(ethylurea), 0.2 g of 2,4-hexadiyn-1,6-bis (propylurea) and 1.6 g of glacial acetic acid in another vial, and 0.05 g of 2,4-hexadiyn-1,6-bis(ethylurea), 0.05 g of 2,4-hexadiyn-1,6-bis(propylurea) and 1.9 g of aqueous ethanol in a third vial in place of the weights of monomer and solvent stated in Example 1. Cooling for each sample is at an intermediate cooling rate using a water bath, as described in Example 1.

COMPARATIVE EXAMPLE A

Admixing a 2:1 2,4-hexadiyn-1,6-bis(ethylurea)/2,4-hexadiyn-1,6-bis(propylurea) Mixture For comparison, a 2:1 weight ratio of 2,4-hexadiyn-1,6-bis (ethylurea) and 2,4-hexadiyn-1,6-bis(propylurea) crystals is physically mixed, i.e. stirred or admixed together in a manner conserving the form of the individual crystals.

EXAMPLE 7

Polymerization 300 mg of 2,4-hexadiyn-1,6-bis(ethylurea) are slowly polymerized at 100° C. for 2 weeks. 300 mg of 2,4-hexadiyn-1,6-bis(propylurea) and a 2:1 weight ratio of a co-crystallized mixture of 2,4-hexadiyn-1,6-bis(ethylurea) and 2,4-hexadiyn-1,6-bis (propylurea) are heated at 160° C. for 23 hours. The completion of the polymerization process can be confirmed by X-ray powder diffraction according to Example 9 herein. Suitable ethylurea and propylurea diacetylenic monomers for use in this example are obtainable by fast quench crystallization from glacial acetic acid, for example as described in Preziosi U.S. Pat. No. 4,788,151.

Other suitable time-temperature conditions can be used to polymerize the monomers, with higher temperatures providing faster polymerization, as would be expected, provided that the temperature is not allowed to exceed the decomposition temperature of the diacetylenic monomer. 2,4-hexadiyn-1,6-bis (ethylurea) and a 2:1 co-crystallized mixture with 2,4-hexadiyn-,6-bis (propylurea) may begin to decompose above about 200° C. while 2,4-hexadiyn-1,6-bis (propylurea) alone may begin to decompose above about 220° C. Total conversion to polymer for $^{13}C$ NMR studies, or for other purposes, can be confirmed by powder X-ray diffraction or, using information provided by the present invention, by $^{13}C$ NMR studies themselves.

EXAMPLE 8

Powder Sample Preparation

To prepare powder samples suitable for further characterization, portions of the products of co-crystallization from Examples 1-5, and of the mixture of Comparative Example 6, are lightly ground for a few seconds in an agate mortar using a pestle. Liquid nitrogen can be employed to cool the crystals and facilitate grinding, if necessary, for example when the crystals are large and slippery. Using liquid nitrogen in this way can help reduce the influence of preferential orientation and promote random crystal cleavage during grinding, if necessary.

The resultant powder can be poured into plastic dishes to provide samples for color change determination or onto glass slides to provide samples for characterization by X-ray powder diffraction.

EXAMPLE 9

Color Development Determination

The following procedure is used to determine the relative color development reactivity at 60° C. of various ones of the samples of Example 8 and of a comparative sample of 2,4-hexadiyn-1,6-bis(ethylurea) as a control. The samples are supported on a white background at 60° C. in an oven equipped with a fluorescent lamp. The object lens of a digital camera is inserted into an opening in the top of the oven and a picture is taken every minute. The reactivity of each sample is also evaluated qualitatively by visually examining the color of each sample after predetermined time periods. The color change occurring with time is measured by measuring the red values on an RGB scale at a specific pixel on each sample using a graphical computer program, PixelGrabber (Java™ 2 Platform).

The optical density is obtained as the logarithm of the measured red value divided by the red value of the white background to the sample, to compensate for ambient light fluctuations. The color reactivity parameter obtained is described as being proportional to the change with time in the optical density determined. For example, the reactivity parameter can be defined as the slope of the curve of $-\log (R_{sample}/R_{white})$ versus time in minutes at the intersection with the respective curve of the standard. The color standard is a material with a suitable temperature independent optical density ("OD") value, for example a drawdown of a medium blue opaque ink on a white substrate having an OD value of 0.3.

EXAMPLE 10

Sample Characterization by X-Ray Powder Diffraction

X-ray diffraction data are collected for characterizing each sample using a Rigaku ULTIMA III (trademark) diffractometer, generating $CuK_{\alpha 1}$ radiation at a wavelength of 1.54056 Å.

Data are collected for values of $2\theta$ from 3° to 40° at a scanning rate of 0.04°/min with a step size of 0.02°. d-spacings for reflections are calculated using Bragg's law after collecting a pattern of each sample powder mixed with standard alumina for internal calibration. Some results obtainable are shown in the accompanying figures and are described elsewhere herein.

Table 2 shows some examples of quantitative results obtainable from a color development experiment such as is described in Example 9 using powdered crystal phase samples prepared by the methods of Examples 1 and 8. The weight proportion of 2,4-hexadiyn-1,6-bis(ethylurea) to 2,4-hexadiyn-1,6-bis(propylurea) in each sample is 2:1. Also set forth in Table 2 are some qualitative conclusions as to the color reactivity of the samples which can be drawn from analysis of X-ray powder diffraction spectra generated from an experiment such as is described in Example 10.

TABLE 2

Reactivities of 2:1 2,4-hexadiyn-1,6-bis (ethylurea):2,4-hexadiyn-1,6-bis (propylurea) Co-crystallized Diacetylenic Monomer Compositions

| Sample | Solvent | Monomer Weight | Cooling rate | PXRD fingerprint | Reactivity Par. 60° C. ($\Delta_{O.D.}$/min) |
|---|---|---|---|---|---|
| KX01 | Acetic Acid 100% | 2.5% | Petri (uncontrolled fast) | (LR) | — |
| KX02 | Acetic Acid 100% | 10% | Petri (uncontrolled intermediate) | (LR + HR) | 0.00189 |
| KX03 | Acetic Acid 100% | 10% | Vial (uncontrolled fast) | (LR) | 0.00095 |
| KX04 | Acetic Acid 100% | 10% | Petri (uncontrolled slow) | HR | 0.0035 |
| KX05 | Acetic Acid 100% | 10% | Petri (uncontrolled intermediate) | (LR + HR) | — |
| KX06 | Acetic Acid 100% | 2.5% | Vial (uncontrolled fast) | (LR) | — |
| KX08 | Ethanol 80% | 2.5% | Vial (uncontrolled intermediate) | LR | 0.00094 |
| KX12 | Ethanol 80% | 4% | Slow (short vacuum) | HR | 0.00305 |
| KX13 | Ethanol 80% | 4% | Fast | LR | 0.00046 |
| KX14 | Acetic Acid 100% | 10% | Fast | LR | 0.00135 |
| KX15 | Acetic Acid 100% | 10% | Slow | HR | 0.00413 |
| KX16 | Acetic Acid 100% | 10% | Intermediate | HR | 0.00377 |
| KX17 | Ethanol 80% | 4% | Fast | Undefined | 0.00145 |
| KX18 | Ethanol 80% | 4% | Intermediate | LR | 0.00144 |
| KX19 | Ethanol 80% | 4% | Slow (tall vacuum) | LR | 0.00148 |
| KX20 | Acetic Acid 100% | 10% | Fast | LR | 0.00113 |
| KX23 | Acetic Acid 100% | 10% | Slow | HR | 0.00459 |
| KX24 | Acetic Acid 100% | 10% | Intermediate | HR | 0.00621 |
| KX25 | Ethanol 80% | 4% | Slow (tall vacuum) | LR | 0.0021 |
| KX26 | Ethanol 80% | 4% | Slow (short vacuum) | undefined | 0.0033 |

Referring to Table 2, the samples tested are labeled with an alphanumeric identifier such as "KX01" in column 1. The solvent system, weight proportion of monomer and cooling rate, respectively, are described in the next three columns. The cooling conditions for samples KX01-KX06 were not well controlled. Rather, these samples were cooled in open vials or Petri dishes, on top of the hot plates used to heat the solutions, with the hot plates switched off.

Visually, fast and intermediate cooling yields relatively small, powdery, white or colorless crystals. In contrast, slow cooling of samples generally yields large crystals. Cooling in the tall vacuum flask yields needle-like crystals while extended cooling in the short vacuum flask yields plate-like crystals. Grinding in liquid nitrogen can be employed for large crystal samples such as KX12 and KX26 to obtain a powder with random crystallite orientations for characterization by X-ray powder diffraction, for example, as described in Example 8.

The next-to-last column in Table 2 describes the reactivity of the samples as can be determined from visual analysis of an X-ray powder diffraction pattern of the sample obtained by a method such as is described in Example 10. The various samples are classified as having either a low reactivity "LR" or a relatively high reactivity "HR". Characteristic features of the X-ray powder diffraction pattern which appear to be associated with a relatively higher reactivity, for example the presence of three or more particular reflection peaks in a fingerprint region of the X-ray powder diffraction pattern, are described herein in connection with the drawings.

The last column in Table 2 describes the color development reactivity of the samples as may be determined from a method such as is described in Example 9. As stated, the color development reactivity is measured as the change in color with time at 60° C.

Those samples of crystalline phases that exhibit a color development reactivity greater than 0.003 ΔOD/min. are considered to have a high reactivity. Crystalline phase samples with values in the range of from 0.0005 ΔOD/min. to 0.002 ΔOD/min are considered to have low reactivity.

Using these criteria, samples KX04, KX12, KX15, KX16, KX23 and KX24 are found to have a high color development reactivity. In contrast, samples KX08, KX13, KX14, KX17, KX18, KX19, KX20, KX25 and KX26 are found to have a low color development reactivity. As can be seen from Table 2, by variation of the sample crystallization conditions and other parameters of diacetylenic monomer compositions, a diversity of reactivities can be provided from which an indicator formulator can make a selection for use with a particular host product.

By comparing the color development values in the last column of Table 2 with the figures in the next to last column, a good correlation between the reactivities determined by color development studies and those determined from X-ray powder diffraction spectra can be seen.

All the samples in Table 2 that are identified by their X-ray powder diffraction spectra as potentially having a high reactivity meet the criterion for high color development reactivity. And all samples identified by their X-ray powder diffraction spectra as potentially having a low reactivity are found to have a low color development reactivity. Two samples crystallized from aqueous ethanol, samples KX17 and KX26, yield undefined fingerprint diffraction spectra, referring here to the region of the X-ray powder diffraction spectra between a d spacing of about 4.28 Å and a d spacing of about 3.81 Å. This may be because aqueous ethanol samples sometimes yield diffraction peaks of rather low intensity in the fingerprint region of the diffraction spectrum. Also, in the case of KX26 the preferential orientation of the sample in large plate-like crystals may affect the fingerprint region intensities.

The color development reactivities also correlate well with the crystallization parameters employed. The samples crystallized from acetic acid under slow or intermediate cooling conditions, including sample KX04 where the cooling conditions were not well controlled, all have high color development reactivity, pursuant to the criteria described herein. In contrast, the acetic acid samples crystallized under fast cooling conditions exhibit low reactivity.

Sample phases crystallized from aqueous ethanol are generally less reactive than the corresponding products crystallized from acetic acid. Thus, the crystallization solvent system is one of the crystallization parameters that can be used to control the reactivity of the co-crystallized product.

As the data in Table 2 suggests, with regard to the aqueous ethanol samples, the color development reactivity can also be controlled by monomer concentration.

Aqueous ethanol crystallized samples also exhibit reactivity increases as cooling rates are reduced. Thus, the sequence of samples with slower cooling rates through samples KX17, KX18, KX25 and KX26 exhibits increasing reactivity, with the slowest cooled sample, KX26, exhibiting high reactivity according to the criteria herein.

Accordingly, it appears from the data in Table 2 that the X-ray powder diffraction pattern of a co-crystallized 2,4-hexadiyn-1,6-bis(ethylurea)/2,4-hexadiyn-1,6-bis (propylurea) composition is associated with the color development reactivity and can be used to identify samples of the composition by reactivity, if desired.

Figures 11A, 11B, 11C:
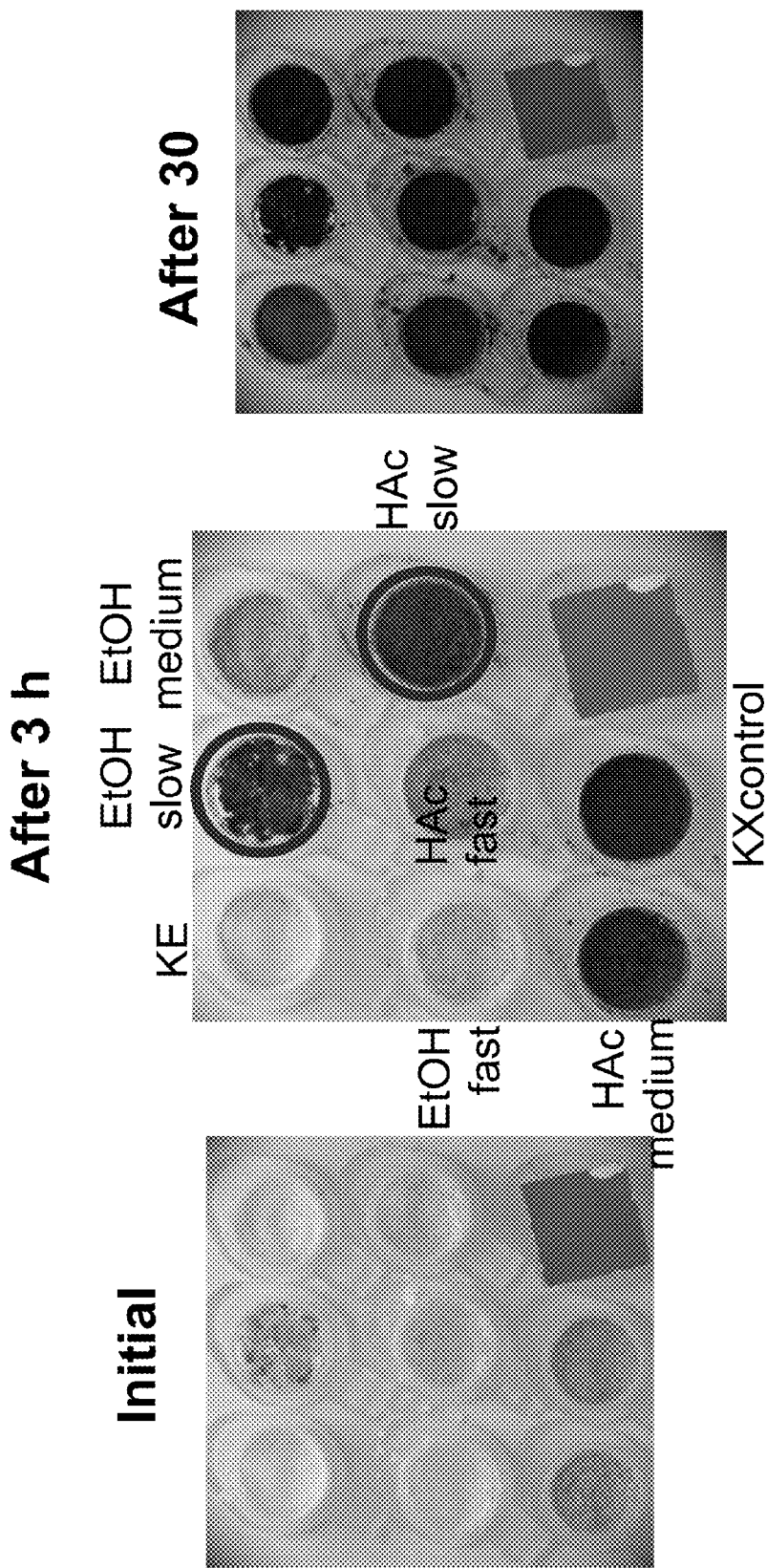
FIGS. 11A, 11B and 11C illustrate the effect, at different times, that crystallization parameters can have on color development in six different samples of co-crystallized 2,4-hexadiyn-1,6-bis(ethylurea)/2,4-hexadiyn-1,6-bis (propylurea) compositions.

Some of the results in Table 2 are also shown graphically in FIGS. 11A, 11B and 11C as is further described elsewhere herein.

Table 3 below shows data for some data additional co-crystallized 2,4-hexadiyn-1,6-bis(ethylurea)/2,4-hexadiyn-1,6-bis(propylurea) samples labeled KU01, KU03, KU08, KU09, KU14, KU10 and KU15 to KU17 and KU19 to KU22, respectively.

Figure 10D:
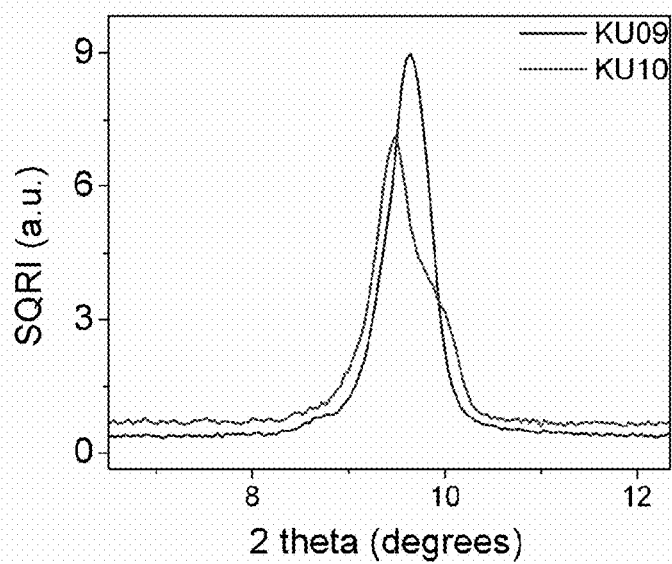
FIG. 10D shows, for comparison, an overlay of an individual reflection peak from one sample on the corresponding peak from another sample.

A parameter listed in Table 3, but not shown in Table 2, is the number of phases present in the resulting product. This number is determined from the shape of the 002 reflection, the second lowest angle reflection, of a powder X-ray diffraction pattern for the respective sample. Where the 002 reflection is a singlet peak, as shown in FIG. 10B or FIG. 10C, a single phase is indicated. Where the 002 reflection exhibits a split peak or a shoulder, two phases are indicated. In the case of KU09, where a single phase is suggested by the 002 reflection. However, the possible presence of two phases, a high reactivity phase and a low reactivity phase, is suggested by the fingerprint region of the diffraction pattern, and appears to be confirmed by the color development study. These phenomena are further described herein in relation to FIGS. 10B and 10C.

EXAMPLE 11

Sample Characterization by NMR Spectroscopy

Solid-state NMR spectroscopy is performed on 50-80 mg samples of selected ones of the products of Examples 1-7 to further characterize the products. $^{13}C$ cross polarization magic-angle-spinning ("CPMAS") NMR spectra are col-

TABLE 3

Additional Reactivities of Co-crystallized Diacetylenic Monomer Compositions

| Sample | Solvent | Monomer Weight | Cooling rate | Phases | PXRD fingerprint | Reactivity Par. 60° C. ($\Delta_{O.D.}$/min) |
|---|---|---|---|---|---|---|
| KU01 | Acetic Acid 100% | 10% | Intermediate | 1 | LR | 0.002 |
| KU03 | Acetic Acid 100% | 10% | Fast | 2 |  | 0.0042 |
| KU08 | Ethanol 80% | 5% | Slow(dewar) | 2 |  | 0.0033 |
|  |  |  |  |  |  | 0.0002 |
| KU09 | Ethanol 80% | 5% | Intermediate | 1 | HR | 0.0039 |
|  |  |  |  |  | LR | 0.0003 |
| KU10 | Ethanol 80% | 5% | Fast | 1 + sh | LR | 0.0014 |
|  |  |  |  |  |  | 0.0005 |
| KU14 | Acetic Acid 100% | 10% | Slow (dewar) | 2 | HR | 0.0031 |
|  |  |  |  |  | LR | 0.0004 |
| KU15 | Acetic Acid 100% | 10% | Intermediate | 2 | LR+ | 0.00104 |
| KU16 | Acetic Acid 100% | 10% | Intermediate | 1 | HR | 0.00279 |
| KU17 | Acetic Acid 100% | 10% | Intermediate | 1 | HR | 0.00439 |
| KU19 | Acetic Acid 100% | 10% | Intermediate | 1 | HR | 0.00475 |
| KU20 | Acetic Acid 100% | 10% | Intermediate | 1 | HR | 0.00278 |
| KU21 | Acetic Acid 100% | 10% | Intermediate | 1 | HR | 0.00285 |
| KU22 | Acetic Acid 100% | 10% | Intermediate | 2 | HR | 0.00368 |

Table 3 shows further examples of quantitative results obtainable from a color development experiment such as is described in Example 9 using powdered crystal phase samples prepared by the methods of Examples 3 and 8. The weight proportion of 2,4-hexadiyn-1,6-bis(ethylurea) to 2,4-hexadiyn-1,6-bis(propylurea) in each sample is 1:1. Also set forth in Table 3 are some qualitative conclusions as to the color reactivity of the samples which can be drawn from analysis of X-ray powder diffraction spectra generated from an experiment such as is described in Example 10. The experimental conditions and data shown in Table 3 are to be understood in a similar manner to those shown in Table 2.

The Table 3 data illustrates a further diversity of color-changing reactivities that can be provided by variation of the sample crystallization conditions and other parameters of diacetylenic monomer compositions, and from which an indicator formulator can select a composition for use with a particular host product.

Figure 10A:
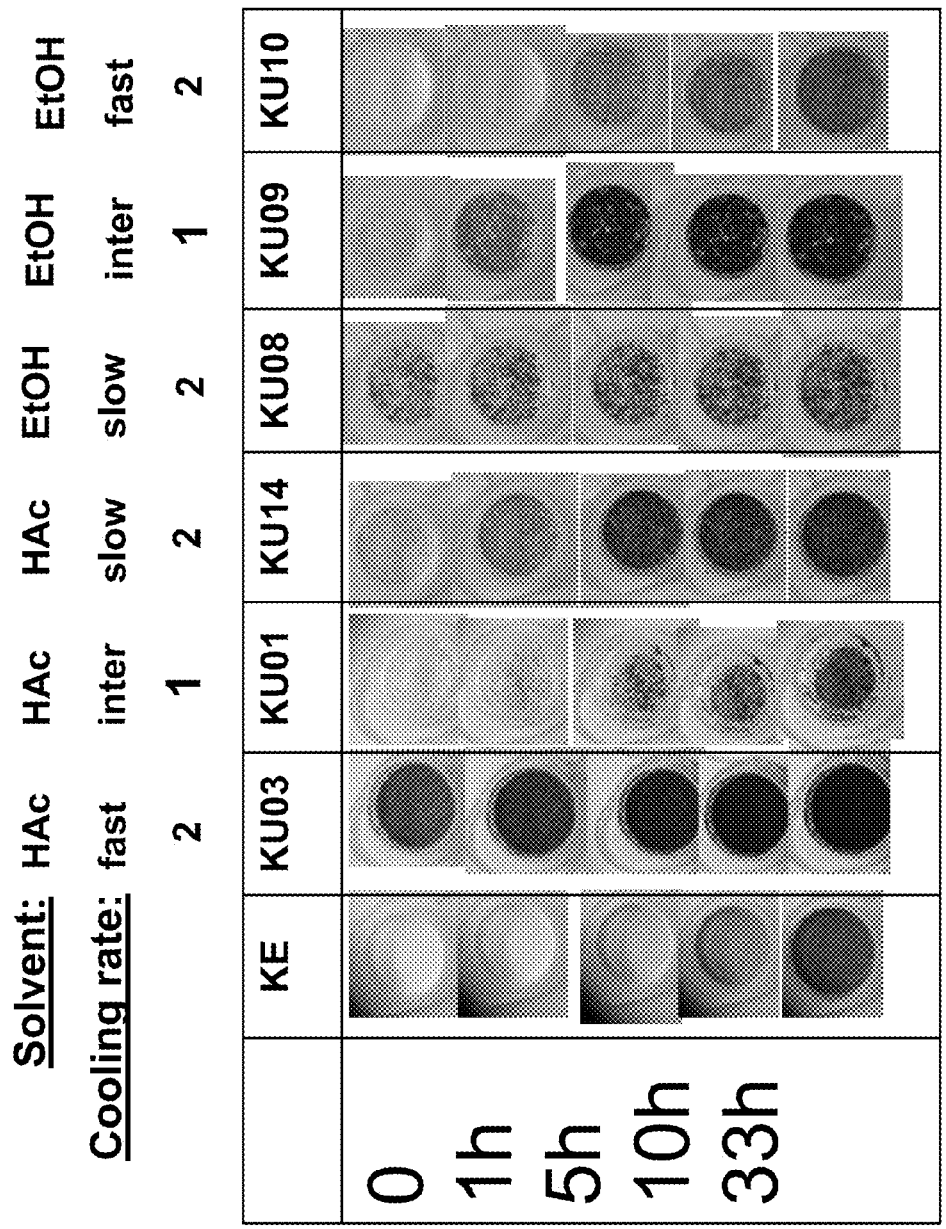
FIG. 10A illustrates the effect that cooling rate during crystallization can have on color evolution in various samples of co-crystallized compositions of 1:1 by weight 2,4-hexadiyn-1,6-bis(ethylurea)/2,4-hexadiyn-1,6-bis(propylurea)
Figure 10B:
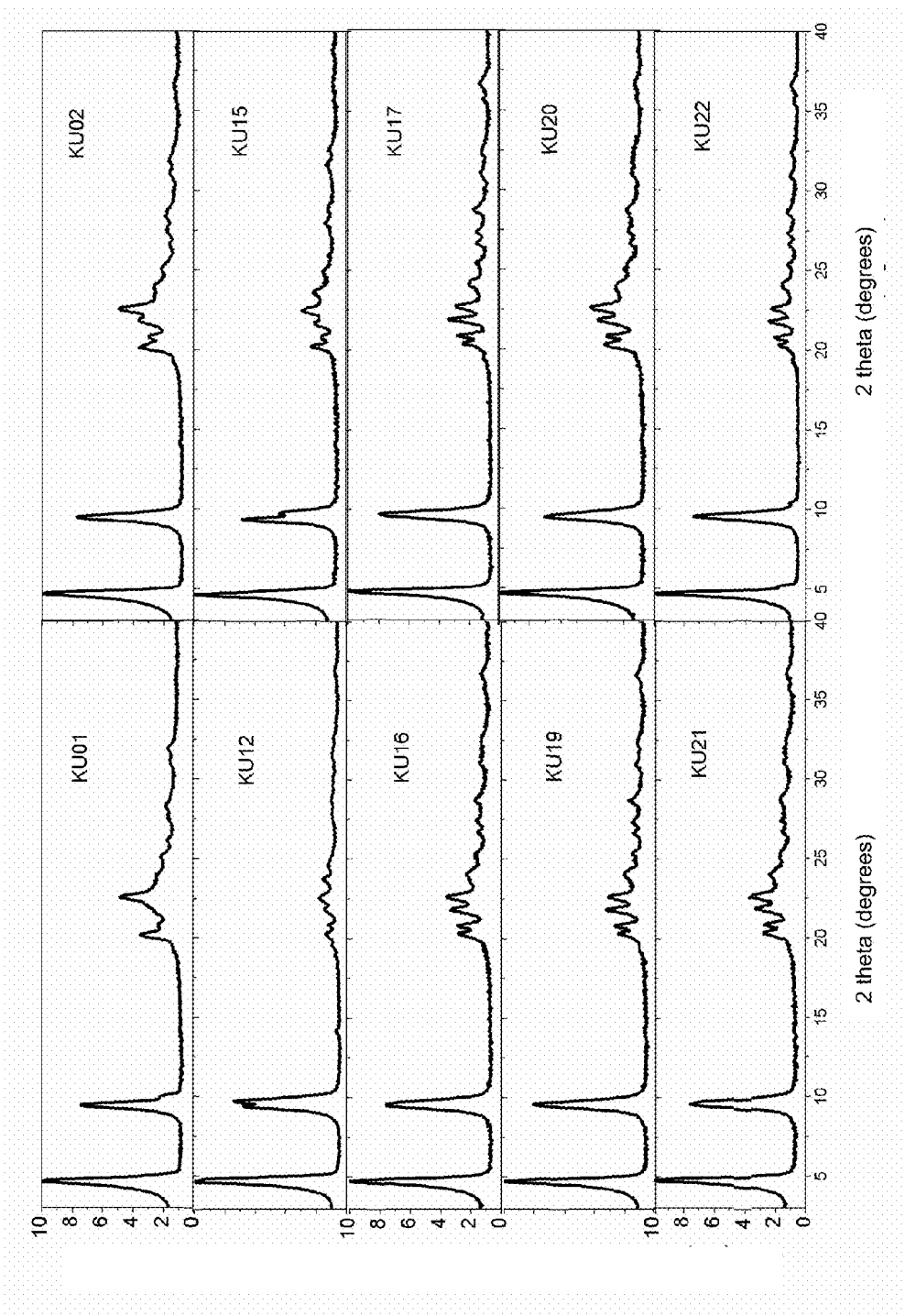
FIGS. 10B and 10C show powder X-ray diffraction patterns of the samples for which color evolution data are shown in FIG. 10A and of some additional samples of 1:1 by weight co-crystallized mixtures of 2,4-hexadiyn-1,6-bis(ethylurea) and 2,4-hexadiyn-1,6-bis(propylurea)
Figure 10C:
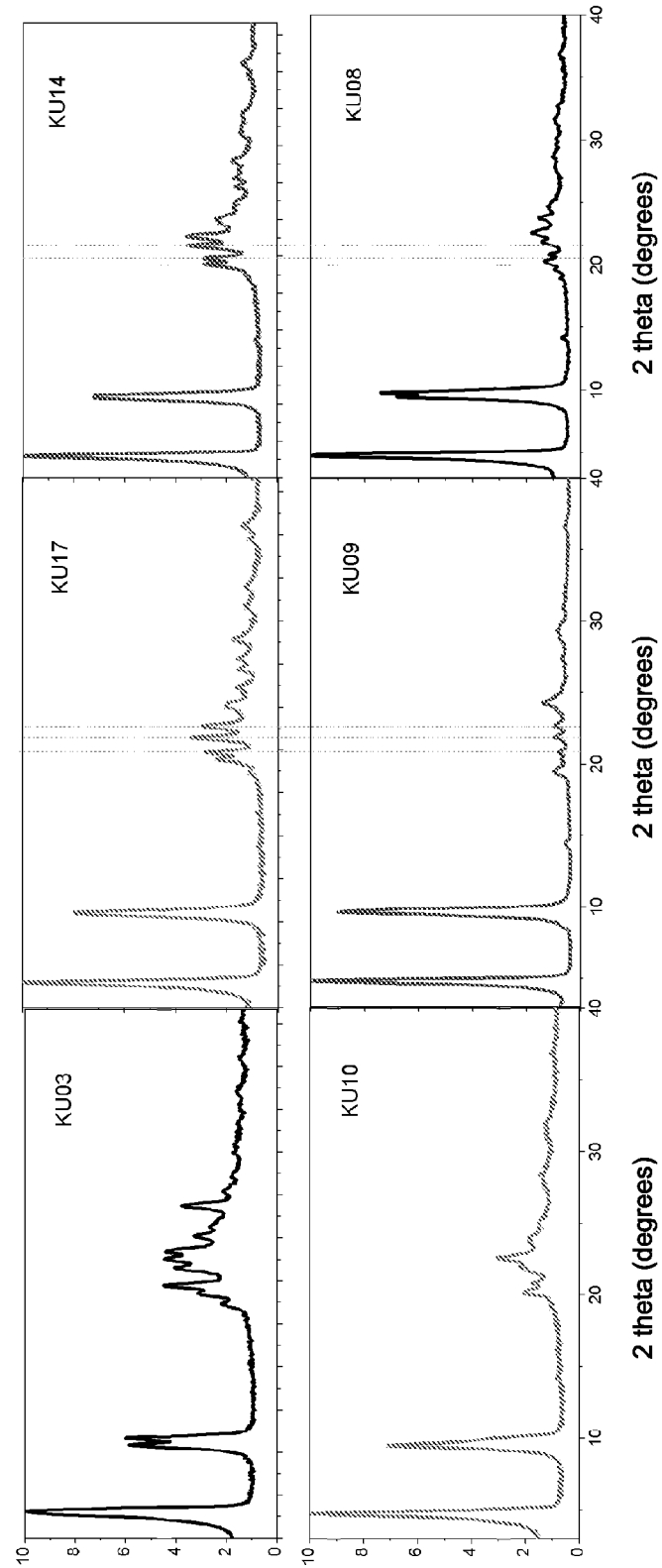

Some of the results in Table 3 are also shown graphically in FIG. 10A, and X-ray powder diffractograms of some of the samples described in Table 3 are shown in FIGS. 10B and 10C as is further described elsewhere herein.

lected using a DSX-500 spectrometer (Bruker Corporation) operating at 125.4 MHz for the $^{13}C$ nucleus, and using a Bruker 4 mm CPMAS probe. Two different contact times are used, namely 100 μs and 1 ms. Different spinning speeds are employed to identify the isotropic $^{13}C$ peaks among a number of resonance lines. For example, spinning speeds of 7.3 kHz, 8 kHz and 9.7 kHz can be employed for the KX monomer and 8 kHz and 10 kHz can be used for each contact time for all other samples. The chemical shifts are referenced externally to tetramethylsilane.

Changing the cross-polarization contact time from 100 μs to 1 ms can reveal whether the carbon peaks are strongly coupled to surrounding hydrogen atoms. Those $^{13}C$ peaks showing large growth after increasing the contact time are probably bearing no C—H direct bonds, like the carbonyl carbon at 160 ppm, or the sp and sp2 carbons at 77 and 66 ppm.

Figure 20:
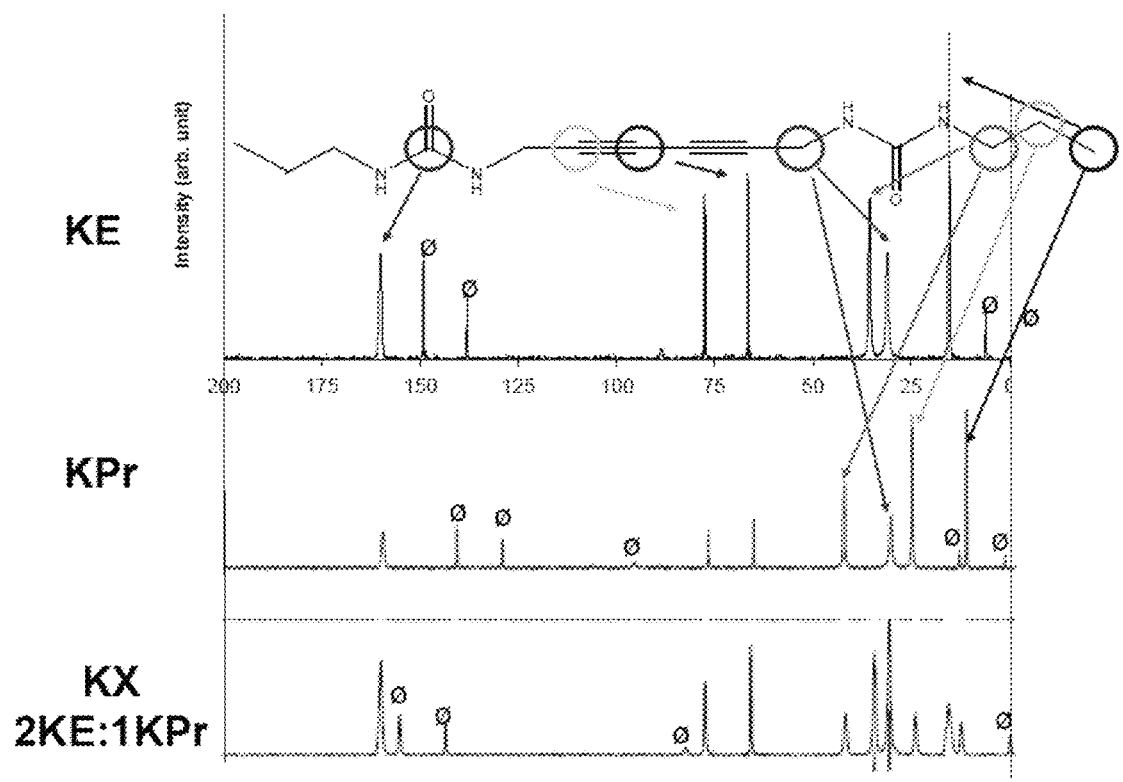
FIG. 20 is a graphical depiction of $^{13}C$ NMR spectroscopy data from which the data relating to diacetylenic monomers appearing in Table 5 (in FIG. 19) can be calculated.
Figure 21:
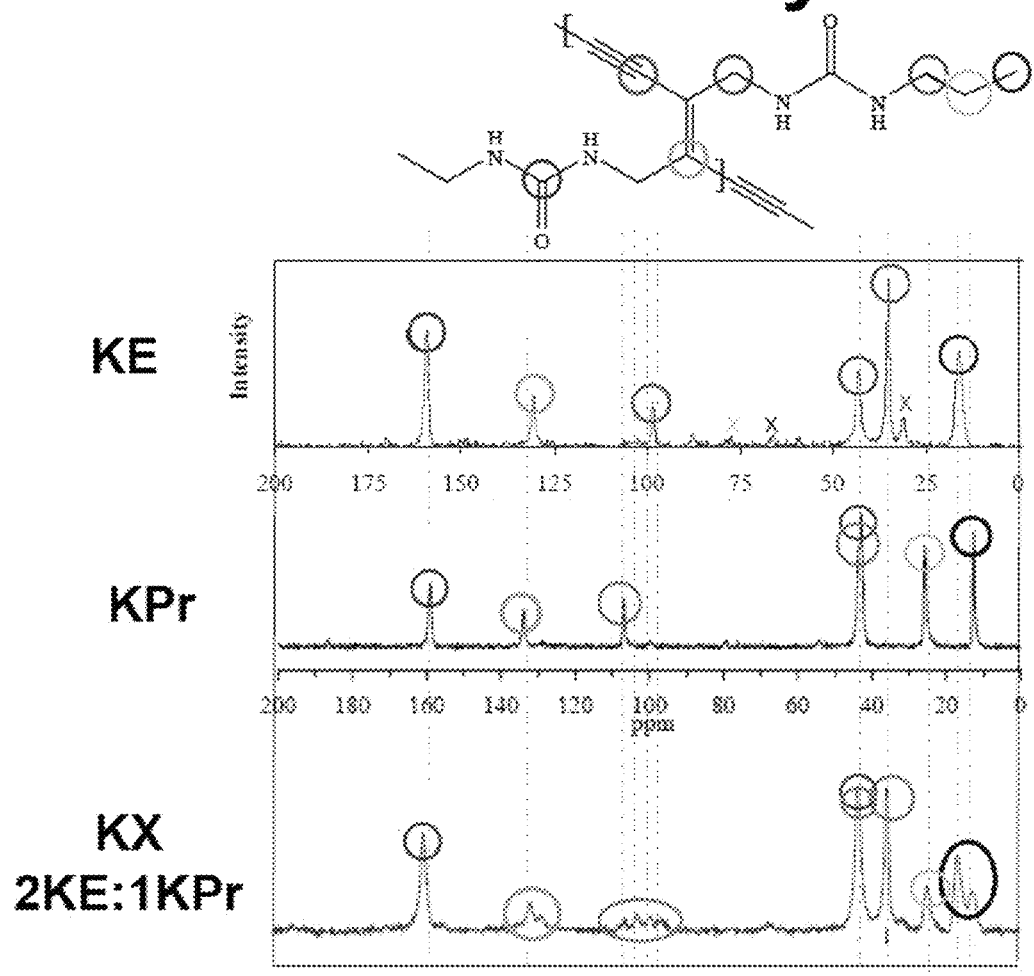
FIG. 21 is a graphical depiction of $^{13}C$ NMR spectroscopy data from which the data relating to diacetylenic polymer appearing in Table 5 (in FIG. 19) can be calculated.

Some results obtainable with characterization by X-ray powder diffraction pursuant to Example 10 are shown in FIGS. 1-7 and 13-15. Some further results obtainable with characterization by NMR spectroscopy pursuant to Example 11 are shown in FIGS. 19-21. These results are discussed below.

Referring to FIG. 1, the upper X-ray diffraction pattern shown is an example of data obtainable by characterization of a 2:1 weight-based physical admixture of 2,4-hexadiyn-1,6-bis(ethylurea) and 2,4-hexadiyn-1,6-bis(propylurea) produced by the method of Comparative Example A. The 2θ diffraction angles are plotted along the abscissa in degrees and signal intensity is plotted on the ordinate in arbitrary units.

The lower X-ray diffraction pattern is an example of data obtainable by characterization of a co-crystallized 2:1 weight-based mixture of 2,4-hexadiyn-1,6-bis(ethylurea) and 2,4-hexadiyn-1,6-bis(propylurea) produced by the method of Example 1. The co-crystallization method employs acetic acid as solvent and slow cooling, using a vacuum flask, as described in Example 1.

The X-ray diffraction patterns in FIG. 1 exhibit three angular regions of interest which are labeled (1), (2) and (3) at the top of the figure. The diffraction patterns suggest that the co-crystallized material comprises a unique phase exhibiting different reflections corresponding to a crystal with lattice parameters different from the lattice parameters of either of the starting products.

Comparison of the upper and lower X-ray diffraction patterns appearing in FIG. 1 shows that the physical mixture yields a doublet peak at about 4-6°, region (1), which, for the co-crystallized material, is replaced by a sharp single first order peak almost at 5°. A similar result is observable at region (2) where, the physical mixture yields another doublet peak at about 8-11°, and the co-crystallized material yields a sharp single first order peak almost at 10°. Furthermore, less intense peaks are present at about 13° and 16° in the upper pattern and can be associated with 2,4-hexadiyn-1,6-bis(propylurea) and 2,4-hexadiyn-1,6-bis(ethylurea) respectively by reference to diffraction patterns for the individual monomers (not shown). These small peaks are not present in the co-crystallized, lower pattern or diffractogram.

Desirably, the first two reflections exhibited in the X-ray powder diffraction pattern of a co-crystallized diacetylenic composition such as is shown in the lower half of FIG. 1, at the lowest 2θ angles, are essentially singlet peaks. Each singlet peak can have a unique cusp with no pronounced shoulder projecting from either side of the peak. Desirably also no additional peak is present within a 2θ range of 3° above or below either of the two low angle reflection peaks. Furthermore, the diffraction pattern usefully can be free of any additional peak between the first two reflections. Also, the diffraction pattern can be free of any additional peak at a 2θ angle below 16°.

Singlet peaks are generally essentially symmetrical. Shoulders whose presence indicates that a peak is not a singlet can often be well defined second peaks or corners but in some instances may be subtle, gently sloping asymmetries or bulges. The plot line or curve outlining a peak can comprise one or two points or zones of inflexion indicating the presence of a shoulder and that the peak is accordingly not likely to be regarded as a singlet peak pursuant to the invention.

With regard to positioning of the reflection peaks in the diffraction pattern, the lowest angle reflection peak can be at a 2θ angle corresponding with a $\bar{d}$ spacing in the range of from about 16.4 Å and about 20.1 Å. The second lowest angle reflection peak can be at a 2θ angle corresponding with a $\bar{d}$ spacing in the range of from about 8.2 Å to about 10 Å. For example, the lowest angle reflection peak can correspond with a $\bar{d}$ spacing in the range of from about 17.3 Å to about 18.3 Å and the second lowest angle reflection peak can correspond with a $\bar{d}$ spacing in the range of from about 8.6 Å to about 9.2 Å.

In general, but without limitation, the lowest angle and second lowest angle reflections can have an intensity which is at least three times greater than background, for example at least five times greater than background or at least ten times greater than background, or which has any other suitable value.

The data shown in the upper diffractogram of FIG. 1 can be understood as representing separate contributions from individual crystals of 2,4-hexadiyn-1,6-bis (ethylurea) and 2,4-hexadiyn-1,6-bis(propylurea) in the mixture. The data shown in the lower pattern of FIG. 1 are consistent with the interpretation that crystals of the co-crystallized mixture are, or comprise, a solid solution of 2,4-hexadiyn-1,6-bis (ethylurea) and 2,4-hexadiyn-1,6-bis(propylurea) having homogenous continuous phase crystals in which the two compounds are present in approximately the proportions in which they are co-crystallized.

Figure 2:
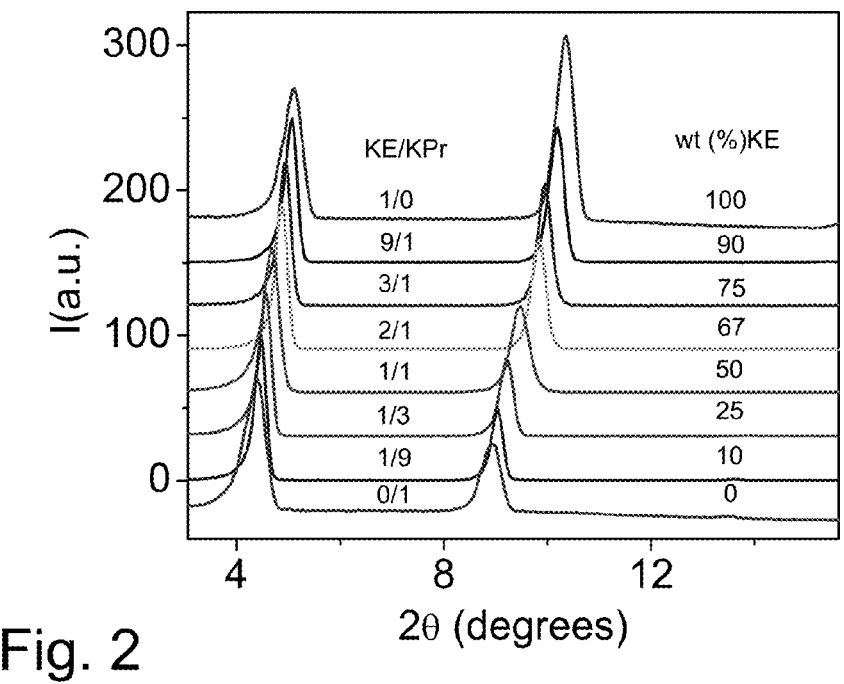
FIG. 2 shows a set of X-ray powder diffraction patterns for various co-crystallized mixtures of monomers in different ratios, for a limited range of 2θ angles.

FIG. 2 shows a set of eight X-ray diffraction patterns which are examples of data obtainable by characterization of the products of Example 4. These products comprise eight different ratios of 2,4-hexadiyn-1,6-bis(ethylurea) to 2,4-hexadiyn-1,6-bis(propylurea), crystallized from 10 percent solutions in acetic acid, with intermediate cooling. The products corresponding with the first and last ratios of 2,4-hexadiyn-1,6-bis(ethylurea) to 2,4-hexadiyn-1,6-bis(propylurea) are the monomers alone.

A limited range of 2θ diffraction angles of interest, from about 3° to about 16° is shown along the abscissa in FIG. 2 and signal intensity is plotted on the ordinate in arbitrary units. The molar ratios of 2,4-hexadiyn-1,6-bis(ethylurea) to 2,4-hexadiyn-1,6-bis(propylurea) employed are shown in the lefthand column in FIG. 2, labeled "2,4-hexadiyn-1,6-bis (ethylurea)/2,4-hexadiyn-1,6-bis(propylurea)", and the corresponding weight proportion of 2,4-hexadiyn-1,6-bis(ethylurea), labeled "2,4-hexadiyn-1,6-bis(ethylurea)", is shown in the righthand column.

As can be seen, two well-defined singlet peaks are exhibited by each of the eight products. Also, the relative intensity of the second to the first reflection increases with increasing concentration of 2,4-hexadiyn-1,6-bis(ethylurea). And the angles at which the singlet peaks occur increase slightly, or shift to higher angles with increasing concentration of 2,4-hexadiyn-1,6-bis(ethylurea).

The results shown in FIG. 2 are believed to be consistent with single-phase-like behavior over the entire range of compositions of the co-crystallized mixtures. Thus, it appears that, under the experimental conditions described, co-crystallized 2,4-hexadiyn-1,6-bis(ethylurea) and 2,4-hexadiyn-1,6-bis(propylurea) may comprise a solid solution throughout most, if not all, of the composition range.

Figure 3:
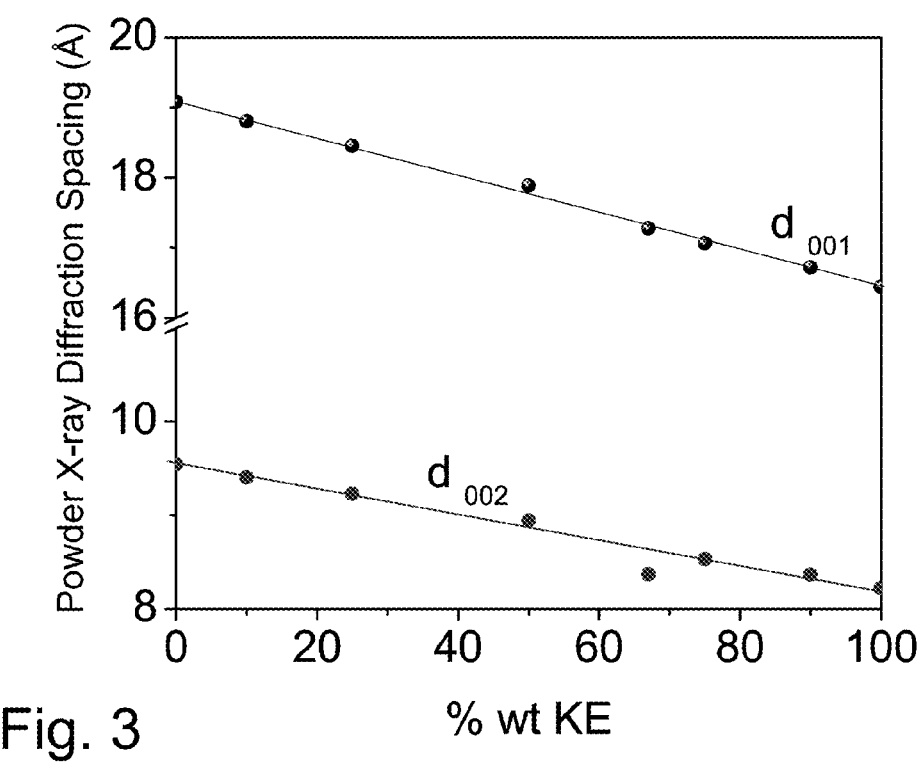
FIG. 3 shows the variation of X-ray diffraction d-spacing with concentration that can be calculated from the data illustrated graphically in FIG. 2.

FIG. 3 depicts some of the data shown in FIG. 2 in a different form. The graph shown in FIG. 3 can be calculated from the data supporting the FIG. 2 graphs using Bragg's law. More specifically, FIG. 3 plots the variation, with the weight percent of 2,4-hexadiyn-1,6-bis(ethylurea) in the co-crystallized mixture, of the two longest X-ray powder diffraction spacings, designated $d_{001}$ and $d_{002}$, as calculated from the angles of the corresponding lowest angle intensity peaks shown in FIG. 2. Close approximations to a straight line relationship with the percent of 2,4-hexadiyn-1,6-bis(ethylurea) are exhibited by both $d_{001}$ and $d_{002}$.

Surprisingly, FIGS. 2 and 3 show that each of the d-spacings, $d_{001}$ and $d_{002}$, varies inversely with an increasing weight proportion of 2,4-hexadiyn-1,6-bis(ethylurea) in the mixture of 2,4-hexadiyn-1,6-bis(ethylurea) and 2,4-hexadiyn-1,6-bis (propylurea) examined. This information can be used to modify the d-spacing in crystals of a mixture of 2,4-hexadiyn-1,6-bis(ethylurea) and 2,4-hexadiyn-1,6-bis (propylurea) or to provide crystals of a mixture of 2,4-hexadiyn-1,6-bis(ethylurea) and 2,4-hexadiyn-1,6-bis(propylurea) having a desired d-spacing, within limits, by appropriate selection of the relative proportions of 2,4-hexadiyn-1,6-bis(ethylurea) and 2,4-hexadiyn-1,6-bis(propylurea).

Figure 4:
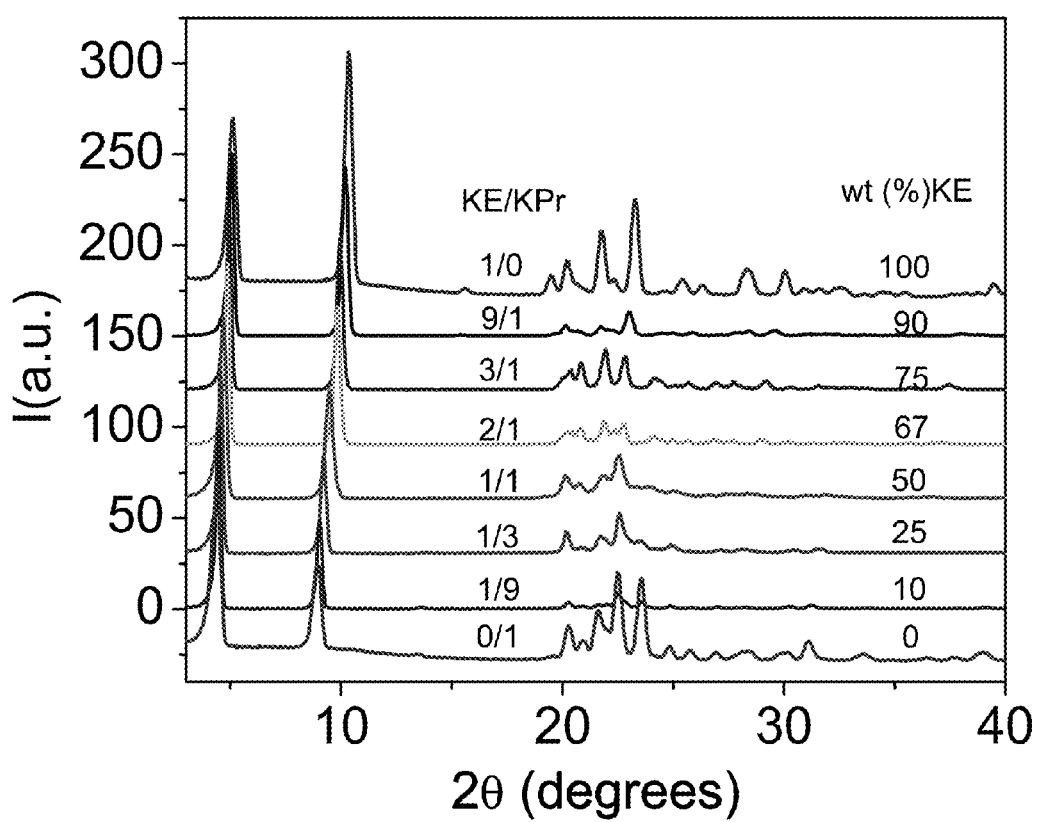
FIG. 4 shows a set of X-ray diffraction patterns similar to those shown in FIG. 2 for a wider range of 2θ angles.

FIG. 4 is a view similar to FIG. 2 showing the same X-ray diffraction intensity pattern over a more extensive range of diffraction angles than are shown in FIG. 2, namely from about 3° to about 40°. Referring to FIG. 2, low intensity peaks for 2,4-hexadiyn-1,6-bis(propylurea) (bottom graph) that appear in the range of from about 20° to about 25° can be seen to be approximately neutralized by a small percentage of 2,4-hexadiyn-1,6-bis(ethylurea) in the co-crystallized mixture. The low intensity peaks for 2,4-hexadiyn-1,6-bis(ethylurea) in the same range, which are slightly displaced in diffraction angle from the 2,4-hexadiyn-1,6-bis(propylurea) peaks, slowly emerge as the concentration of 2,4-hexadiyn-1,6-bis(ethylurea) increases.

Figures 5A, 5B:
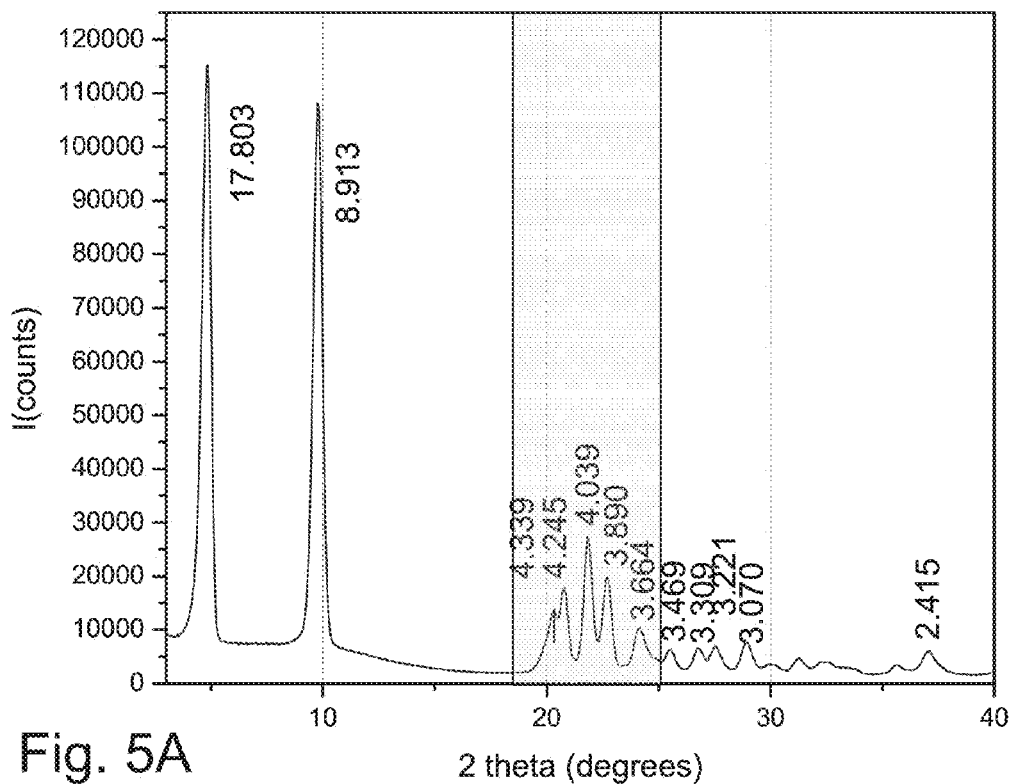
FIG. 5A shows an X-ray powder diffraction pattern obtainable by characterization of a highly reactive co-crystallized mixture of diacetylenic monomers, on which $\underline{d}$ spacings for various diffraction peaks of interest have been indicated numerically.

FIG. 5A shows a diffraction pattern obtainable for a highly reactive 2:1 weight ratio mixture of 2,4-hexadiyn-1,6-bis (propylurea) with 2,4-hexadiyn-1,6-bis(ethylurea) co-crystallized from acetic acid at a slow cooling rate pursuant to a method such as is described in Example 1.

The method of Example 10 can be used to generate the diffraction pattern shown.

Referring to FIG. 5A, intensity data is shown on the y-scale for 2θ angles in the range of from about 3° to 40°, as shown on the x-scale.

FIG. 5B shows a table, Table 4, which lists d-spacings, in angstrom units, which correspond to the peaks shown in FIG. 5A, along with the 2θ angles at which the peaks occur. The d-spacings can be calculated, using Bragg's law from the 2θ angles at which the peaks are observed, and vice versa. These 2θ angles are also marked on FIG. 5A in the vicinity of the respective peaks. As is generally understood, a d-spacing is the spacing between parallel planes of atoms in the crystal lattice.

Table 4 also includes a column of peak intensities, normalized to 1000 arbitrary units for the highest peak, which occurs at a Bragg 2θ angle of about 4.9°, to facilitate comparison of peak intensities, one with another.

A fingerprint region of 2θ angles in the range of from about 19° to about 25°, where significant differences between co-crystallized mixtures of 2,4-hexadiyn-1,6-bis (ethylurea) and 2,4-hexadiyn-1,6-bis(propylurea) of different reactivities can be observed, is marked with a box in the middle of each of FIGS. 5A and 5B.

Within the boxed fingerprint region, three distinct peaks can be observed at 2θ angles corresponding with d-spacings of 3.664, 3.890 and 4.039 Å. Optical color development tests suggest this fingerprint pattern of diffraction peaks can be associated with co-crystallized 2,4-hexadiyn-1,6-bis(ethylurea)/2,4-hexadiyn-1,6-bis(propylurea) products exhibiting relatively high thermal reactivities. The patterns shown in FIG. 6, and elsewhere herein, further exemplify that a distinctive fingerprint pattern of diffraction peaks may be exhibited by co-crystallized 2,4-hexadiyn-1,6-bis(ethylurea)/2,4-hexadiyn-1,6-bis(propylurea) products which have high color development reactivity.

Figure 6:
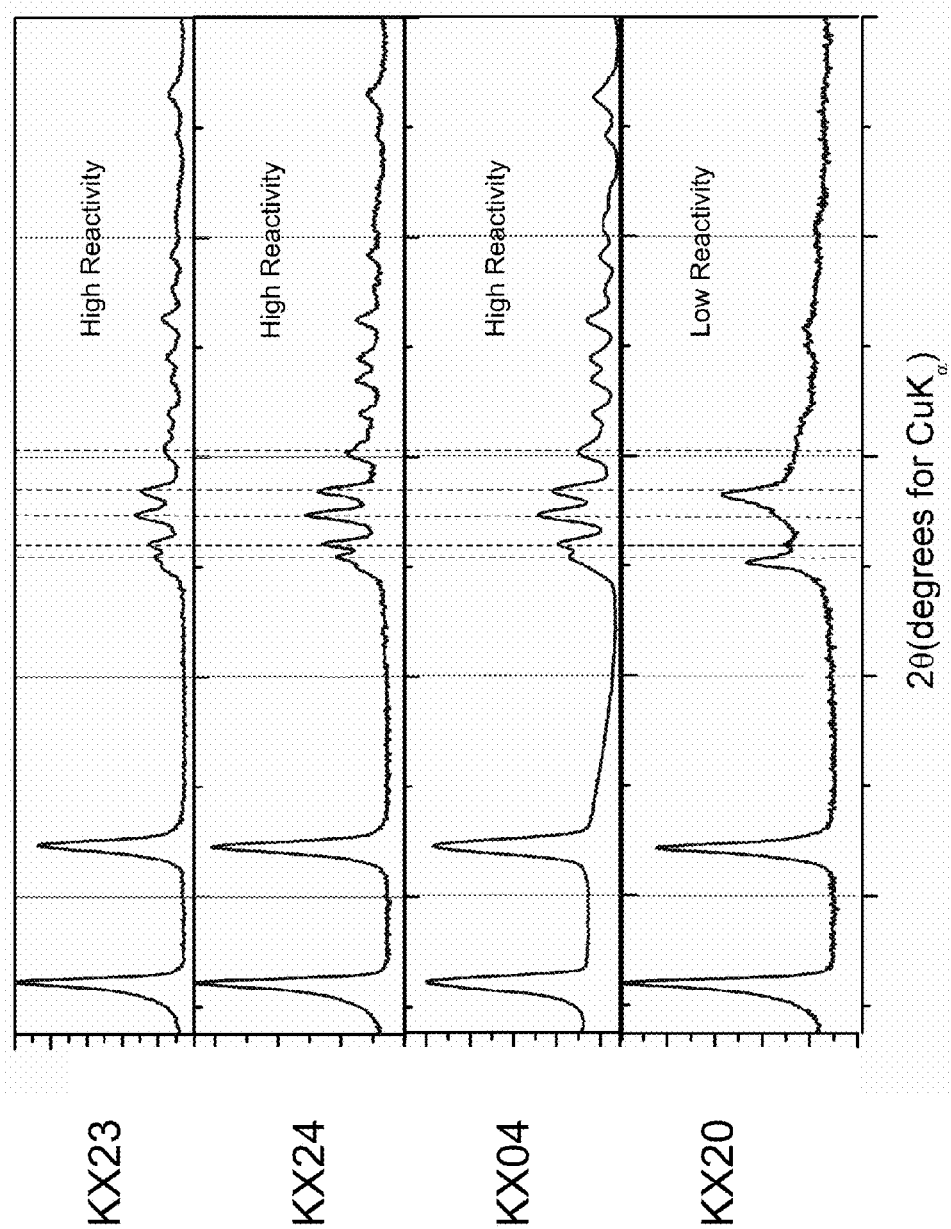
FIG. 6 shows X-ray powder diffraction patterns for a number of samples of diacetylenic monomer compositions crystallized from acetic acid, in which diffractrogams certain diffraction characteristics associated with high color-change reactivity are apparent.

FIG. 6 shows X-ray powder diffraction patterns for four of the diacetylenic monomer compositions prepared by the method of Example 1 and for which various characteristic data are shown in Table 2, namely samples KX04, KX20, KX22 and KX24. All four samples are prepared from a 2:1 proportion of 2,4-hexadiyn-1,6-bis (ethylurea) to 2,4-hexadiyn-1,6-bis(propylurea) and all are co-crystallized from acetic acid at different cooling rates. Sample KX04 is prepared by uncontrolled slow cooling, sample KX20 by fast cooling, sample KX23 by (controlled) slow cooling, and sample KX24 by intermediate cooling. Crystal samples are prepared by the method of Example 8 and X-ray powder diffraction patterns are obtained by the method of Example 10.

The color development tests described in Example 9, with possible results shown in Table 2 indicate that samples KX04 (uncontrolled slow), KX23 (intermediate) and KX 24 (slow) can all exhibit high color development reactivity in response to thermal stimulus.

In FIG. 6, 2θ angles are plotted on the x-axis which has markers at 5° intervals and the scale (not marked) ranges from 4° to 40°. Intensity is plotted on the y-axis in arbitrary units.

Referring to FIG. 6, all four samples can be seen to exhibit well-defined, relatively high intensity singlet peaks at lowest 2θ angles of about 5° and about 10° and another series of peaks in the fingerprint region of about 19° to about 25°. Vertical broken lines in this region indicate 2θ angles at which characteristic peaks may occur.

The spectra shown in FIG. 6 for high reactivity samples KX04, KX23 and KX24 all share a number of distinctive peaks which together can be referenced as a fingerprint for high reactivity, which fingerprint is not shared by the spectrum for the low reactivity sample KX20.

For example, each of the spectra for samples KX04, KX23 and KX24 exhibits a peaks d spacings of 4.24, 4.04 and 3.89 Å (the three central broken lines). In contrast, the lowermost spectrum for sample KX20 lacking a peak in the vicinity of 4.04 Å does not show the fingerprint associated with high reactivity. Also, the peak near 3.89 Å lacks the shape and positioning of the corresponding peaks exhibited by the high reactivity samples.

Furthermore, samples KX04, KX23 and KX24 exhibit a peak at a d spacing of 4.34 Å (lefthand broken line) which is merely nascent in the spectrum of low reactivity sample KX20, and another peak at 3.66 Å (righthand broken line) which is not exhibited by low reactivity sample KX20.

The fingerprint d spacings of the high reactivity phase can also be expressed as fractional numbers with respect to the d-spacing of the first reflection, as being at 1, 0.98-0.97, 0.93, 0.89 and 0.85-0.84 times 4.34 Å.

Figure 7:
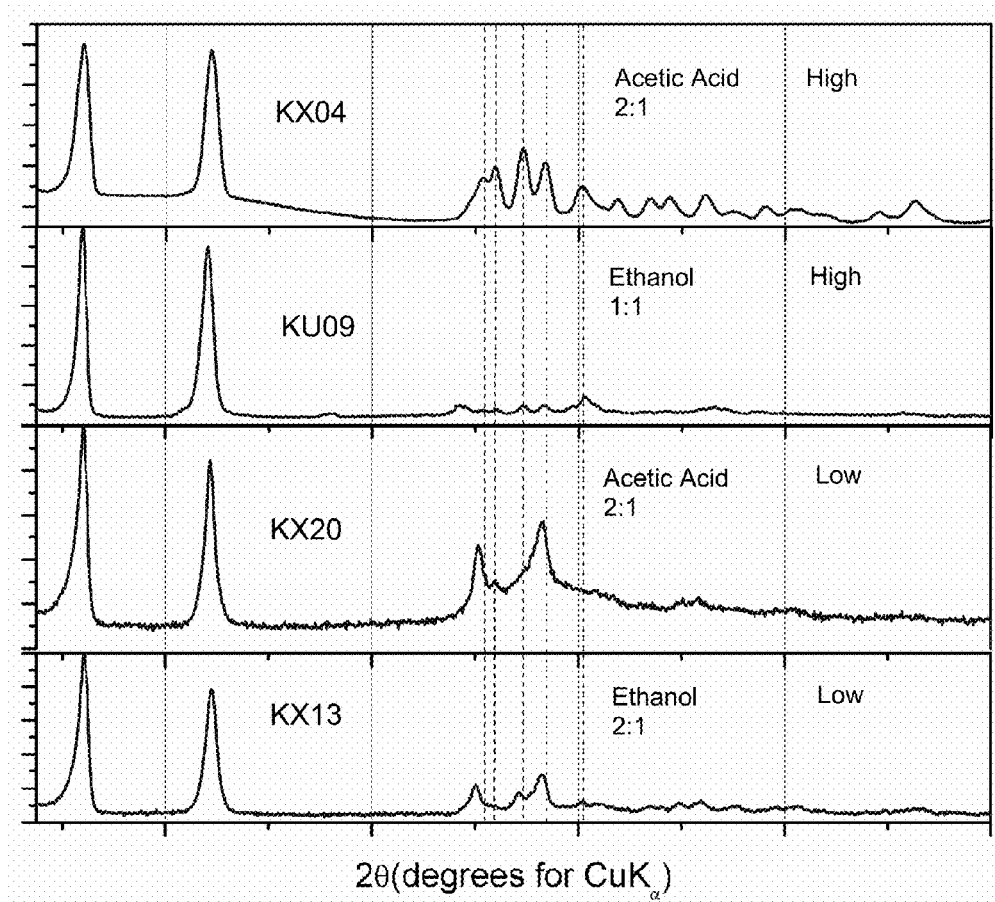
FIG. 7 shows X-ray powder diffraction patterns for a number of samples of diacetylenic monomer compositions of different proportions and crystallized from different solvents, in which patterns certain diffraction characteristics associated with high color-change reactivity are also apparent.

FIG. 7 shows similar X-ray powder diffraction spectra for samples KX04, KX09, KX13 and KX20, as labeled in FIG. 7. Some of the parameters of these samples are shown in the figure. Sample KX04 comprises a 2:1 proportion of 2,4-hexadiyn-1,6-bis (ethylurea) to 2,4-hexadiyn-1,6-bis(propylurea), is crystallized from acetic acid under uncontrolled slow cooling conditions and has a high color development reactivity. Sample KU09 comprises a 1:1 proportion of 2,4-hexadiyn-1,6-bis (ethylurea) to 2,4-hexadiyn-1,6-bis(propylurea), is crystallized from aqueous ethanol under slow cooling conditions and has a high color development reactivity.

Sample KX20 comprises a 2:1 proportion of 2,4-hexadiyn-1,6-bis(ethylurea) to 2,4-hexadiyn-1,6-bis(propylurea), is crystallized from acetic acid under fast cooling conditions and has a low color development reactivity. Sample KX13 comprises a 2:1 proportion of 2,4-hexadiyn-1,6-bis(ethylurea) to 2,4-hexadiyn-1,6-bis (propylurea), is crystallized from aqueous ethanol under fast cooling conditions and has a low color development reactivity.

Referring to FIG. 7, similarly to what is shown in FIG. 6, the presence of a high reactivity phase can be deduced from the presence in the spectra for KX04 and KU09, of fingerprint reflections at d spacings of 4.34, 4.24, 4.04, 3.89 and 3.66 Å. In the spectrum for the KX04 sample employing a proportion of 2:1, an acetic acid solvent and uncontrolled slow cooling, fingerprint peaks of good intensity are exhibited. On the other hand the fingerprint peaks for sample KU09, employing a proportion of 1:1 and an aqueous ethanol solvent and slow cooling, are rather weak, but can be seen.

In contrast, the spectra for samples KX20, employing a proportion of 2:1, acetic acid and fast cooling and KX13, employing a proportion of 2:1 aqueous ethanol and fast cooling, do not exhibit the fingerprint diffraction pattern associated with high color development reactivity. For example, the spectrum for sample KX20 lacks a peak at a d spacing of 4.04 (center broken line) and the spectrum for sample KX20 lacks a peak at a d spacing of 4.24 (second broken line from the left) and other peaks are not well positioned and defined.

Also, the high reactivity samples KX04 and KU09 exhibit an absence of other reflections between the peaks of the fingerprint spectrum such as the lines appearing in the low reactivity KX13 sample at d spacings of about 4.39, 3.96 and 2.95 Å.

Figure 9:
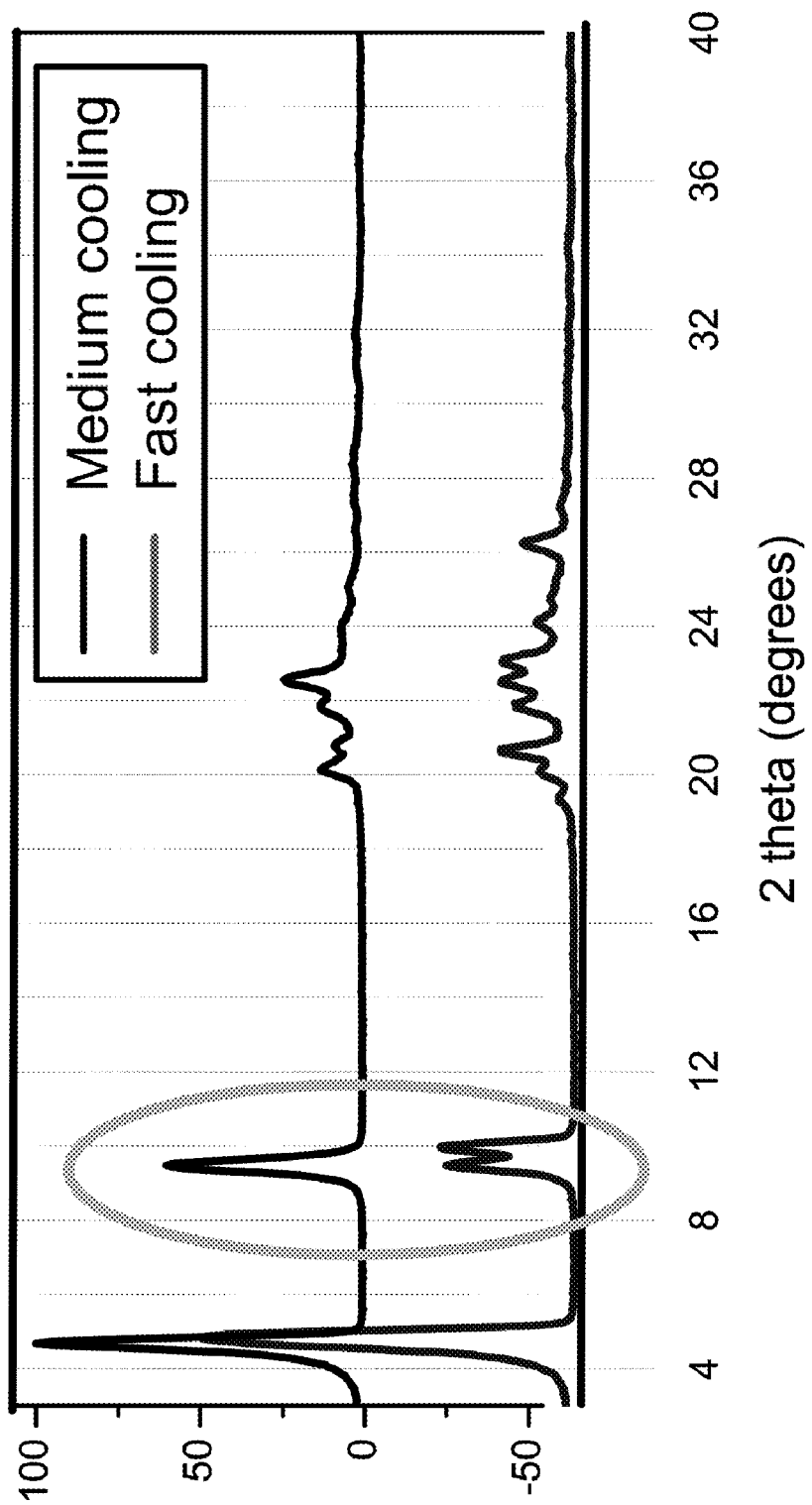
FIG. 9 shows two X-ray powder diffraction spectra for certain diacetylenic monomer compositions co-crystallized using different cooling conditions.

The X-ray diffraction spectra shown in FIG. 9 are obtainable from the products of a method of co-crystallizing a 1:1 by weight 2,4-hexadiyn-1,6-bis(ethylurea)/2,4-hexadiyn-1,6-bis(propylurea) mixture such as is described in Example 3, employing acetic acid as solvent, and using the method of Example 10 to generate the diffraction spectrum.

Results obtainable with two different cooling rates are shown. The lower diffraction spectrum is obtainable with fast cooling and the upper diffraction spectrum is obtainable with medium (intermediate) cooling.

The fast-cooled product characterized in the lower graph has high reactivity yielding a dark blue appearance after crystallization. Accordingly, the fast-cooled product does not appear to be useful as a thermal indicator agent because darkening caused by further thermally induced polymerization would probably not be readily perceptible.

In contrast, the medium-cooled product characterized in the upper diffraction spectrum is white and capable of changing color in response to applied heat, suiting it to function as an indicator agent.

The two diffraction spectra shown in FIG. 9 exhibit differences between the second lowest diffraction angle peaks in the 8-12° range of $2\theta$. Here, the fast-cooled product shown in the lower diffraction spectrum exhibits a doublet peak, whereas the medium-cooled product shown in the upper diffraction spectrum exhibits a well-defined singlet peak. The doublet peak for the fast cooled product suggests that two crystal phases may be present. In contrast, while the invention is not limited by any particular theory, the singlet peak exhibited by the medium cooled product may indicate a single phase crystal comprising a homogenous solid solution.

FIG. 10A illustrates results obtainable in an experiment to determine how color evolution of 1:1 by weight 2,4-hexadiyn-1,6-bis(ethylurea)/2,4-hexadiyn-1,6-bis (propylurea) compositions is affected by the use of different solvents and different cooling rates during crystallization. Samples are prepared by the method of Example 3 and color evolution is determined at a temperature of 60° C. by the method of Example 9. Color evolution rates at lower ambient temperatures typically encountered by host commercial products are likely to be substantially slower, and approximately proportionate, pursuant to Arrhenius kinetics. Some data obtainable are shown in Table 3.

Referring to FIG. 10A, the appearance of eight different product samples maintained at 60° C. for various times from 0 to 33 hours, as indicated in the lefthand column, is shown. The second column from the left shows results obtainable with a control, 2,4-hexadiyn-1,6-bis(ethylurea) prepared by fast-quench precipitation from acetic acid. The third to fifth columns from the left show results obtainable with fast, intermediate and slow crystallization from acetic acid, as indicated at the top of FIG. 10A, and labeled KU03, KU01 and KU14, respectively. The three columns to the right show results obtainable with fast, intermediate and slow crystallization from ethanol, as indicated at the top of FIG. 10A and labeled KU08, KU09 and KU10, respectively. These various crystal phase samples for which results are shown are 1:1 by weight samples of 2,4-hexadiyn-1,6-bis (ethylurea)/2,4-hexadiyn-1,6-bis(propylurea) prepared by the methods of Examples 6 and 8. The color development experiment is carried out in accordance with Example 9.

The number of phases identified by X-ray diffraction studies, as indicated by the presence of a distinct doublet peak in the 8-12° range of $2\theta$, is shown beneath the cooling rates. Notably, only samples prepared by intermediate cooling are seen to be a single phase. Fast cooling or slow cooling of a 1:1 mixture of 2,4-hexadiyn-1,6-bis(ethylurea) and 2,4-hexadiyn-1,6-bis(propylurea) appears to yield two phases regardless of whether the mixture is crystallized from acetic acid or ethanol.

X-ray diffraction spectra for those of the samples described in Table 3 that are crystallized from acetic acid at intermediate cooling are shown in FIG. 10B where they can be compared. The X-ray diffraction spectra in FIGS. 10B and 10C are shown for a $2\theta$ angle range of from 0° to 40° along the x-axis. The square root of the intensity is plotted on the y-axis in each of FIGS. 10B and 10C, in arbitrary units.

Referring to FIG. 10B samples KU02 and KU16-21 show powder X-ray diffraction patterns from which one phase is apparent, whereas, pursuant to the invention, two phases can be determined to be present by inspection of their diffraction patterns in each of samples KU01, KU12, KU15 and KU22.

Thus, sample KU01 shows a shoulder on the righthand side of the base of the second reflection peak. Sample KU12 shows a split second peak. Sample KU15 shows a shoulder or split peak on the righthand side of the second reflection peak. And sample KU22 shows a small shoulder on the righthand side of the second reflection peak, at the foot of the peak, as well as a slight shoulder on the righthand side of the base of the first reflection peak.

Samples KU16 to KU21 each exhibit a high reactivity pattern in the fingerprint region and this showing appears to be consistent with the reactivity parameter of the sample obtained from measurement of color evolution as described in Table 3.

FIG. 10C shows the powder X-ray diffraction patterns for samples prepared with different solvents and cooling rates, namely samples, KU03, KU08, KU09, KU10, KU14, and KU17. KU17 is chosen as representative of samples prepared from solution in acetic acid with intermediate cooling. As in FIG. 7, the vertical broken lines in some of the frames of FIG. 10C mark the locations where fingerprint reflection peaks suggesting a high reactivity phase may be present.

The diffraction patterns are arranged in FIG. 10C with patterns from acetic acid samples in the upper row and patterns from aqueous ethanol samples in the lower row. In each row, fast-cooled samples are on the left, intermediate-cooled samples are in the middle and slow-cooled samples are on the right.

KU03 has a high color development reactivity, but it is difficult to identify a high reactivity pattern in the fingerprint region. The split 002 angle reflection peak in the powder X-ray diffraction pattern for sample KU03 suggests the sample has two crystal phases. However, close examination of visual images of samples of KU03 having various color intensities, such as the views in FIG. 10A show a substantially uniform color. One possible explanation, which is not intended to limit the invention, is that the KU03 sample may be composed of two high reactivity phases of different crystallographic composition. Thus, the fingerprint region can comprise two high reactivity patterns superposed one on the other.

Samples KU03 (fast acetic acid) and KU08 (slow aqueous ethanol) appear to exhibit two 2 phases, according to their powder X-ray diffraction patterns. In KU08 both an "HR" high reactivity phase and an "LR" low reactivity phase are apparent in color development studies and can be measured with results as described in Table 3.

Samples KU14, KU09 and KU10 appear to have a single phase according to the 002 reflection of the powder X-ray diffraction pattern. However, the color test results for these samples illustrated graphically in FIG. 10A show a "salt-and-pepper" appearance believed to be associated with the presence of a low reactivity phase and some high reactivity phase. Also, the fact that two color reactivity parameters can be measured for each sample is consistent with this interpretation. The fingerprint regions of the diffraction spectra also provide limited evidence of the presence of two or more phases.

FIG. 10D shows the 002 peak for KU10 overlaid on the 002 peak for KU09, to a larger scale than in FIG. 10C. The peak for KU09 is taller, regular and symmetrical. In contrast, the peak for KU10 appears shorter and a protruding shoulder can clearly be seen on the righthand side of the peak.

FIGS. 11A, 11B and 11C illustrate results obtainable in a color development experiment such as is described in Example 9. This experiment shows how the color evolution of various samples of 2,4-hexadiyn-1,6-bis(ethylurea)/2,4-hexadiyn-1,6-bis(propylurea) compositions is affected by the crystallization parameters used to prepare the samples, for example different solvents, monomer concentrations or cooling rates.

Referring to FIGS. 11A, 11B and 11C, the grayscale appearance of six different test samples of co-crystallized 2,4-hexadiyn-1,6-bis(ethylurea)/2,4-hexadiyn-1,6-bis (propylurea) and two controls are shown at three different time stages of color development. A sample of a color standard is included as an optical and visual reference. Samples can be prepared by the method of Example 8, and color evolution is determined at a temperature of 60° C., as described in Example 9. Thermally reactive diacetylenic monomers develop color at significantly faster rates at the elevated temperature of 60° C. than they would at typical ambient temperatures of up to about 30° C. or more under some conditions. Other sample preparation methods and temperature conditions can be employed, if desired, to examine the color development properties of the sample, as will be apparent to a person of ordinary skill in the art.

Eight circular dishes containing the test samples and the two controls are arranged in a grid, with the color standard sample, a rectangle, in the lower righthand corner of the grid. The initial appearances are shown in FIG. 11A, the appearances after three hours in FIG. 11B and the appearances after 30 hours are shown in FIG. 11C.

The six test samples comprise 2,4-hexadiyn-1,6-bis(ethylurea)/2,4-hexadiyn-1,6-bis (propylurea) co-crystallized from acetic acid and ethanol at fast, intermediate and slow cooling rates respectively, namely samples numbers KX08 and KX12-KX16, as described with reference to Table 2. The samples are labeled accordingly and are arranged in FIGS. 11A-11C, along with a control sample of 2,4-hexadiyn-1,6-bis (ethylurea), labeled KE(TT), a control sample of a mixture of 2,4-hexadiyn-1,6-bis (ethylurea) and 2,4-hexadiyn-1,6-bis (propylurea), labeled KX(TT), and the color standard, with the layout shown in Table 6.

TABLE 6

Arrangement of Samples Shown in FIGS. 11A-11C

| KE (TT) | KX12 | KX08 |
|---|---|---|
| Control | Slow-EtOH | Inter-EtOH |
| KX | KX | KX |
| Fast-EtOH | Fast-HAc | Slow-HAc |
| KX | KX (TT) | Color |
| Inter-HAc | control | Standard |

In Table 6 and the drawings, "EtOH" indicates the aqueous ethanol solvent system described in Example 1 and "HAc" indicates glacial acetic acid, as employed in Example 1.

As shown in FIG. 11A, all samples are initially colorless or have little color being much lighter in appearance than the color standard. FIG. 11C shows that after 30 hours, all samples are dark. Thus all the diacetylenic monomer samples shown are thermally active. As FIG. 11B shows, the samples have a variety of reactivities, developing color at different rates under the test conditions. The highest reactivity samples for aqueous ethanol and acetic acid, respectively, are lightly circled in FIG. 11B.

From FIG. 11B, it can be concluded that high reactivity crystal phases can be obtained when a sample is crystallized from acetic acid either at an intermediate or a slow cooling rate (samples KX16 and KX15), and that when crystallizing from aqueous ethanol only the slow cooling rate yields a high reactivity crystal phase (sample KX12) whereas the sample cooled at an intermediate rate exhibits substantially less reactivity (sample KX08).

Figure 12:
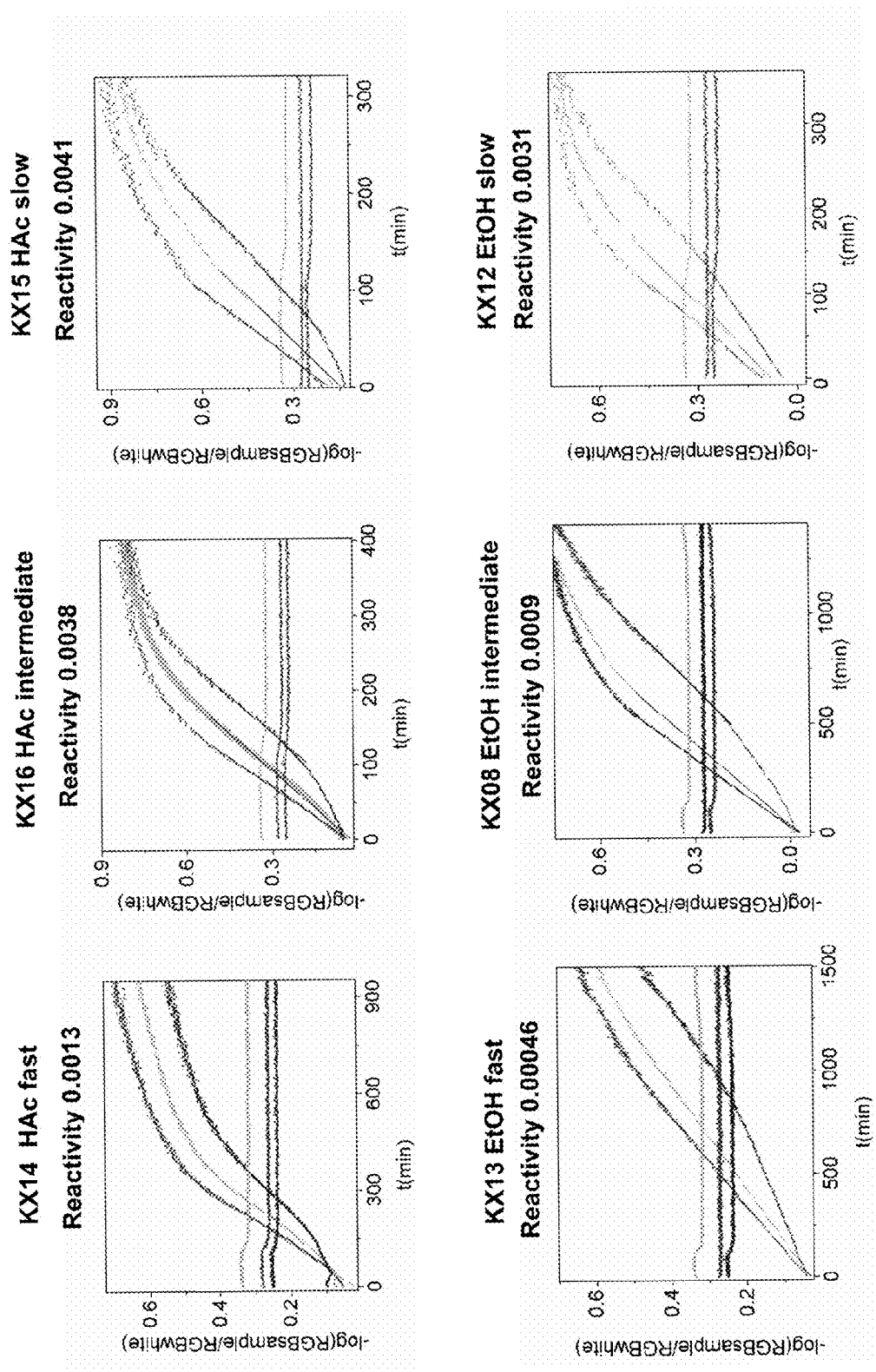
FIG. 12 comprises, in separate frames, a graphical depiction of the quantitative data obtainable for color development in the six samples of co-crystallized 2,4-hexadiyn-1,6-bis(ethylurea)/2,4-hexadiyn-1,6-bis(propylurea) compositions for which color development results at selected times are shown in FIGS. 11A-11C.

FIG. 12 shows the respective plots of the reactivity parameters in terms of time related color development with time, as described in Example 9, for each of the samples identified in Table 6 and for which color development results are shown qualitatively in FIGS. 11A-11C. Each of the six frames in FIG. 12 shows multi-spectral RGB plots for the respective sample and also for the color standard. In each three component plot, the upper component is red, the middle is green and the lower component is blue.

The plot for the color standard remains approximately horizontal with time while that for each respective sample rises from a near-zero color value at time zero, bottom left of the frame, to a substantial color value at the end of the measurement period, top right of the frame.

The scales are adjusted to enable the plots to fill the frames so that different frames may have different scales. The y-axis scales for the log of relative color intensity are moderately adjusted, notably for samples KX16 and KX15. The time scales, on the x-axis are significantly varied. The reactivity values are set forth in Table 2.

The data in FIG. 12, and the related Figures and tables, show a wide range of reactivities from which an indicator formulator can choose, which can be useful for monitoring the condition of any one of a diversity of host products. A desired reactivity within the range can be obtained by appropriate selection of crystallization parameters and other factors, as described herein, for example, monomer proportion and concentration, crystallization solvent or solvent system and cooling rate.

For example, the FIG. 12 data show that a sample such as KX15 or KX16, which is crystallized from acetic acid by cooling at a slow or intermediate rate, exhibits a reactivity parameter which is about 3 times higher than that exhibited by a fast cooled acetic acid sample such as sample KX14.

Also, a sample such as KX12, which is crystallized from acetic acid with slow cooling, exhibits a reactivity parameter which is about 7 times higher than that exhibited by a fast cooled aqueous ethanol sample such as sample KX13 and more than 3 times higher than the reactivity exhibited by an intermediate cooled aqueous ethanol sample such as sample KX08. The slow cooled ethanol sample, sample KX12 exhibits a reactivity which is approaching the reactivities of the high reactivity acetic acid samples KX16 and KX15.

From these data, the kinetics of co-crystallized compositions comprising a 2:1 weight ratio of 2,4-hexadiyn-1,6-bis (ethylurea) to 2,4-hexadiyn-1,6-bis(propylurea) appear to be more rapid than the kinetics of samples comprising a 1:1 weight ratio of 2,4-hexadiyn-1,6-bis(ethylurea) to 2,4-hexadiyn-1,6-bis(propylurea). However, surprisingly, for the samples crystallized from ethanol, a peak reactivity can be exhibited by a 1:1 weight ratio of 2,4-hexadiyn-1,6-bis(ethylurea) to 2,4-hexadiyn-1,6-bis(propylurea) produced under certain cooling conditions, as is further described herein with reference to FIG. 16.

Referring now to FIGS. 13A-13B, as has been explained in relation to the data shown in FIGS. 6 and 7, high reactivity crystal phase samples can exhibit a distinctive "fingerprint" pattern of peaks in their powder X-ray diffraction spectra. The fingerprint pattern can enable a high reactivity crystal phase to be identified and distinguished from a low reactivity crystal phase without having to conduct color development experiments. This understanding is borne out by the spectra shown in FIGS. 13A-13B, as will now be explained.

FIGS. 13A-13B show powder X-ray diffraction spectra for twelve of the 2:1 2,4-hexadiyn-1,6-bis(ethylurea) to 2,4-hexadiyn-1,6-bis(propylurea) samples listed in Table 2 which spectra can be generated by a method such as the method described in Example 10. The data are organized to display spectra for samples crystallized from acetic acid in FIG. 13A and data for samples crystallized from aqueous ethanol in FIG. 13B. As labeled in FIGS. 13A and 13B, for each solvent system, results are shown for two samples cooled at each of three cooling conditions, fast, intermediate and slow.

The X-ray diffraction spectra in FIGS. 13A-13B are shown for a 2θ angle range of from 0° to 40° along the x-axis. The square root of the intensity is plotted on the y-axis, in arbitrary units, using a larger scale for the aqueous ethanol spectra shown in FIG. 13B which exhibit less intense peaks. For each sample characterized, two singlet peaks are generated at lower 2θ angles, one at about 5° and another at about 10°. No splitting of these two lowest angle singlet peaks is observed.

FIGS. 14A-B show the portions of the X-ray powder diffraction spectra shown in FIGS. 13A-B at 2θ, angles of from 18° to 33°, to a larger scale on the x-axis, so that the presence or absence of a distinctive fingerprint pattern can better be seen.

Referring to FIG. 14A, showing spectra for samples crystallized from acetic acid, a high reactivity phase can be seen to be present in the spectra either for samples obtained by intermediate cooling ("medium" cooling in the figure), samples KX24 and KX16, or for samples obtained by slow cooling, samples KX23 and KX15. The presence of a high reactivity phase is indicated by the presence of a primary fingerprint pattern of reflections at d spacings of 4.24, 4.04 and 3.89 Å (the three center broken lines) as well as secondary fingerprint reflections at d spacings of 4.34 and 3.66 Å (the two outer broken lines).

Referring to FIG. 14B, showing spectra for samples crystallized from aqueous ethanol, the distinctive fingerprint pattern of peaks at d spacings 4.24, 4.04 and 3.89 Å can be seen to be present in the spectrum of the single sample exhibiting high color development reactivity, sample KX12. However, the peaks have a significantly lower intensity than the corresponding peaks in the spectra from acetic acid crystallization samples. Also, the KX12 sample shows a weak secondary fingerprint reflection at a d spacing of 4.34 Å.

Still referring to FIG. 14B, samples KX13, KX18 and KX08 prepared by fast or medium (intermediate) cooling, which exhibit low color change reactivity in color development tests, appear to show the presence of a low reactivity phase which is characterized by the presence of reflections at d spacings 4.39, 3.96 and 2.95 Å. Sample KX17 also shows low reactivity in color development tests. However, the corresponding diffraction spectrum exhibits weak, poorly formed peaks and a high level of background reflections. The fingerprint region of the KX17 diffraction spectrum appears to suggest the presence of a low reactivity phase, albeit not clearly, but does not appear to provide evidence of a high reactivity phase.

From the data described herein, it can be seen that 2:1,2,4-hexadiyn-1,6-bis (ethylurea)/2,4-hexadiyn-1,6-bis(propylurea) samples crystallized from acetic acid comprise a high reactivity phase when prepared by intermediate or slow cooling. However, this phase does not clearly exhibit itself in samples prepared by fast cooling. Also, the presence of a high reactivity phase can be detected by examining an X-ray powder diffraction spectrum of a sample for the presence of reflections associated with the high reactivity phase and for the absence of reflections associated with a low reactivity phase.

For 2,4-hexadiyn-1,6-bis(ethylurea)/2,4-hexadiyn-1,6-bis (propylurea) (2:1) recrystallized from ethanol a high reactivity phase is only obtained under extended cooling conditions, using for example, a short vacuum flask as is described in Example 1, when large, plate-like crystals can usually be obtained. Slow cooling, as opposed to extended cooling, can yield large needle-like crystals corresponding to the low reactivity phase.

Without intending to limit the invention by any particular theory, it is believed that some of the co-crystallized compositions described herein can include more or less of a distinct crystal phase which can exhibit high color-change reactivity and a characteristic X-ray powder diffraction fingerprint. Complementarily, it is believed that others of the co-crystallized compositions described herein include little of the distinct high reactivity crystal phase and are less reactive. These less reactive co-crystallized compositions may exhibit a more modest color-change reactivity and may lack the characteristic X-ray powder diffraction fingerprint of the high reactivity phase or may exhibit the fingerprint only weakly or unclearly.

This understanding provides the possibility of varying the color-change reactivity of a diacetylenic co-crystallized composition by varying the proportion of the high reactivity phase. Also, the high reactivity phase can be identified by its distinctive X-ray powder diffraction fingerprint, if desired.

Figure 15:
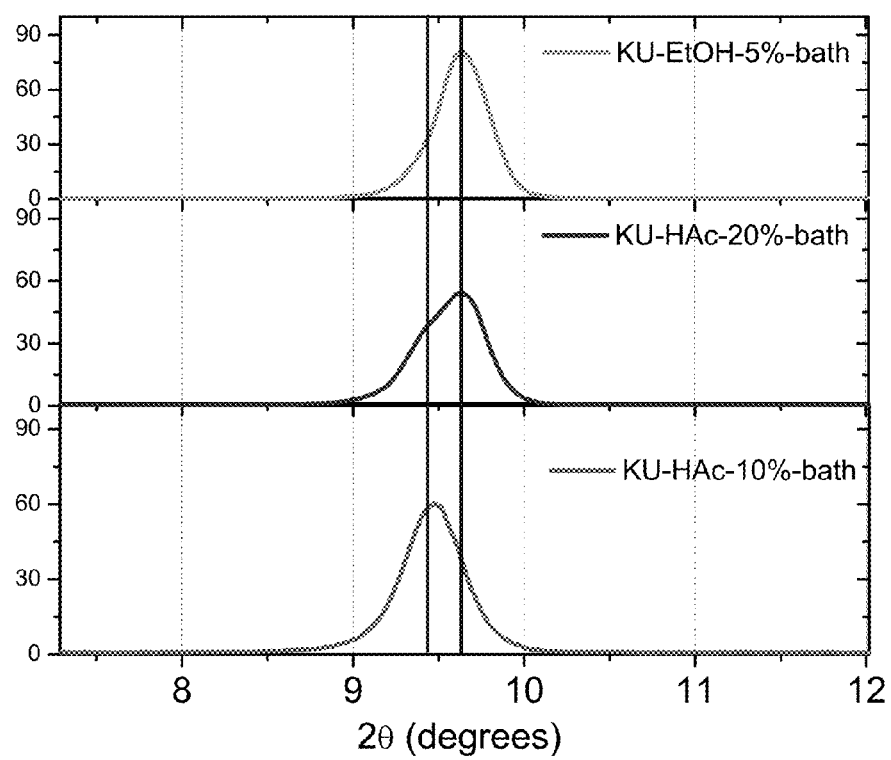
FIG. 15 shows the effect the proportions of the dissolved monomer composition and the solvent system employed can have on the X-ray powder diffraction spectrum of an embodiment of a co-crystallized mixture of 2,4-hexadiyn-1,6-bis(ethylurea) and 2,4-hexadiyn-1,6-bis(propylurea) according to the present invention.

The data shown in FIG. 15 illustrate the role that the diacetylenic monomer concentration in the crystallization liquor can play in solid monomer formation in the case of crystallization of 1:1 by weight 2,4-hexadiyn-1,6-bis(ethylurea)/2,4-hexadiyn-1,6-bis(propylurea).

Referring now to FIG. 15, the samples employed to generate the diffraction patterns shown are prepared in accordance with Example 6. Two samples are prepared by crystallization from acetic acid employing initial monomer concentrations of about 10 percent by weight (lower diffraction spectrum in FIG. 15) and 20 percent by weight (center diffraction spectrum in FIG. 15), respectively. A third sample is prepared by crystallization from ethanol employing an initial monomer concentration of about 5 percent by weight (upper diffraction spectrum in FIG. 15). Intermediate cooling is employed for all three samples.

X-ray diffraction spectra are generated for the three samples by the method of Example 10. FIG. 15 shows a portion of each spectrum for a range of 2θ from about 7° to 12° as marked on the x-axis in the figure. The intensities on the y-axis are normalized so that the first reflection is 100 and the larger scale markers correspond to 30 arbitrary units. Two vertical lines are provided in the middle of the figure to help locate the peak positions on the x-axis.

FIG. 15 shows a portion of the diffraction pattern for each of the three samples which exhibits the second longest peak in the diffraction signature, occurring at a 2θ angle of between 9° and 10°. The peaks for the 5 percent sample crystallized from aqueous ethanol and the 10 percent sample crystallized from acetic acid are symmetrical, essentially singlet peaks which occur at 2θ angles that differ by about 0.2°. These characteristics may indicate that each sample is a single-phase solid solution. The 20 percent sample crystallized from acetic acid shows a peak at the same value as the 5 percent sample crystallized from ethanol with a gently sloping shoulder at about the same 2θ angle as the peak of the 10 percent sample crystallized from acetic acid.

Comparing the lower diffraction spectrum in FIG. 15 with the center and upper spectra, the position of the 9° to 10° peak can be seen to be moved by a change in either concentration (middle diffraction spectrum) or solvent (upper diffraction spectrum). While the invention is not limited by any particular theory, it is contemplated that this difference in peak position may correspond to 1:1 in 2,4-hexadiyn-1,6-bis(ethylurea) structure and 1:1 in 2,4-hexadiyn-1,6-bis(propylurea) structure. Since the crystals of 2,4-hexadiyn-1,6-bis(ethylurea) and KPr have different symmetries, it is contemplated, again without limitation, that two different phases can be present in the same composition. One phase can have the symmetry of 1:1 in 2,4-hexadiyn-1,6-bis(ethylurea and the other phase can have the symmetry of KPr. Furthermore, 50% of 2,4-hexadiyn-1,6-bis(ethylurea) can insert into the KPr symmetry and 50% of KPr can insert into the 2,4-hexadiyn-1,6-bis(ethylurea) symmetry. These two structures can therefore have the same composition and a different d-spacing, due to the difference in symmetry.

Also, it is contemplated, without limitation, that for the second longest diffraction spacing, which corresponds to the reflection appearing at a 2θ angle between about 9° and 10°, and which generally appears to be a singlet for a single phase sample, the presence of a shoulder, or splitting of the peak can indicate the presence of a second phase. Generally, an intermediate cooling rate yields a single phase sample for 10% acetic acid compositions. However, as the center diffraction pattern in FIG. 15 suggests, if the amount of monomer in solution is increased to 20 percent by weight, this reflection may cease to be a singlet, suggesting the presence of a second phase.

Figure 16:
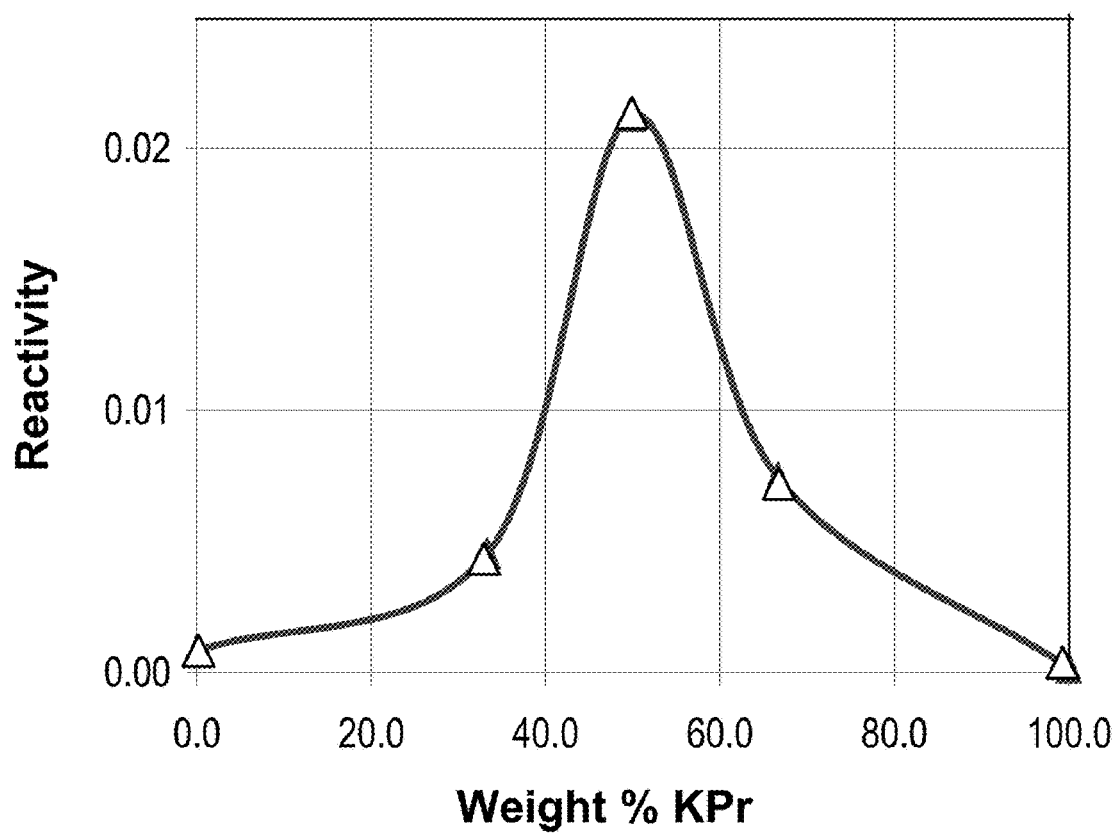
FIG. 16 shows the effect that varying the proportions of the composition of a mixture of 2,4-hexadiyn-1,6-bis(ethylurea) and 2,4-hexadiyn-1,6-bis (propylurea) co-crystallized from aqueous ethanol according to an embodiment of the present invention can have on the optically determined thermal reactivity of the monomer.

FIG. 16 shows how the optically determined reactivity of a mixture of 2,4-hexadiyn-1,6-bis(ethylurea) and 2,4-hexadiyn-1,6-bis(propylurea) crystallized from ethanol varies with the relative proportions of 2,4-hexadiyn-1,6-bis(ethylurea) and 2,4-hexadiyn-1,6-bis(propylurea) in the mixture. The samples employed to generate the reactivity graph shown are prepared in accordance with Example 5. As indicated by the data points in FIG. 16, and as stated in Example 5, the proportions of 2,4-hexadiyn-1,6-bis(ethylurea): 2,4-hexadiyn-1,6-bis(propylurea) employed are 1:0, 2:1, 1:1, 1:2 and 0:1. The thermal reactivity of the samples is determined optically by determination of changes in the optical properties of each sample, such as darkening or color development, with time, at a controlled temperature of 60° C. and is shown in arbitrary units on the y-axis in FIG. 16.

Referring to FIG. 16, it can be seen that the peak reaction rate occurs at a weight ratio of 2,4-hexadiyn-1,6-bis(ethylurea) to 2,4-hexadiyn-1,6-bis(propylurea) of about 1:1. This is different from the peak reaction rate for 2,4-hexadiyn-1,6-bis(ethylurea)/2,4-hexadiyn-1,6-bis(propylurea) co-crystallized from acetic acid which occurs at a proportion of about 2:1, by weight. Furthermore, the reaction rate for 1:1 2,4-hexadiyn-1,6-bis(ethylurea)/2,4-hexadiyn-1,6-bis(propylurea) co-crystallized from ethanol is lower than that for 2:1 2,4-hexadiyn-1,6-bis(ethylurea)/2,4-hexadiyn-1,6-bis(propylurea) co-crystallized from glacial acetic acid. Thus crystallization of a mixture of 2,4-hexadiyn-1,6-bis(ethylurea) and 2,4-hexadiyn-1,6-bis(propylurea) from ethanol provides to an indicator formulator an indicator agent having a new range of thermal reactivities for correlating with a host product's temperature response parameters, both at the peak reactivity proportion of 1:1 by weight, and at other proportions. The invention includes indicators employing indicator agents comprising ethanol-crystallized 2,4-hexadiyn-1,6-bis(ethylurea)/2,4-hexadiyn-1,6-bis(propylurea).

Monomer Model

Figure 17:
FIG. 17 is a depiction of a skeletal model of a 2,4-hexadiyn-1,6-bis(ethylurea) monomer molecule.

Referring to FIG. 17, according to the model shown, the 2,4-hexadiyn-1,6-bis (ethylurea) monomer molecule can be seen to have a central hexadiyn core comprising two conjugated triple-bonded acetylene groups and two alkylurea groups, substituted one each at opposed ends of the hexadiyn core. The ethyl groups terminate the ends of the molecule.

A comparable model for the 2,4-hexadiyn-1,6-bis(propylurea) molecule comprises a similar skeletal configuration to that shown for 2,4-hexadiyn-1,6-bis(ethylurea) with a methylene group added to each alkyl substituent, giving the 2,4-hexadiyn-1,6-bis(propylurea) molecule a somewhat longer appearance, pursuant to the model. Other 2,4-hexadiyn-1,6-bis(alkylurea)s are believed to have similar structures, the lengths of each alkyl group varying with the particular molecule.

The molecular weights of 2,4-hexadiyn-1,6-bis(ethylurea) and 2,4-hexadiyn-1,6-bis (propylurea) are quite close, differing only by 28 daltons, the value for two methylene units. Thus, the molecular weight of 2,4-hexadiyn-1,6-bis(ethylurea) is 250 daltons and of 2,4-hexadiyn-1,6-bis(propylurea) is 278 daltons.

Thus, the weight proportions of mixtures of 2,4-hexadiyn-1,6-bis(ethylurea) and 2,4-hexadiyn-1,6-bis(propylurea) are only modestly different from molar proportions. Accordingly, where weight proportions of 2,4-hexadiyn-1,6-bis (ethylurea) to 2,4-hexadiyn-1,6-bis(propylurea) such as 1:1 and 2:1 are referenced herein, molar proportions can be used, if desired, or may be appropriate.

Polymerization Model

As described herein, useful time-temperature indicators can employ the color changes observed when a diacetylene polymerizes in the solid state transforming colorless crystals of monomer into polymer crystals which may become intensely colored with sufficient thermal exposure over time. In this reaction, the crystal structure of the monomer is believed to juxtapose the individual monomer molecules sufficiently closely together for efficient polymerization to occur.

Figure 18:
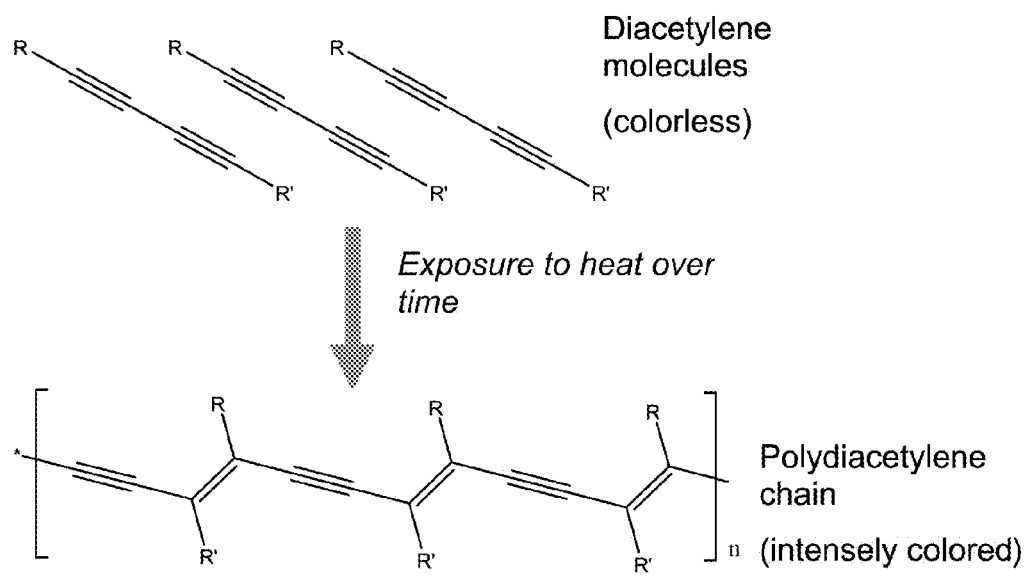
FIG. 18 is a schematic representation of one model of diacetylene polymerization.

A simplified model of the polymerization reaction is shown in FIG. 18 and will now be described. However, it is to be understood that the invention is not intended to be limited by this or any other theory, although the following explanation may provide one or more helpful insights regarding the invention.

Referring to FIG. 18, it will be understood that R and R' can be the same, and can, for example, each be the same alkylurea substituent, as is the case for 2,4-hexadiyn-1,6-bis(ethylurea) and 2,4-hexadiyn-1,6-bis(propylurea) and some other useful diacetylenic compounds described herein. As shown in FIG. 18, with polymerization, the 2, 3 and 4, 5 triple bonds in the monomer molecule give way to a single 3, 4 triple bond in the polymerized monomer unit. The electrons made available provide a 5, 2 double bond coupling each monomer unit to its neighbor.

It is believed that the reaction direction, or direction of polymerization will be substantially or generally in the direction in which hydrogen bonding occurs between neighboring polymerizable molecules. Pursuant to models such as are described herein, the invention includes co-crystallized diacetylenic compositions comprising hydrogen bonds between neighboring or adjacent polymerizable diacetylenic molecules of differing chemical structure. Such hydrogen bonds can extend in a direction to permit 1,4-addition polymerization between neighboring molecules. For example, a hydrogen bond can extend from each of two urea —NH— groups on one polymerizable diacetylenic molecule to the =C=O group on a neighboring polymerizable diacetylenic molecule of the same or differing chemical structure. Similarly, two more hydrogen bonds can extend one each from each of two urea —NH— groups on one polymerizable diacetylenic molecule to the =C=O group on a neighboring polymerizable diacetylenic molecule of the same or differing chemical structure. Thus there can be four hydrogen bonds between two neighboring or adjacent polymerizable or polymerized diacetylenic monomer molecules.

The role of hydrogen bonding in the polymerization of diacetylenic monomers is also discussed in Baughman et al. in relation to individual diacetylenic compounds. Similar considerations are believed applicable to the co-crystallized compositions and solid solutions of the present invention.

Because the distinct color change brought about by the polymerization reaction is irreversible, the reaction is well suited to indicating when perishable products such as vaccines, medicines and food lost their vitality or freshness have expired, or have reached another end point, owing to thermal exposure or to another environmental condition which also induces diacetylenic polymerization.

Table 5 in FIG. 19 of the accompanying drawings shows some examples of data obtainable by the method described in Example 11 which employs $^{13}$C NMR spectroscopy to characterize some of the products of Examples 1-7.

Referring to Table 5, the first column on the left of the table numbers the table rows for convenient reference. The second column graphically depicts various chemical groupings in a target compound that can be associated with the $^{13}$C NMR data that are set forth in the third to eighth columns in Table 5 and extend to the right as viewed in FIG. 19.

Data in the third to eighth columns of Table 5 are for chemical shifts in the NMR spectrum, in parts per million ("ppm" herein), which are exhibited by the particular product characterized when subjected to $^{13}$C NMR spectroscopy by a method such as is described in Example 11. Depending upon the method of displaying the data, the chemical shifts may appear as bands, peaks or numerical values. The chemical shift data are organized in decreasing value reading down the table. Specific shifts are associated with the specific chemical groups indicated in the second column of the table.

The third column shows $^{13}$C NMR data obtainable by characterization of crystals of 2,4-hexadiyn-1,6-bis(ethylurea), "KE" or "KE monomer herein", produced by a known method comprising recrystallization from glacial acetic acid with fast quench precipitation, as described herein.

The next column on the right shows KE polymer data obtainable by a method according to Example 7 performed employing the KE monomer crystals used to provide the data shown in the adjacent column to the left.

The next column on the right shows $^{13}$C NMR data obtainable by characterization of KPr monomer crystals also produced by a known method of recrystallization from glacial acetic acid with fast quench precipitation. The fifth column shows $^{13}$C NMR data for a KPr polymer obtainable by a method according to Example 7, which method is performed employing the KPr monomer crystals used to provide the data shown in the fourth column.

The next-to-last column on the right shows $^{13}$C NMR data obtainable by characterization of 2:1 by weight KX monomer crystals produced by a known method of recrystallization from glacial acetic acid with fast quench. The peaks exhibited by the individual KE and the KPr monomers can essentially also be found in the KX monomer spectrum.

The final column on the right in Table 5 shows $^{13}$C NMR data for a KX polymer obtainable by a method according to Example 7 performed employing the KX monomer crystals used to provide the data shown in the next column on the left.

As can be seen from the second column of Table 5, rows 2, 3 and 7 of the table relate to chemical groups that appear in the diacetylenic polymers characterized, and which are not present in the monomers. Rows 4, 5 and 9 relate to chemical groups that appear in the diacetylenic monomers characterized but not in the polymers. And rows 1, 6, 8, 10 and 11 relate to chemical groups that appear in both the polymers and the monomers.

Chemical shift values observable for the single bond carbon atoms in the monomer and polymer molecules characterized are set forth in rows 6-11 of Table 5. The differences in the $^{13}$C NMR data shown for single bond carbon atoms, between the monomers and their respective polymers, (row 9 versus row 7), as well as the loss of triple-bond (sp) carbon atom signals (rows 4 and 5) and the appearance of new triple-bond (sp) carbon atom signals (row 3) and double-bond (sp$^2$) carbon atom signals (row 2), appear to be consistent with the diacetylene polymerization model described with reference to FIG. 18.

The three graphs shown in FIG. 20 represent $^{13}$C NMR spectra for each of the three monomer products for which data appear in Table 5. The monomer data in Table 5 relate to peaks which can be calculated from graphs such as are shown in FIG. 20. A chemical structural formula for KPr is also shown in FIG. 20 above the three graphs providing the NMR data. Arrows indicate which carbon atoms in the structural formula can be associated with which peaks in the graphs.

Referring to FIG. 20, it can be seen that the pattern of $^{13}$C NMR peaks for KPr is generally similar to that for KE. Some minor lateral shifts can be seen in the peaks corresponding to C atoms of the urea substituted alkyl group, attributable to the small difference in structure between KE and KPr, namely a methylene group, —CH$_2$—, at each end. An arrow on the righthand side of the figure points out the peak at about 25 ppm (row 10 in Table 5) which corresponds with this additional methylene group in KPr. The terminal methyl group gives rise to peaks in both KE and KPr which are close together, as indicated by the heavier arrows on the righthand side of FIG. 20. The terminal methyl peak for KE is shifted upwardly (to the left in FIG. 20) and is a little more intense than that for KPr. The peaks corresponding to the two different triple-bond (sp) carbon atoms and the methylene carbon atom between the urea group and the diacetylene unit appear with similar values of the chemical shifts corresponding with carbon atoms that are almost chemically equivalent.

The three graphs shown in FIG. 21 represent $^{13}$C NMR spectra for each of the three polymer products for which data appear in Table 5. The polymer data in Table 5 relate to peaks which can be calculated from graphs such as are shown in FIG. 21. A structural formula for one possible unit of the KX polymer comprising a KE unit (below) coupled to a KPr unit (above) by a double bond is also shown in FIG. 21 above the three graphs providing the NMR data.

Referring again to FIG. 19 and looking at the peak values for the KE monomer and polymer in columns 2 and 3 of Table 5, and comparing rows 2 and 3 with rows 4 and 5, the realignment of carbon bonds expected by the polymerization model is clearly evidenced. Peaks for the 1-2 and 3-4 triple-bond (sp) carbon atoms that are present in the monomer (rows 4 and 5) disappear in the polymer. Instead, the polymer exhibits chemical shifts appropriate for the triple-bond (sp) carbon atom and also for the double-bond (sp$^2$) carbon atom which theory predicts couples each monomer unit to its neighbor. Comparable peaks, with slightly different values, are exhibited by the KPr monomer and polymer. The differences between the KE and KPr polymers and their respective monomers can also be seen graphically by comparing the graphs in FIG. 21 with the corresponding graphs in FIG. 20.

Similar changes, with some significant differences, can be seen in the $^{13}$C NMR data for the KX polymer by comparing the KX monomer peaks with the KX polymer peaks. Similarly to KE and KPr, this comparison shows the absence from the KX polymer of two triple bond (sp) carbon peaks in the 60-80 ppm range that are present in both the KE and KPr monomers and the presence in the KX polymer of peaks at about 130 ppm (two peaks) and near 100 ppm (four peaks).

Whereas each of the KE and KPr polymers exhibits a single triple bond (sp) carbon peak near 100 ppm, the KX polymer exhibits four triple-bond (sp) carbon peaks in this vicinity (row 3). These four peaks can be understood as possibly corresponding to chemically different triple bond (sp) carbon atoms in a molecule of KE linked to another KE molecule (KE-KE), or alternatively linked to a KPr molecule (KE-KPr) or to triple bond carbon atoms in a molecule of KPr linked to a KE molecule, or to a KPr molecule.

Also, each of the KE and KPr polymers exhibits a single double-bond (sp$^2$) carbon peak in the vicinity of 130 ppm, whereas the KX polymer exhibits two shifted peaks in this vicinity (row 2). These characteristics are believed to indicate co-polymerization of the KE and KPr monomers in the KX polymer molecule.

The absence from the polymers of peaks at about 77 ppm (row 4) and about 66 ppm (row 5) which are present in the monomers suggests that the monomers are no longer present in the polymer product, having fully participated in the polymerization reaction. Similarly, the absence of characteristic polymer peaks in the vicinity of 100 ppm and 130 ppm from the $^{13}$C NMR spectrum of the KE and KPr monomers suggests that no detectable room temperature polymerization has occurred in the monomers.

Moreover, the presence of multiple peaks in the region of chemical shifts ranging from 95 to 110 ppm in the KX polymer suggests the existence of a random KX copolymer with both KE and KPr monomer units being present in individual ones of the crystallographic stacks.

These differences between the KX polymer and the KX monomer can also be seen graphically by comparing the lowermost graph in FIG. 21 with the lowermost graph in FIG. 20.

A clear signature of polymerization in the described polymer products is the disappearance of the bands or peaks corresponding to the monomer triple-bonds and the appearance of new bands associated with a new triple-bond (sp) carbon atom and a newly formed (sp$^2$) carbon atom in the polymer. These features are exhibited by all three monomer systems, KE, KPr, and KX and appear to indicate that a quantitative transformation from monomer to polymer can be observed in each case. It appears from this data that there is little or no residual monomer in the polymer product.

Figure 22:
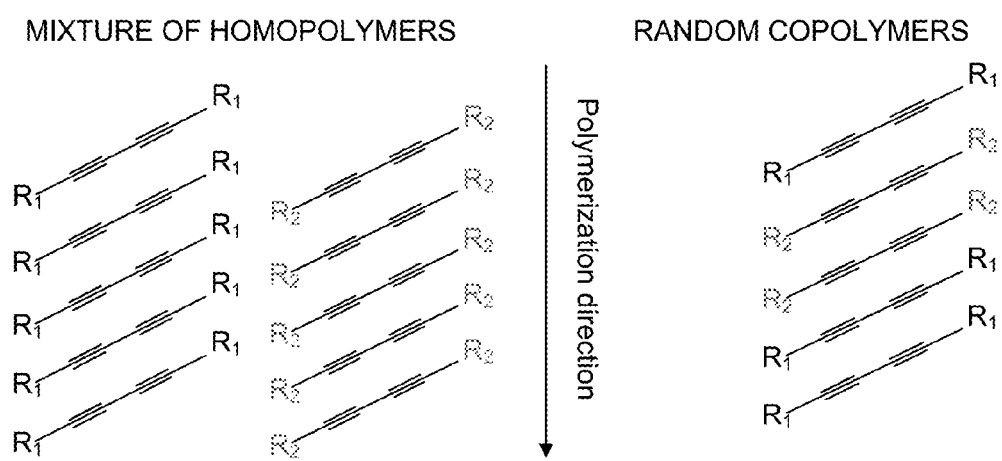
FIG. 22 is a schematic depiction of a model of two arrangements of units of a diacetylenic monomer composition in a polymer of the composition.

FIG. 22 shows schematically two different ways in which the molecules of a mixture of diacetylenic monomer compounds, for example a mixture of KE and KPr, can be arranged in a crystal lattice. The molecules of compounds such as KE and KPr, and some other hexadiyn bis(alkylurea)s, when crystallized, are believed to have an essentially linear conformation and to be aligned alongside one another. This arrangement is believed to juxtapose the pair of triple bonds in one molecule closely with the pair of triple bonds in an adjacent molecule facilitating rearrangement of the triple bonds to provide a double bond between the monomer units, when polymerized.

FIG. 22 illustrates hypothetically how three such stacks of diacetylenic monomer molecules might be arranged, when viewing a crystal of KX monomer in the direction of polymerization of the monomers. The lefthand side of the figure shows two stacks of diacetylenic monomer molecules, one with alkylurea substituents $R_1$ and the other with alkyl urea substituents $R_2$. Each stack is homogenous and in response to suitable thermal exposure, or other appropriate energy input, can be expected to polymerize to form a homopolymer. Where the crystals comprise a mixture of such stacks, an ordered arrangement with stacks of different homopolymer chains can be expected in the polymer.

The righthand side of FIG. 22 shows a single stack of diacetylenic monomer molecules in which two monomers, one with alkylurea substituents $R_1$ and the other with alkyl urea substituents $R_2$ are schematically depicted as being randomly arranged within the stack. In this case each monomer stack comprises a mixture of the two monomer molecules. The stack is heterogeneous and in response to suitable thermal exposure, or other appropriate energy input, can be expected to polymerize to form a copolymer of the two monomers. The copolymer can comprise $R_1$-containing monomer units coupled to $R_2$-containing monomer units as well as $R_1$—R1 couplings and $R_2$—$R_2$ couplings.

Accordingly, in light of data such as are shown in FIGS. 19-21, it is possible that, in the 2:1 KE/KPr co-crystallized structure characterized, the KE and KPr molecules are substantially uniformly mixed within individual stacks in the polymerization direction, providing random mixtures of the two molecules within a stack, as suggested on the righthand side of FIG. 22.

Another possibility is that the KE and KPr molecules are mixed within an individual stack in an orderly manner. For example, a single KPr molecule can alternate with a single KE molecule, or a pair of KE molecules, depending upon the concentration in the crystallization liquor, i.e. one or two KE molecules can be followed by a single KPr molecule, repeating the pattern throughout the stack.

The present invention is not limited by any particular theory. That being said, based on the $^{13}$C NMR data described herein, it is believed that, if a co-crystallized KX monomer were comprised of homogenous stacks of either KE or KPr, as illustrated on the lefthand side of FIG. 22, then, following polymerization, a mixture of homopolymers would be obtained. It is also believed that within the range of chemical shift of 95-110 ppm, each homopolymer would generate a single chemical shift peak. As can be seen from Table 5, four peaks are observed in the 95-110 ppm range. The presence of four peaks in this range appears to be inconsistent with the formation of two homopolymers, but may be consistent with copolymerization, as is further explained below.

If KE and KPr are randomly mixed within each stack, as suggested on the righthand side of FIG. 22, a random copolymer will form when polymerization is induced. Then, in addition to a peak associated with reconfiguration of the triple bonds in the KE molecule to double bond with another KE molecule, and a corresponding peak for a KPr molecule coupling with another KPr molecule, third and fourth peaks can be expected. Reconfiguration of the triple bonds in a KE molecule to double bond with a KPr molecule may yield a third peak and bonding of a reconfiguration of the triple bonds in a KPr molecule to double bond with a KE molecule can yield a fourth peak. Pursuant to this model, the presence of four chemical shifts in the 95-110 ppm range appears to be a clear signature of the presence of the KE-KPr copolymer in the crystal.

Characterization of KX, and other diacetylenic products subject to spontaneous solid-state polymerization, by $^{13}C$ NMR methods such as are described herein, to determine conversion of monomer to polymer, or lack thereof, in either the monomer or polymer products can be employed in the practice of the invention described herein. In one such application, a monomer can be selected for use in commercial applications, for example for monitoring thermal exposure or other ambient conditions, according to an acceptable percentage conversion of the monomer to polymer, as is determined by $^{13}C$ NMR characterization for example 0.1 percent, 1 percent or 10 percent, depending upon the monomer and the application.

In one example of such an application, the monomer-to-polymer conversion at intermediate and substantial degrees of polymerization can be quantified by $^{13}C$ NMR characterization. This information can be used to provide another way of varying the color change reactivity of a diacetylenic monomer.

For example, by employing a monomer which has undergone a known percentage conversion, bringing the monomer closer to a color change end point, the response algorithm of the monomer can be shortened. Such a monomer will have a truncated color evolution profile as compared with the monomer itself, and can be employed to match time-temperature related quality, freshness or other characteristics of a target host product which are different from those matched by the virgin monomer. The polymer-modified diacetylenic monomer provides an additional option and can be used to monitor the quality of the target host product having different characteristics.

In another example, information about the conversion of a color-changing diacetylenic monomer obtained by $^{13}C$ NMR characterization can be employed to monitor the progress of the polymerization reaction. For example, $^{13}C$ NMR characterization can be used to calibrate optical methods of determining the conversion such as reflective densitometry. Reflective densitometry can be performed in any suitable manner, for example, by illuminating substrate printed samples of an ink comprising the diacetylenic monomer. By calibrating the more easily performed optical methods with $^{13}C$ NMR characterization, improved accuracy, consistency or control of the optical methods can be obtainable leading to improved monitoring of a host product's freshness or other condition. The invention includes such improved methods.

For example, $^{13}C$ NMR can be employed to determine the percentage conversion of a monomer whose color changes only modestly or moderately as the monomer polymerizes. For monomers exhibiting a more pronounced color change, optical methods can provide useful information regarding polymer conversion possibly at quite low degrees of conversion.

$^{13}C$ NMR characterization of the conversion can also be employed for quality control in manufacturing monitoring products comprising color-changing diacetylenic monomers as active agents. Suitable quality control methods can be either inline, continuously checking all, or a proportion of samples produced. Alternatively, quality control employing $^{13}C$ NMR characterization can be applied to random samples of a production batch. For example, one or more samples can be checked for undesired polymerization that could adversely affect the color development profile of the sample. Modest conversion may be revealed by $^{13}C$ NMR characterization yet not be apparent to visual inspection or other optical methods.

Figure 23:
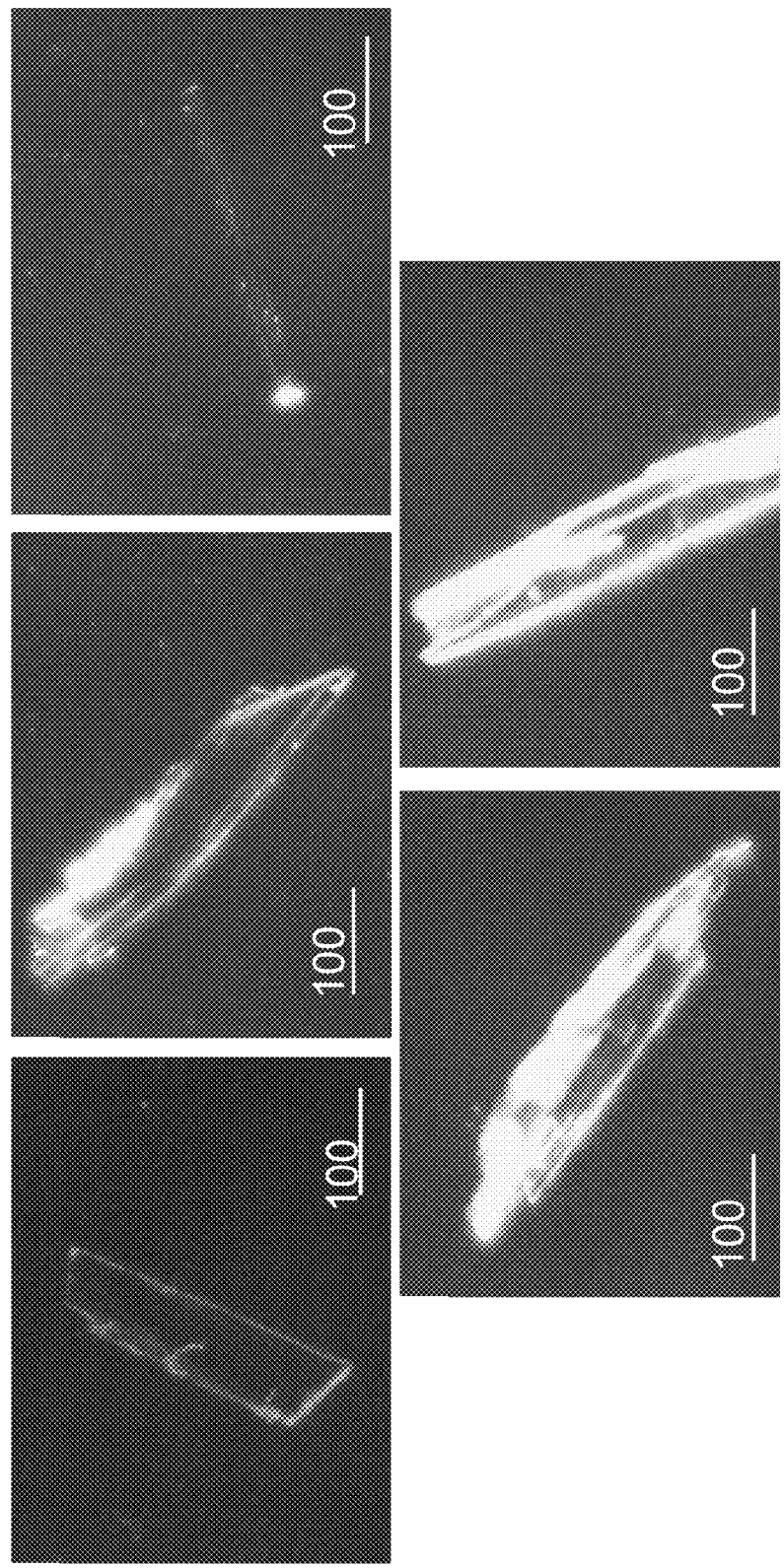
FIG. 23 shows several micrographs of various crystals of compositions comprising a co-crystallized mixture of 2,4-hexadiyn-1,6-bis(ethylurea) and 2,4-hexadiyn-1,6-bis(propylurea).

The crystals of KX monomer shown in FIG. 23 are selected from sample KX08 prepared by co-crystallization from aqueous ethanol consisting of approximately 95 percent ethanol and 5 percent water by weight, under slow cooling conditions. As can be seen by reference to the 100 μm scale appearing in each of the five frames of FIG. 23, all the crystals have a length of at least 200 μm and four of the crystals, namely KX08, have a transverse dimension for a major proportion of the length of each which is close to 100 μm, for example between about 50 μm and about 150 μm. Though substantially larger than powder crystals, crystals such as are shown in FIG. 23 do not appear large enough, or otherwise suitable, for characterization of the structure of the individual crystal by X-ray crystallography.

Applications

While reference has been made to the use of the indicators and indicator agents described herein for monitoring temperature exposure, it will be understood that other ambient environmental conditions can also be monitored in a similar manner using appropriate ones of the materials described herein. Environmental conditions that can be monitored include, by way of example, humidity, actinic radiation, atmospheric composition, environmental pressure conditions and other conditions that may be associated with the quality of the host product. The atmospheric composition can be monitored in any suitable manner, for example by reference to a component gas, for example, oxygen, carbon dioxide, ethylene or another component gas. Particular indicator agents to use for any one of these purposes can be determined without difficulty by routine experimentation by a person of ordinary skill in the art in light of the disclosure herein. The invention includes inks comprising the herein described indicator agents, the preparation of such inks and indicators prepared from the inks that are useful for monitoring temperature and other ambient conditions to indicate past exposures, particularly, but not exclusively, cumulative exposures, in an irreversible manner.

The indicator inks, materials and devices of the present invention may, if desired, be employed in a radio frequency identification, "RFID" tag as described and claimed in U.S. Pat. No. 7,209,042 to Martin et al.

Furthermore, indicator agents, indicator inks, other indicator materials and indicator devices according to the present invention may, if desired, be employed in combination with a freeze indicator or a threshold indicator or both a freeze indicator and a threshold indicator, for example, as described in U.S. Pat. No. 7,490,575 to Taylor et al., the disclosure of which is incorporated herein by reference. The freeze indicator can provide an irreversible indication of past exposure to a temperature at or near the freezing point of a liquid, for example water. The threshold indicator can provide an irreversible indication of a single past exposure to a temperature above a threshold temperature, for example a temperature above room temperature.

Indicators according to the invention can usefully be employed to assure the freshness of a wide range of perishable host products, including by way of example: perishable health care products, for example vaccines, drugs, medicaments, pharmaceuticals, medical devices and prophylactics; biological materials for industrial or therapeutic uses, for example cultures, organs and other human or animal body parts, blood and perishable blood products; diagnostic devices, kits and ingredients containing perishables; batteries and battery containing devices and appliances; foodstuffs including fresh or prepared fish, meats, dairy products, fruits, vegetables, baked goods, desserts and the like; food service products, including restaurant service foods; gourmet products; perishable animal foods; cut and uncut flowers; cosmetics, for example cosmetics containing biologicals or other labile ingredients; beauty aids; perishable munitions and ordnance; and perishable decontamination packs and products.

Additional host products whose freshness can be monitored by an indicator according to the invention are described in U.S. Patent Application Publication No. US 2007/0067177 to Martin et al., the disclosure of which is incorporated herein by reference. Still further host products whose freshness can be monitored by an indicator according to the invention will be, or become, apparent to a person of ordinary skill in the art.

Indicators according to the invention can also usefully be employed to monitor the maturity of a wide range of maturable products, including fruits, cheeses, wines and the like. Additional host products whose maturity can be monitored by an indicator according to the invention are described in U.S. Patent Application Publication No. 2006/0247967 to Prusik et al., the disclosure of which is incorporated herein by reference. Still further host products whose maturity can be monitored by an indicator according to the invention will be, or become, apparent to a person of ordinary skill in the art.

The novel diacetylenic monomer compositions or mixtures described herein can be incorporated in indicator labels as active indicator agents, if desired. The indicator label can be affixed to the host product or to its packaging or otherwise associated with the host product, or with a group or container of host products, or can be embodied in some other convenient form. If desired the label can be a self-adhesive label which can be applied directly to a host product or to its packaging.

An indicator agent according to the invention can be formulated into an ink for application to a suitable substrate by coating, printing, spraying or in another manner to provide a label, tag, package insert, package component or the like indicator device. Some suitable ink formulations and related technology which can be employed in the practice of the present invention are described in U.S. Patent Application Publication No. 2008/0004372 the entire disclosure of which is incorporated herein by reference. The labels or other indicator device can be kept in cold storage prior to application to a host product to prevent undesired polymerization of the diacetylenic monomers.

The diacetylenic monomer indicator inks of the invention can be promptly utilized for example by printing a graphical image onto a suitable substrate to create a time-temperature indicator. The substrate can be a label or package or packaging component that is readily associated with a host product. The invention includes embodiments wherein multiple labels or packages or the like are printed in sheets or continuous web configuration. Other useful indicator devices can also be made employing the indicator ink including buttons, package inserts, tags, RFID tags and so on. In some embodiments, the label or other indicator device can be associated with a host product promptly after printing or other fabrication, beginning to track or monitor the host product thermal exposure.

To avoid loss of potency of the active ink, the inks, labels or other indicator device can be subject to refrigeration or other suitable cold storage, if desired, until the indicator device is associated with a host product, whereupon it will follow the fate of the host product and begin to monitor its thermal exposure.

The indicator label can provide a color change, derived from polymerization of the diacetylenic monomer composition or mixture, which can be perceived by a human viewer at a convenient viewing distance, for example by a medical professional preparing a vaccine for administration or a shopper inspecting a refrigerated display in a supermarket.

The invention thus also provides indicator labels, tags, devices, packaging, packages and host products having such indicators associated therewith to monitor their temperature exposure, which products incorporate reactivity-enhanced indicator agents, as described herein.

An indicator employing a novel indicator agent as described herein may be associated with a host product in any desired manner for example by adhering, tying, looping, stapling or otherwise affixing a label incorporating the indicator to a desired host product, either directly to a host product or to a package containing the host product or to a package, box or container containing a multiplicity of host product items. The multiplicity of host product items may be the same items, for example pears, or different items having comparable maturation or perishability characteristics, for example certain pears and bananas.

Once associated with the intended host product, the indicator begins to monitor the thermal or other environment to which the host product is exposed. Desirably, the indicator signals a warning or readiness message, by exhibiting a color change after a predetermined cumulative exposure to elevated temperatures, or another environmental stimulus or parameter, over time. By suitable selection of indicator agent, a relatively sharp visual endpoint, can be obtained.

Disclosures Incorporated. The entire disclosure of each and every United States patent and patent application, each foreign and international patent publication, of each other publication and of each unpublished patent application that is specifically referenced in this specification is hereby incorporated by reference herein, in its entirety. Should there appear to be conflict between the meaning of a term employed in the description of the invention in this specification and with the usage in material incorporated by reference from another document, the meaning as used herein is intended to prevail.

The foregoing detailed description is to be read in light of and in combination with the preceding background and invention summary descriptions wherein partial or complete information regarding the best mode of practicing the invention, or regarding modifications, alternatives or useful embodiments of the invention may also be set forth or suggested, as will be apparent to one skilled in the art. The description of he invention is intended to be understood as including combinations of the various elements of the invention, and of their disclosed or suggested alternatives, including alternatives disclosed, implied or suggested in any one or more of the various methods, products, compositions, systems, apparatus, instruments, aspects, embodiments, examples described in the specification or drawings, if any, and to include any other written or illustrated combination or grouping of elements of the invention or of the possible practice of the invention, except for groups or combinations of elements that will be or become apparent to a person of ordinary skill in the art as being incompatible with or contrary to the purposes of the invention.

Throughout the description, where compositions are described as having, including, or comprising specific components, or where processes are described as having, including, or comprising specific process steps, it is contemplated that compositions of the present invention can also consist essentially of, or consist of, the recited components, and that the processes of the present invention can also consist essentially of, or consist of, the recited processing steps. It should be understood that the order of steps or order for performing certain actions is immaterial so long as the invention remains operable. Moreover, two or more steps or actions may be conducted simultaneously. In addition, all proportions recited herein are to be understood to be proportions by weight, based upon the weight of the relevant composition, unless the context indicates otherwise.

While illustrative embodiments of the invention have been described above, it is, of course, understood that many and various modifications will be apparent to those of ordinary skill in the relevant art, or may become apparent as the art develops, in the light of the foregoing description. Such modifications are contemplated as being within the spirit and scope of the invention or inventions disclosed in this specification.

The invention claimed is:

1. A solid monomer composition comprising a first monomer and a second monomer, each said monomer having the formula:

$$CH_3(CH_2)_{m1}NHCONH(CH_2)(-C\equiv C-)_2(CH_2)NHCONH(CH_2)_{m5}CH_3;$$

wherein
in the first monomer m1 and m5 are both 1;
in the second monomer m1 and m5 are both 2;
the solid monomer composition can exhibit an X-ray powder diffraction spectrum having three reflection peaks between a d spacing of about 4.28 Å and a d spacing of about 3.81 Å, the diffraction spectrum being collected using $CuK_{\alpha 1}$ radiation;
the three reflection peaks comprise a long spacing peak at a d spacing in the range of from about 4.28 Å to about 4.18 Å, an intermediate spacing peak at a d spacing in the range of from about 4.11 Å to about 3.99 Å, and a short spacing peak at a d spacing in the range of from about 3.94 Å to about 3.81 Å; and
the solid monomer composition is thermally polymerizable to have a changed visual appearance.

2. The solid monomer composition of claim 1 wherein the X-ray powder diffraction spectrum comprises a separation between the long spacing peak and the intermediate spacing peak of from about 0.10 Å to about 0.27 Å, and a separation between the intermediate spacing peak and the short spacing peak of from about 0.07 Å to about 0.26 Å.

3. The solid monomer composition of claim 1 wherein the three reflection peaks are the highest intensity peaks for the diffraction spacing range between about 4.28 Å and 3.81 Å and wherein the intensity of the intermediate spacing peak is higher than the intensity of either the long spacing peak or the short spacing peak.

4. The solid monomer composition of claim 1 comprising a ratio of the first monomer to the second monomer in the range of from about 3:1 to about 1:1 by weight.

5. The solid monomer composition of claim 4 comprising a ratio of the first monomer to the second monomer of about 2:1 by weight.

6. The solid monomer composition of claim 4 comprising a ratio of the first monomer to the second monomer of about 1:1 by weight.

7. The solid monomer composition of claim 5, wherein the X-ray powder diffraction spectrum comprises a longest spacing peak and a second longest spacing peak, the longest and second longest spacing peaks being singlet peaks at d spacings of about 17.80 Å and about 8.91 Å respectively.

8. A solid monomer composition comprising a first monomer and a second monomer, each said monomer having the formula:

$$CH_3(CH_2)_{m1}NHCONH(CH_2)(-CC-)_2(CH_2)NHCONH(CH_2)_{m5}CH_3;$$

wherein:
in the first monomer m1 and m5 are both 1;
in the second monomer m1 and m5 are both 2;
the solid monomer composition can exhibit an X-ray powder diffraction spectrum having two reflection peaks between a d spacing of about 4.40 Å and a d spacing of about 3.95 Å, and being collected using $CuK_{\alpha 1}$ radiation;
the two reflection peaks comprise a long spacing peak at a d spacing in the range of from about 4.43 Å to about 4.37 Å, and a short spacing peak at a d spacing in the range of from about 3.99 Å to about 3.92 Å; and
the solid monomer composition is thermally polymerizable to have a changed visual appearance.

9. The solid monomer composition of claim 8 wherein the two reflection peaks are the highest intensity peaks in the diffraction spacing range of from about 4.43 Å to about 3.92 Å and wherein the intensities of the two peaks are similar.

10. The solid monomer composition of claim 8 comprising a ratio of the first monomer to the second monomer of about 2:1 by weight.

11. The solid monomer composition of claim 10, wherein the X-ray powder diffraction spectrum comprises a longest spacing peak and a second longest spacing peak, the longest and second longest spacing peaks being essentially singlets at d spacings of about 17.80 Å and about 8.91 Å respectively.

12. A thermally polymerizable co-crystallized solid monomer composition comprising a first monomer, and a second monomer, each said monomer having the formula:

$$CH_3(CH_2)_{m1}NHCONH(CH_2)(-CC-)_2(CH_2)NHCONH(CH_2)_{m5}CH_3,$$

wherein
in the first monomer m1 and m5 are both 1;
in the second monomer m1 and m5 are both 2;
the solid monomer composition can exhibit an X-ray powder diffraction spectrum collected using $CuK_{\alpha 1}$ radiation comprising a longest spacing peak and a second longest spacing peak;
the longest and second longest spacing peaks are essentially singlets; and
the second longest spacing peak is at a d spacing of about half the d spacing of the longest spacing peak.

13. The solid monomer composition of claim 12 wherein the longest spacing peak is at a d spacing of from about 16.4 Å to about 20.1 Å.

14. The solid monomer composition of claim 12 comprising a ratio of the first monomer to the second monomer of about 2:1 by weight.

15. The solid monomer composition of claim 12 comprising a ratio of the first monomer to the second monomer of about 1:1 by weight.

16. A crystal phase composition comprising a first crystal phase and a second crystal phase, wherein the first crystal phase comprises at least about 20 weight percent of a first monomer, the balance consisting essentially of a second monomer, and the second crystal phase comprises at least about 20 weight percent of the second monomer, the balance consisting essentially of the first monomer and wherein the first monomer and the second monomer have differing molecular structures of formula:

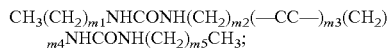

$CH_3(CH_2)_{m1}NHCONH(CH_2)_{m2}(-CC-)_{m3}(CH_2)_{m4}NHCONH(CH_2)_{m5}CH_3;$ wherein
- m1 is 0 or is a positive integer in the range of from 1 to about 17;
- m2 is a positive integer in the range of from 1 to about 10;
- m3 is a positive integer in the range of from 2 to 4;
- m4 is a positive integer in the range of from 1 to about 10;
- m5 is 0 or is a positive integer in the range of from 1 to about 17;
- in each of the two monomers m2, 3, and m4 are the same integer;
- at least one of m1 and m5 in the first monomer differs by one from m1 or m5, respectively, in the second monomer; and
- the crystal phase composition can exhibit an X-ray powder diffraction spectrum having a longest spacing peak being a singlet peak and a second longest spacing peak being a shoulder peak or a doublet peak, the diffraction spectrum being collected using $CuK_{\alpha 1}$ radiation.

17. The crystal phase composition of claim 16, wherein m3 is two and wherein in the first monomer, m1 and m5 are both 1, and in the second monomer, m1 and m5 are both 2.

18. The crystal phase composition of claim 16 wherein, in the first monomer, m1 and m5 are both 1 and in the second monomer m1 and m5 are both 2, the longest spacing peak is at a d spacing of about 17.80 Å, and the second longest spacing peak is at a d spacing of about 8.91 Å.

19. The crystal phase composition of claim 16 wherein the first crystal phase comprises at least about 50 weight percent of the first monomer and the second crystal phase comprises at least about 50 weight percent of the second monomer.

20. A time-temperature indicator comprising a composition according to claim 1.

* * * * *